(12) United States Patent
Carl

(10) Patent No.: US 11,150,239 B2
(45) Date of Patent: Oct. 19, 2021

(54) METHOD OF ISOLATING A TARGET CELL

(71) Applicant: IBA LIFESCIENCES GMBH, Gottingen (DE)

(72) Inventor: Uwe D. Carl, Hardegsen (DE)

(73) Assignee: IBA LIFESCIENCES GMBH, Gottingen (DE)

( * ) Notice: Subject to any disclaimer, the term of this patent is extended or adjusted under 35 U.S.C. 154(b) by 0 days.

(21) Appl. No.: 15/306,995

(22) PCT Filed: Apr. 30, 2015

(86) PCT No.: PCT/EP2015/059510
§ 371 (c)(1),
(2) Date: Oct. 26, 2016

(87) PCT Pub. No.: WO2015/166049
PCT Pub. Date: Nov. 5, 2015

(65) Prior Publication Data
US 2017/0052176 A1 Feb. 23, 2017

(30) Foreign Application Priority Data

Apr. 30, 2014 (EP) .................................. 14166718

(51) Int. Cl.
| G01N 33/543 | (2006.01) |
| G01N 33/566 | (2006.01) |
| C07K 16/28 | (2006.01) |

(52) U.S. Cl.
CPC ....... *G01N 33/54306* (2013.01); *C07K 16/28* (2013.01); *G01N 33/543* (2013.01); *G01N 33/566* (2013.01); *G01N 2333/705* (2013.01)

(58) Field of Classification Search
CPC ........... G01N 33/54306; G01N 33/543; G01N 33/566; G01N 2333/705; C07K 16/28
See application file for complete search history.

(56) References Cited

U.S. PATENT DOCUMENTS

| 4,851,341 A | 7/1989 | Hopp et al. |
| 5,985,658 A | 11/1999 | Colinas et al. |
| 6,022,951 A | 2/2000 | Sano et al. |
| 6,103,493 A | 8/2000 | Skerra et al. |
| 7,776,562 B2 | 8/2010 | Busch et al. |
| 8,299,782 B2 | 10/2012 | Mizuno et al. |
| 2009/0215088 A1 | 8/2009 | Forsyth et al. |

FOREIGN PATENT DOCUMENTS

| DE | 19641876 A1 | 4/1998 |
| WO | 8602077 A1 | 4/1986 |
| WO | 9623879 A1 | 8/1996 |
| WO | 9624606 A1 | 8/1996 |
| WO | 9840396 A1 | 9/1998 |
| WO | 0104144 A2 | 1/2001 |
| WO | 02054065 A2 | 7/2002 |
| WO | 03029462 A1 | 4/2003 |
| WO | 2012044999 A2 | 4/2012 |
| WO | 2013011011 A2 | 1/2013 |
| WO | 2013124474 A2 | 8/2013 |

OTHER PUBLICATIONS

International Search Report issued in PCT/EP2015/059510 dated Aug. 24, 2015 (5 pages).
Written Opinion issued in PCT/EP2015/059510 dated Aug. 24, 2015 (9 pages0.
Argarana et al., Molecular cloning and nucleotide sequence of the streptavidin gene. Nucleic Acids Res. Feb. 25, 1986;14(4):1871-1882.
Beste et al., Small antibody-like proteins with prescribed ligand specificities derived from the lipocalin fold. Proc Natl Acad Sci U S A. Mar. 2, 1999;96(5)1898-1903.
Bolliger et al., "Diabodies": Small bivalent and bispecific antibody fragments. Proc Natl Acad Sci U S A. Jul. 15, 1993;90(14):6444-6448.
Braun et al., Rapid Separation of T Cell Subpopulations with Monoclonal Antibodies and Affinity Chromatography. J Immunol Methods. Oct. 29, 1982;54(2):251-258.
Dainiak et al., Chromatography of Living Cells Using Supermacroporous Hydrogels, Cryogels. Adv Biochem Eng Biotechnol. 2007;106:101-127.
Gill and Damle, Biopharmaceutical drug discovery using novel protein scaffolds. Curr Opin Biotechnol. Dec. 2006;17(6):653-658.
Holt et al., Domain antibodies: proteins for therapy. Trends Biotechnol. Nov. 2003;21(11):484-490.
Hutten et al., New magnetic nanoparticles for biotechnology. J Biotechnol. Aug. 26, 2004;112(1-2):47-63.
Iliades et al., Triabodies: single chain Fv fragments without a linker form trivalent trimers. FEBS Lett. Jun. 16, 1997;409(3):437-441.
Ill et al., Design and construction of a hybrid immunoglobulin domain with properties of both heavy and light chain variable regions. Protein Eng. Aug. 1997;10(8):949-957.
Martin et al., The affinity-selection of a minibody polypeptide inhibitor of human interleukin-6. EMBO J. Nov. 15, 1994;13(22):5303-5309.
Mosavi et al., The ankyrin repeat as molecular architecture for protein recognition. Protein Sci. Jun. 2004;13(6):1435-1448.
Noguchi et al., Preparation and Properties of the Immunoconjugate Composed of Anti-Human Colon Cancer Monoclonal Antibody and Mitomycin C-Dextran Conjugate. Bioconjug Chem. Mar.-Apr. 1992;3(2):132-137.
Ohba et al., Fractionation of normal and leukemic T-cells by lectin-affinity column chromatography. Cancer Lett. Oct. 28, 2002;184(2):207-214.

(Continued)

*Primary Examiner* — Ruixiang Li
(74) *Attorney, Agent, or Firm* — Acuity Law Group, PC; Michael A. Whittaker

(57) ABSTRACT

The invention provides new methods of isolating target cells using a solid phase, the solid phase comprising a ligand L wherein the ligand L is capable of specifically binding a ligand binding partner LB, the ligand binding partner LB being present in a receptor molecule binding reagent or a multimerization reagent used for isolating target cells. The invention also provides corresponding new arrangements and devices for isolating a target cell from a sample.

20 Claims, 21 Drawing Sheets

Specification includes a Sequence Listing.

(56) References Cited

OTHER PUBLICATIONS

Schmidt et al., Reversible Major Histocompatibility Complex I-Peptide Multimers Containing Ni2+-Nitrilotriacetic Acid Peptides and Histidine Tags Improve Analysis and Sorting of CD8+ T Cells. J Biol Chem. Dec. 2, 2011;286(48):41723-41735.

Silverman et al., Multivalent avimer proteins evolved by exon shuffling of a family of human receptor domains. Nat Biotechnol. Dec. 2005;23(12):1556-1561.

Skerra, Engineered protein scaffolds for molecular recognition. J Mol Recognit. Jul.-Aug. 2000;13(4):167-187.

Stone et al., The assembly of single domain antibodies into bispecific decavalent molecules. J Immunol Methods. Jan. 10, 2007;318(1-2):88-94.

Traunecker et al., Bispecific single chain molecules (Janusins) target cytotoxic lymphocytes on HIV infected cells. EMBO J. Dec. 1991;10(12):3655-3659.

Traunecker et al., Janusin: new molecular design for bispecific reagents. Cancer Suppl. 1992;7:51-52.

Beste et al., "Small antibody-like proteins with prescribed ligand specificities derived from the lipocalin fold", Proc. Natl. Acad. Sci. USA, vol. 96, pp. 1898-1903, Mar. 1999.

Chen et al., "General principles of binding between cell surface receptors and multi-specific ligands: A computational study", PLoS Comput Biol 13(10): e1005805. https://doi.org/10.1371/journal.pcbi.1005805.

Efremova et al., "CellPhoneDB: Inferring cell-cell communication from combined expression of multi-subunit ligand-receptor complexes", Nat Protoc. Apr. 2020;15(4):1484-1506. doi: 10.1038/s41596-020-0292-x. Epub Feb. 26, 2020.

Harris et al., "Comparison of T Cell Activities Mediated by Human TCRs and CARs That Use the Same Recognition Domains", J Immunol published online Dec. 29, 2017, http://www.jimmunol.org/content/early/2017/12/29/immunol.1700236.

He et al., "TCR-like antibodies in cancer immunotherapy", Journal of Hematology & Oncology (2019) 12:99 https://doi.org/10.1186/s13045-019-0788-4.

Napolitano et al., "Glubodies: randomized libraries of glutathione transferase enzymes", Chem Biol May 1996;3(5):359-67. doi: 10.1016/s1074-5521(96)90119-2.

Sha et al., "Monobodies and other synthetic binding proteins for expanding protein science", Protein Sci. May 2017;26(5):910-924. doi: 10.1002/pro.3148. Epub Mar. 24, 2017.

Silverman et al., "Multivalent avimer proteins evolved by exon shuffling of a family of human receptor domains", Nat Biotechnol. Dec. 2005;23(12):1556-61. doi: 10.1038/nbt1166. Epub Nov. 20, 2005.

Skerra, A., "'Anticalins': a new class of engineered ligand-binding proteins with antibody-like properties", J Biotechnol. Jun. 2001;74(4)257-75. doi: 10.1016/s1389-0352(01)00020-4.

Skerra, A., "Engineered protein scaffolds for molecular recognition", J Mol Recognit. Jul.-Aug. 2000;13(4):167-87.

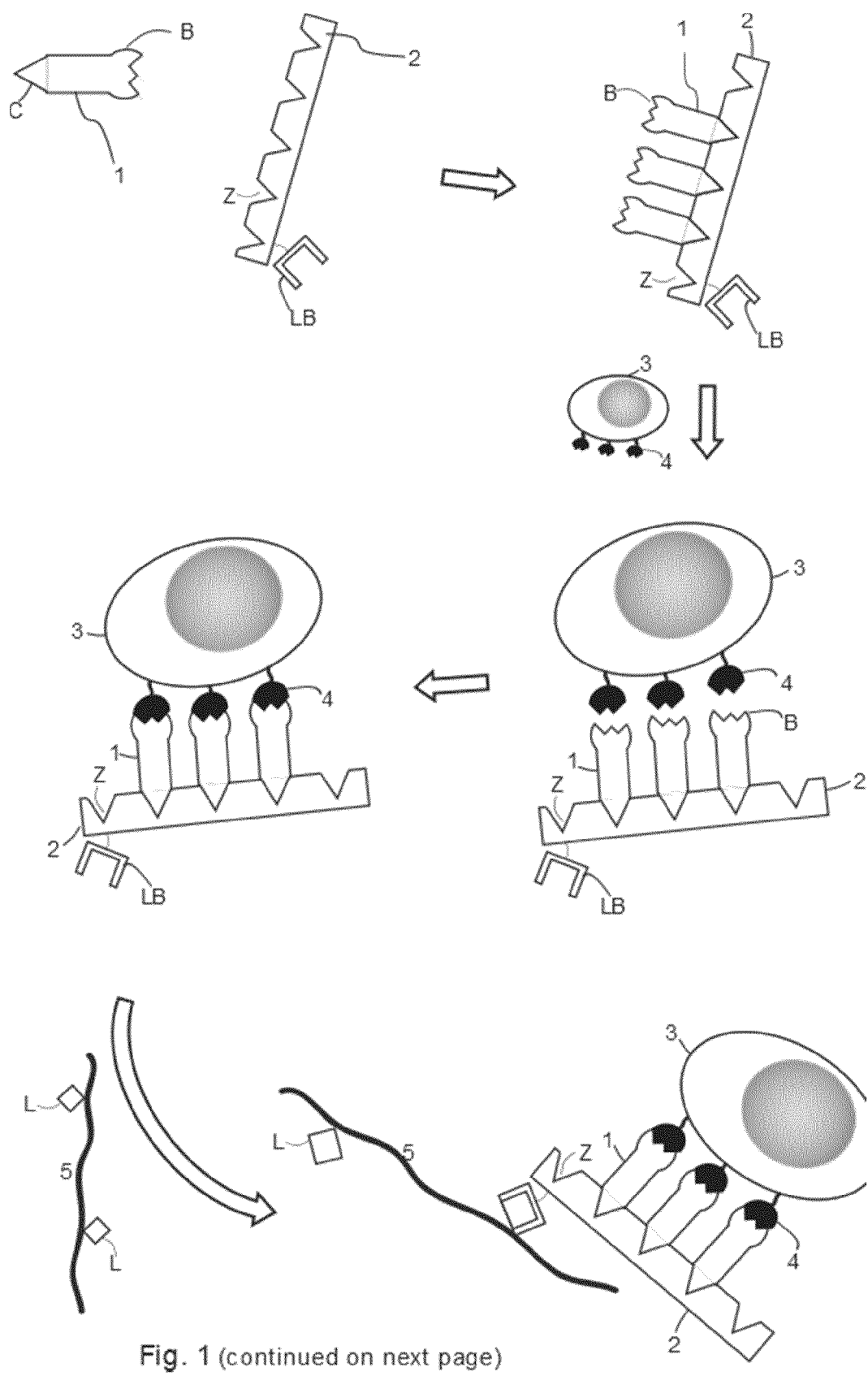
Fig. 1 (continued on next page)

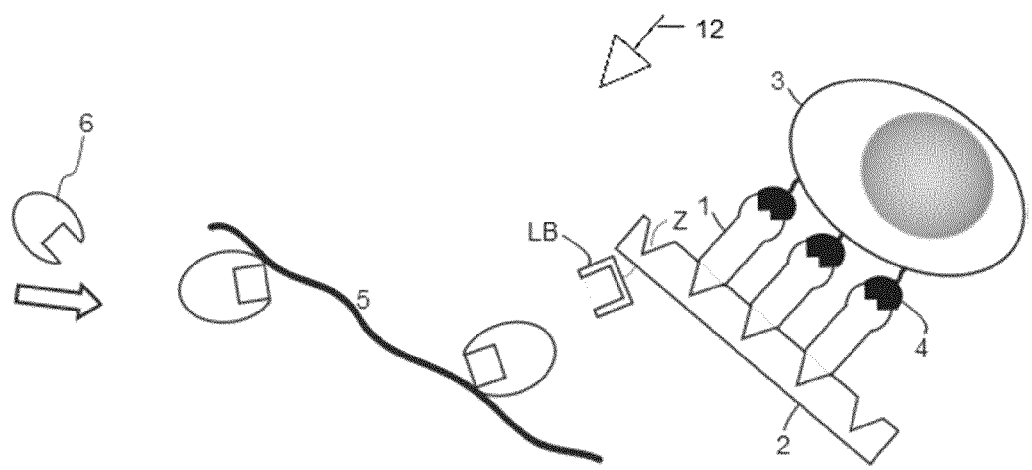
Fig. 1 (continued from prev. page)
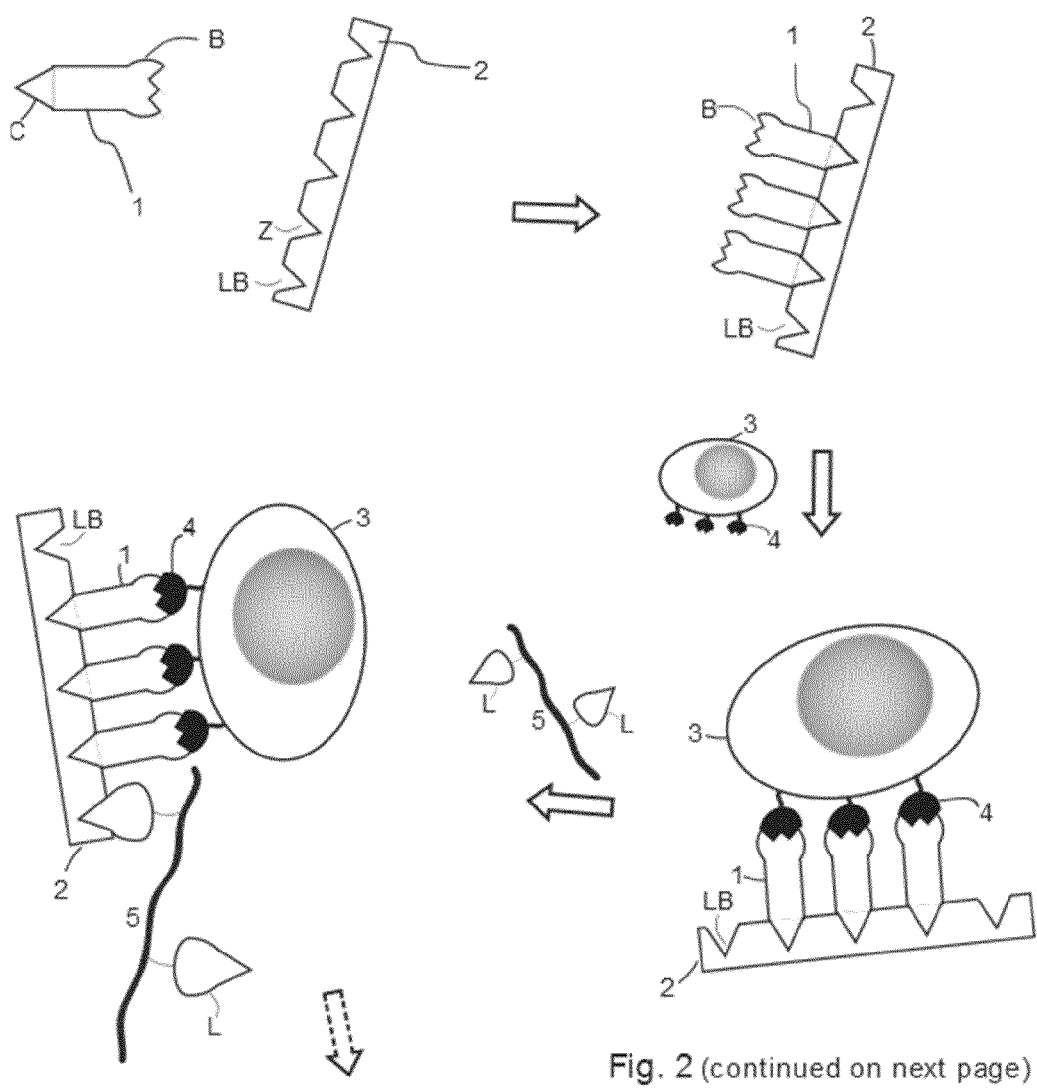
Fig. 2 (continued on next page)

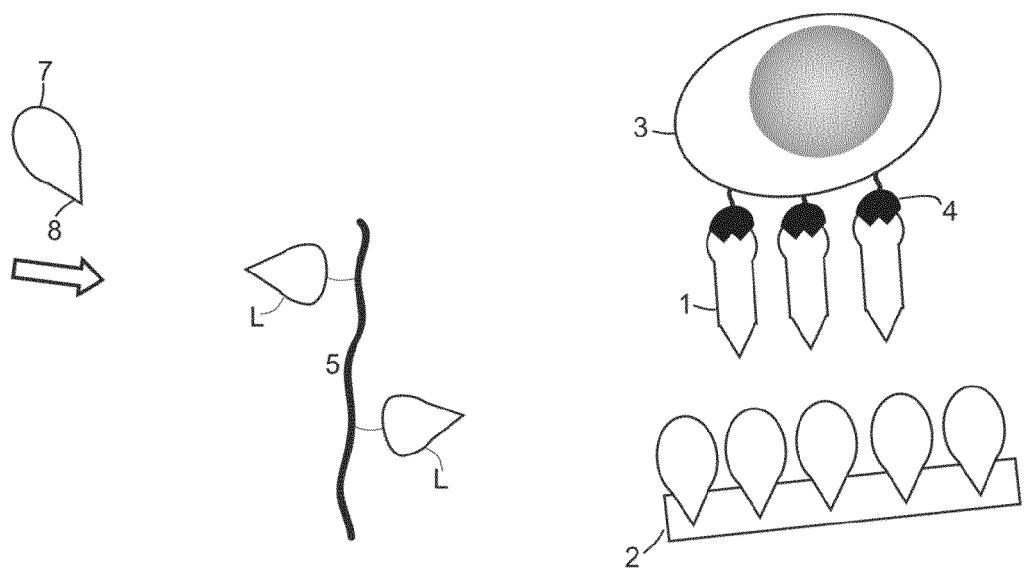
Fig. 2 (continued from prev. page)
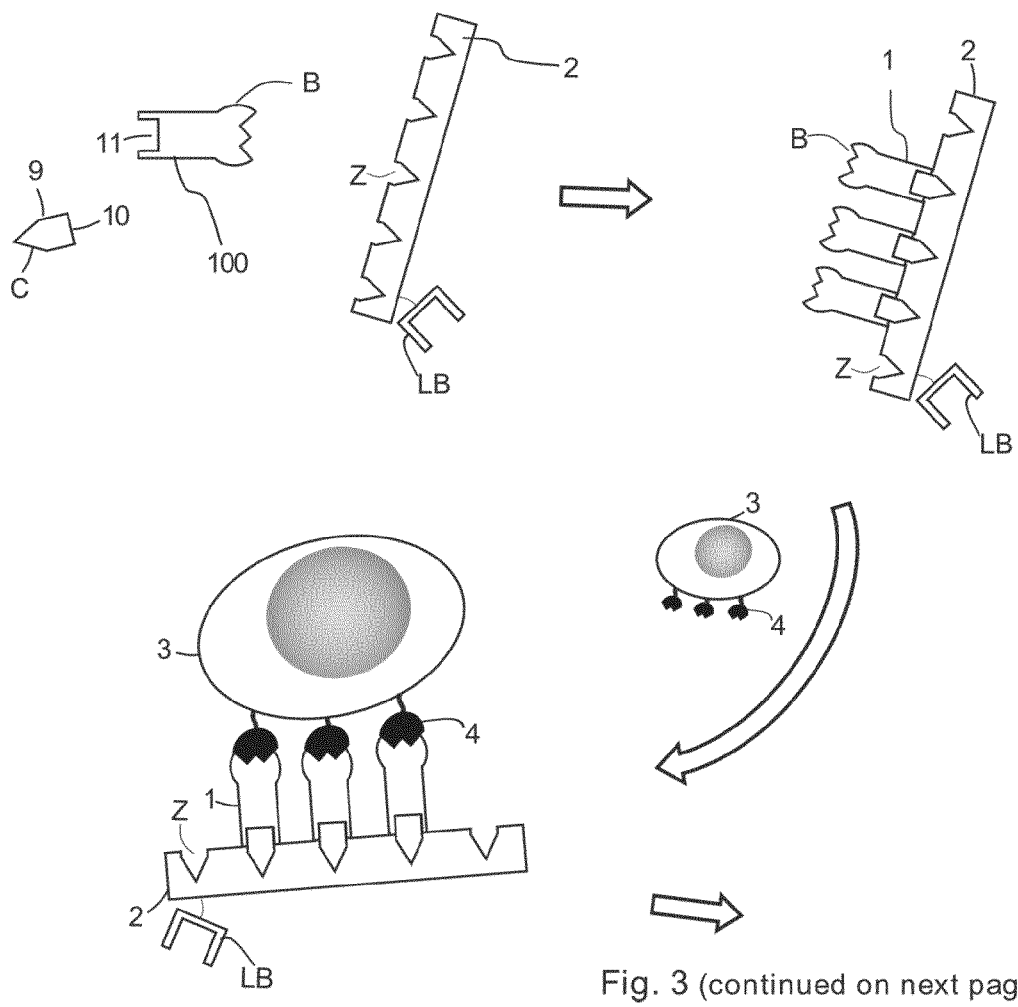
Fig. 3 (continued on next page)

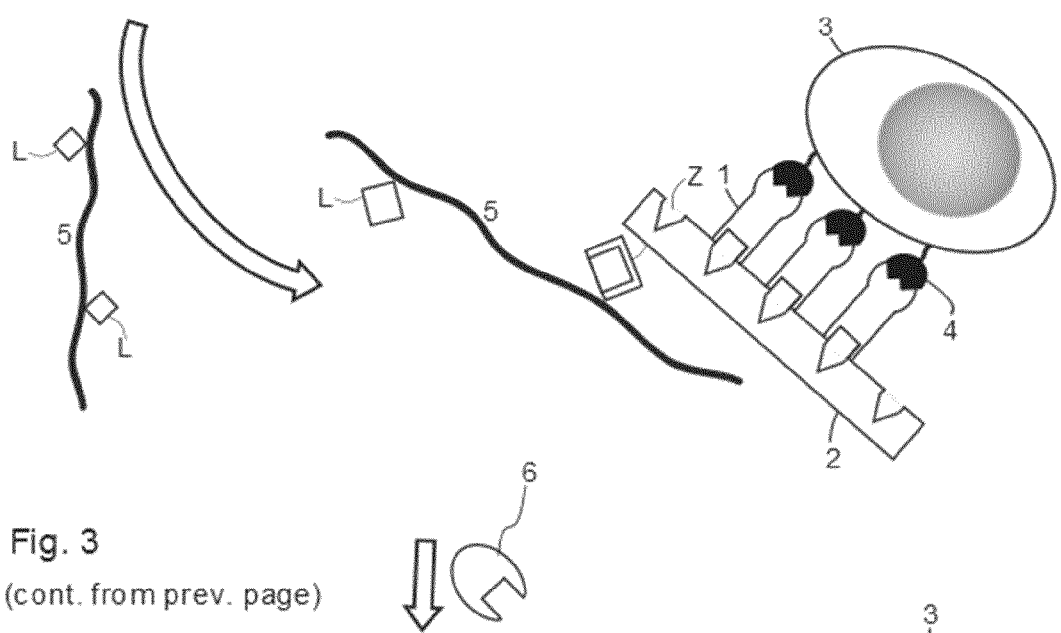
Fig. 3
(cont. from prev. page)
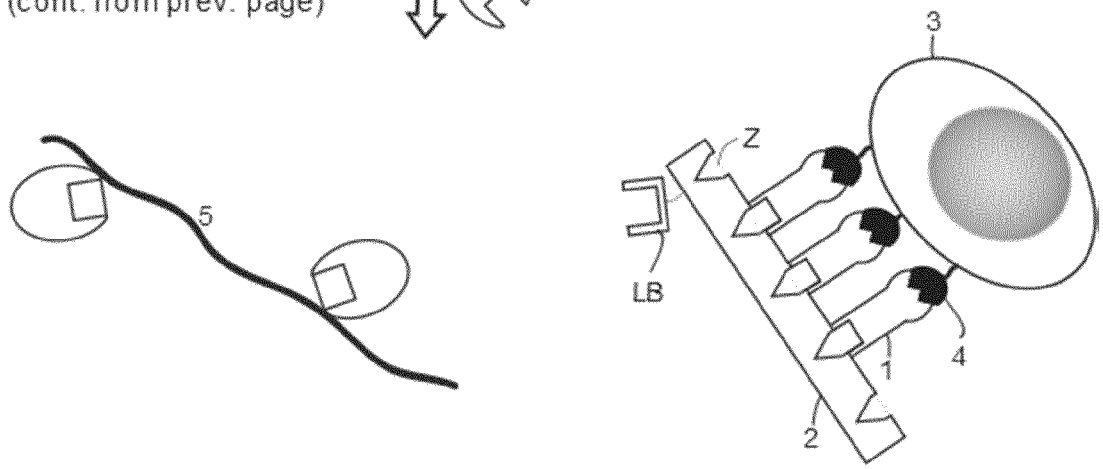

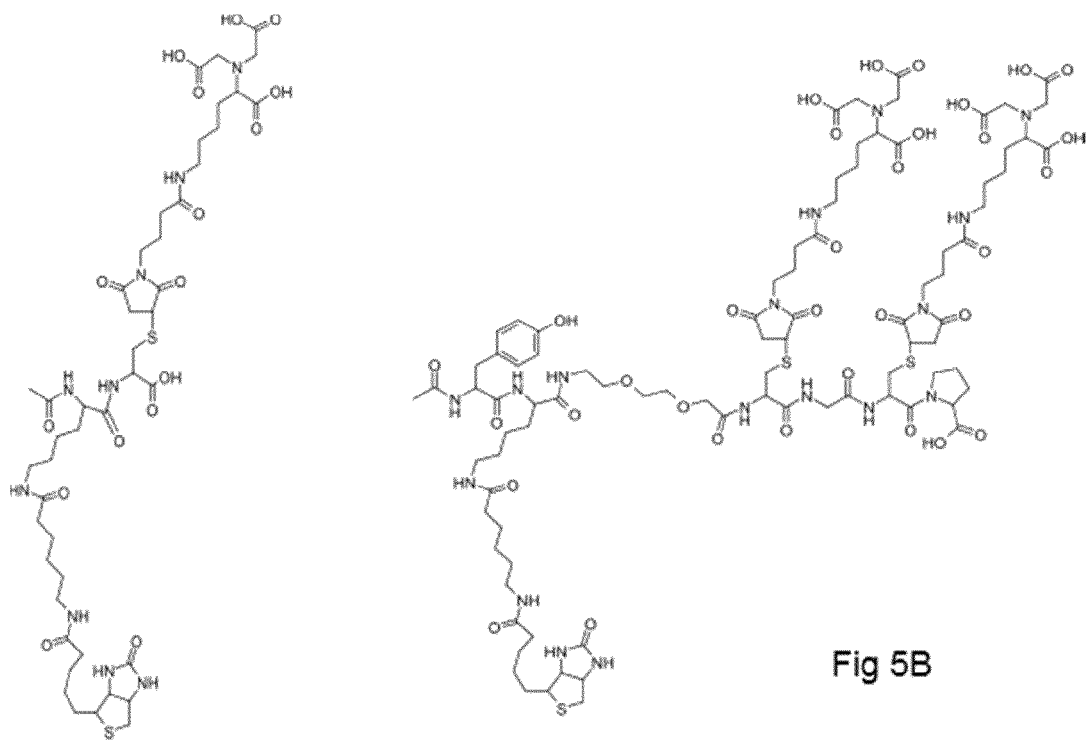
Fig. 5A
Fig 5B
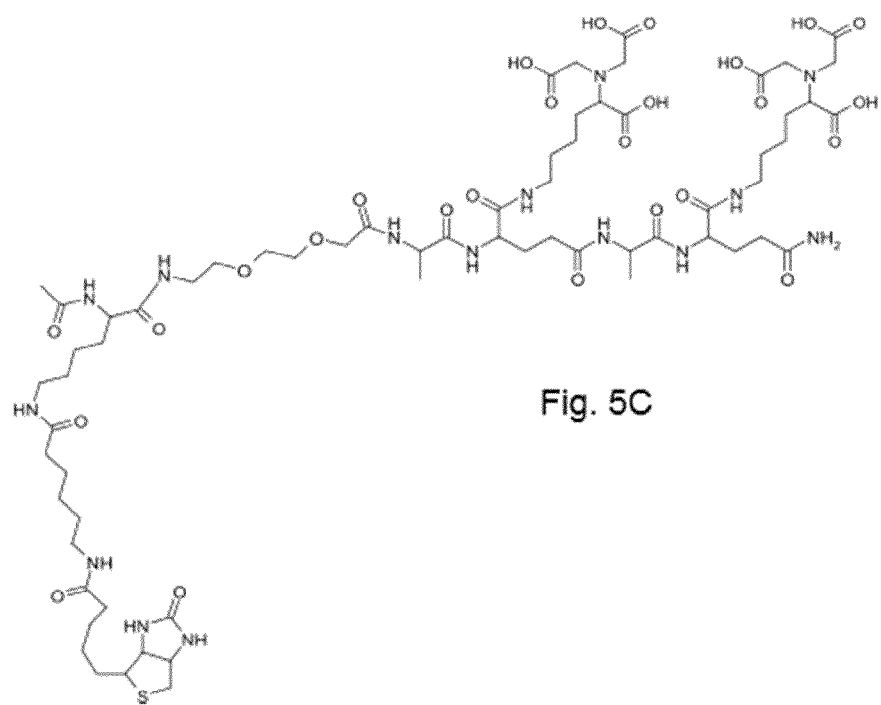
Fig. 5C

| Fig. 7 | Plot 1 (FSC-A/SSC-A) | | Plot 3 (FL2-A/FL4-A) | | |
|---|---|---|---|---|---|
| | All | | P1 | Q3-UR | |
| | Count | Volume µL | Count | Count | % of this Plot |
| E01 CD3PE CD4APC | 41.674 | 2 | 10.000 | 3.956 | 39.56% |
| E02 unstained | 39.053 | 2 | 10.000 | 0 | 0.00% |
| E06 D+W4 | 51.109 | 3 | 10.000 | 401 | 4.01% |
| F01 E 4 | 14.720 | 4 | 10.000 | 9.504 | 95.04% |
| F08 R 4 | 15.622 | 19 | 10.000 | 8.826 | 88.26% | before selection wash through fraction positive fraction wash through fraction positive fraction before selection wash through fraction positive fraction Fig. 10B
wash through fraction
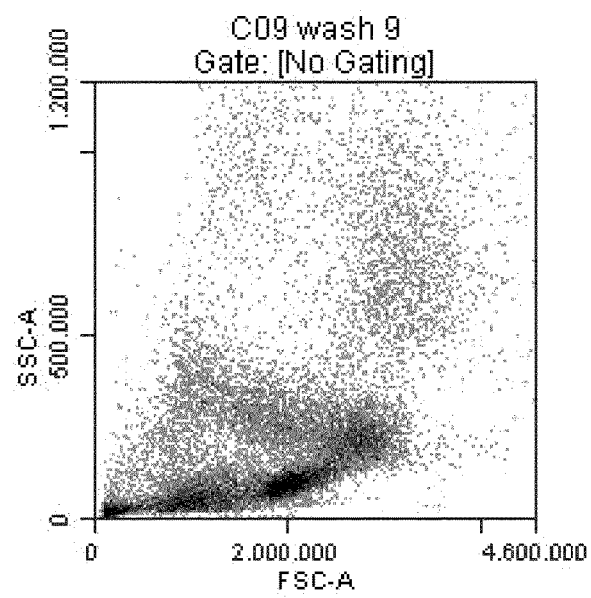
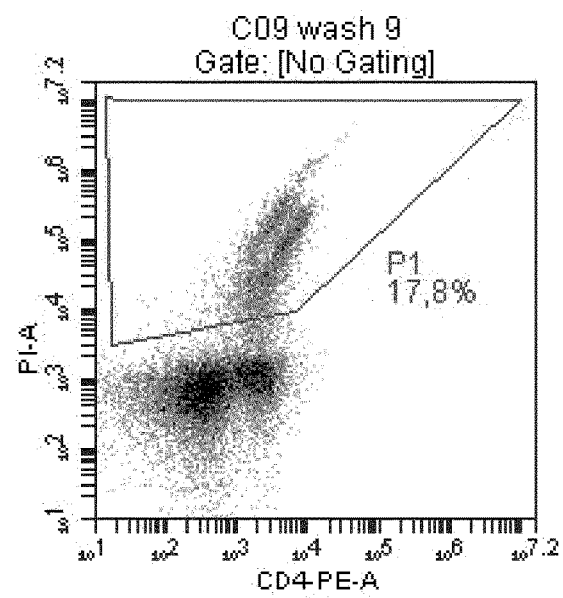
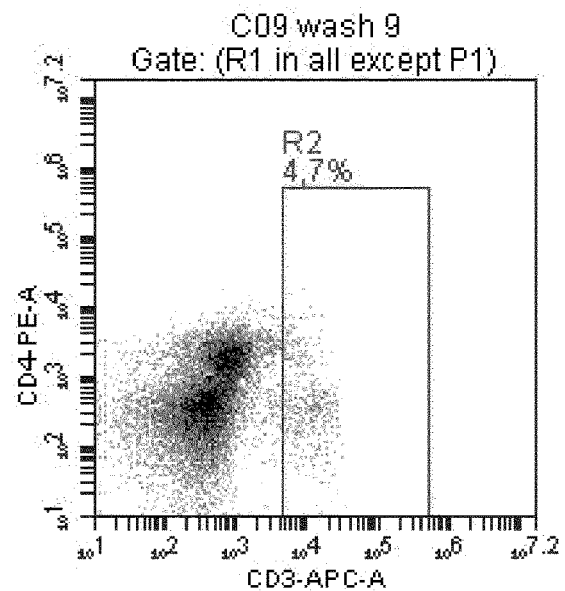

positive fraction

METHOD OF ISOLATING A TARGET CELL

CROSS-REFERENCE TO RELATED APPLICATIONS

The present invention is filed under 35 U.S.C. § 371 as the U.S. national phase of International Application No. PCT/EP2015/059510, filed 30 Apr. 2015, which designated the U.S. and claims the right of priority of European patent application no. 14166718.8 filed on 30 Apr. 2014, the entire contents of each of which is incorporated herein for all purposes.

FIELD OF THE INVENTION

The present invention relates to a method of isolating of a target bioentity such as a cell or other biological material, e.g. as a cell organelle or a virus. The method may be taken to define a chromatographic method, including a method of column chromatography. The invention also relates to new arrangements for isolating a target cells from a sample as well as corresponding devices. The invention also relates to the use of a stationary phase with a ligand thereon for the isolation of target cells.

BACKGROUND OF THE INVENTION

Isolation of pure and functional cell populations of a desired cell type is a prerequisite in a variety of therapeutic, diagnostic, and biotechnological applications.

Chromatography is a well-established technique for the separation of low molecular weight and high molecular weight molecules, including proteins. This technique has also been applied to cell separation, in particular in the form of affinity chromatography using immobilized ligands specific to a desired cell type, such as immunoligands. As an example, different T cell subsets have been separated by labelling with monoclonal immunoglobulins and loading onto a column with polyacrylamide beads, to which rabbit anti-mouse IgG was covalently bound (Braun, R., et al., Journal of Immunological Methods (1982) 54, 251-258). As a further example, lectin-affinity column chromatography, using Sepharose 6 MB covalently conjugated to *Dolichos biflorus* agglutinin, has been used to separate leukemic cells from healthy leukocytes (Ohba, H., et al, Cancer Letters (2002) 184, 207-214).

As cells are generally by magnitudes larger than proteins they hardly enter, in contrast to proteins, the pores of the beads of conventional chromatography sorbents. Using sorbents with large pores does not significantly overcome this separation phenomenon due to diffusional limitations. On the other hand, the surface area within pores only accessible for proteins usually largely exceeds the surface area accessible for both proteins and cells. Therefore, the use of conventional chromatography sorbents for the immobilization of proteinaceous or other receptor binding ligands for the generation of an affinity matrix for cells usually requires the use of a wasteful large excess of receptor binding ligands as most of them are immobilized in pores or cavities that cannot be accessed by the cells. Specific receptor binding reagents are often expensive and difficult to be produced at the desired scales thereby bringing this aspect to serious consideration. The use of monolithic sorbents in the form of cryogels has therefore been suggested as an alternative technique in affinity chromatography of cells (see e.g. Dainiak, M. B., et al., Adv. Biochem. Engin./Biotechnol. (2007), 106, 101-127). However, monolithic sorbents are scarce so that a desired sorbent may not be commercially available in the form of a monolithic column. Furthermore, in case of affinity chromatography, generally the need remains to remove a competing compound used to elute the desired cells from these cells. Potential advantages of monolithic sorbents in terms of cell viability may thus be reversed by additional procedures required to remove the compound used to elute the cells from the affinity chromatography column.

The most important currently used cell isolation methods are magnet-assisted cell sorting (MACS) and fluorescence-assisted cell sorting (FACS™). Cell sorting by flow cytometry, where typically fluorophores, coupled to antibodies, are used to label cells, analyses cells individually. Cells are separated at high speed under very high pressures using a cell sorting apparatus. FACS™ technology enables isolation of cells defined by a set of markers in one step by applying a corresponding set of antibodies with different fluorophores. The method is thus reliable, but time and cost intensive and laborious. Especially for the selection out of very large, diverse cell populations e.g., apheresis products containing $1 \times 10^{10}$ cells very long sorting times of flow cytometers are unacceptable for an appropriate selection process. Another drawback of FACS™ is that complex and interference-prone flow cytometers can hardly be adapted to a GMP environment necessary for isolating therapeutic cell products. Moreover, the applied pressures during the cell selection procedure may compromise cell effector function.

Magnet-assisted isolation of cells is a widely used system for research and therapeutic application. Although yield and purity of isolated cells are moderate compared to the FACS™ technology the selection procedure is robust and does not require sophisticated automatization. The major drawbacks of the magnet-assisted isolation are the remaining staining reagents including the magnetic beads on the isolated cells which may compromise effector function of isolated cell populations. In addition no serial positive selection processes are possible due to these remaining magnetic reagents on the isolated cells. Serial positive selection procedures are mandatory for selecting cell populations defined by a set of markers.

While still making use of a magnetic or fluorescent label, a significant advancement in the isolation of cells is the "Streptamer®" technology that is, for example, described in International Patent Application WO 02/054065, U.S. Pat. Nos. 7,776,562 and 8,299,782 in which a receptor molecule binding reagent exhibiting a low affinity binding to a receptor molecule located on a surface of a cell is used for the reversible staining and isolation of cells. In contrast to the currently used single positive selection combined with magnetic negative selection (aiming at removal of all cell populations but the one of interest) serial positive selection using the Streptamer® technology with removal of the low affinity receptor binding reagent after each selection generate cell populations of very high purity and yield.

In addition, the International Patent Application WO 2013/124474 describes the chromatographic isolation of target cells by column chromatography. In this method, a receptor molecule binding reagent such as a Fab fragment that binds to a receptor molecule that is located on the surface of a target cell is reversibly immobilized on a stationary chromatographic phase via an affinity tag such as streptavidin binding peptide. For this immobilization, the stationary phase comprise an affinity reagent that forms a reversible bond with the affinity tag, for example, a streptavidin mutein that reversibly binds to the streptavidin binding peptide that is part of the receptor molecule binding reagent.

A sample containing the target cell is then contacted with the stationary phase and reversibly immobilized thereon by binding to the receptor molecule binding reagent. The target cells are then isolated/eluted from the stationary phase by adding a competition reagent that also binds to the binding site of the affinity reagent thereby displacing the receptor molecule binding reagent from the stationary phase and thus also releasing the target cells from the stationary phase. A similar chromatographic purification that uses monoclonal intact antibodies instead of (monovalent) antibody fragments as receptor molecule binding reagents is described in example 11 of U.S. Pat. No. 6,022,951.

The method of International Patent Application WO 2013/124474 might however have several limitations. In case the Fab fragment is immobilized onto the chromatography column (the stationary chromatographic phase) the sample with the target cells is then applied to the chromatography column, the on-rate ($k_{on}$) of the complex formation, i.e. of the binding of the Fab fragment to the receptor molecule, may become limiting for the immobilization of the target cells due to the flow rate used for loading the sample onto the column. In such a case, not all of the target cells might be bound to the chromatography column. This may lead to a low yield of the purified target cells. In addition, the distribution of the immobilized Fab fragment on the chromatography column may be uneven. When loading the Fab fragments on the column, the Fab fragments may predominantly bind on the top portion of the column, leading to a too high density on this top portion and a too low density in the lower portion of the column. This might lead to insufficient complex formation and thus also affect the yield of the isolated cells. In addition, a relatively large amount of the Fab fragment is needed in order to ensure that the entire chromatographic resin is evenly coated with the Fab fragment. In order to avoid the problem of the on-rate of the complex formation between the Fab fragment and the receptor molecules of the target cells becoming rate limiting, it is possible in the method of International Patent Application WO 2013/124474 to first incubate the Fab fragment with the sample that contains the target cells and apply this incubation mixture onto the chromatography column. In this case, the affinity of the Fab fragment to the receptor molecule might be limiting; the affinity might not be sufficiently high to provide enough molecules of the Fab fragment on the cell surface to ensure efficient binding of the target cells to the stationary phase/chromatography. In addition, the chosen receptor molecule on the target cell might not have the chance to form clusters necessary for avidic binding onto the chromatographic resin due to the flow (the equilibrium of the binding of the Fab fragments to the receptor molecules might not be reached). In addition, the degree of immobilization on the stationary phase might differ for each type of Fab fragment and the chosen receptor molecule on the target cell surface. Thus, the purification efficiency might vary depending on the considered target cell population.

While the Streptamer®-technology or the method described in International Patent Application WO 2013/124474 work generally well, due to the disadvantages discussed above, there is however still the need for a method that, for example, allows the standardisation of the purification protocol for all types of considered target cells, i.e. also irrespective of the nature of the binding characteristics inherent to a biding pair consisting of a given receptor molecule and its receptor molecule binding reagent.

SUMMARY OF THE INVENTION

The present disclosure can be taken to generally relate to a solid phase technique or chromatographic technique for cell isolation. Provided herein are methods for the isolation of a desired biological entity such as a target cell, having a known receptor molecule on its surface. A method as disclosed herein may include the separation of such a cell from other cells void of such receptor on their surface. Generally a respective method provides a rapid, efficient and gentle isolation procedure enabling isolating complex cell populations such as regulatory T cells or central memory T-cells for research, diagnostic and especially therapeutic purposes. Where a biological cell or a population of biological cells is to be isolated, a method disclosed herein allows obtaining an enriched, isolated and/or purified target cell or target cell population that is essentially void of reagents used for purposes of enriching, isolating and/or purifying.

In a first aspect, the invention provides a method of isolating a target cell wherein the target cell has a receptor molecule on the target cell surface. This method comprises:
    contacting
    i) a receptor molecule binding reagent, the receptor molecule binding reagent comprising a binding site B and a binding partner C,
    wherein the binding site B comprised in the receptor molecule binding reagent is capable of specifically binding to the receptor molecule on the target cell surface, and
    wherein the binding partner C comprised in the receptor molecule binding reagent is capable of reversibly binding to a binding site Z on a multimerization reagent,
    ii) a (soluble) multimerization reagent,
    wherein the multimerization reagent comprises two or more binding sites Z capable of reversibly binding to the binding partner C comprised in the receptor molecule binding reagent,
    wherein the multimerization reagent further comprises a ligand binding partner LB, the ligand binding partner LB being capable of specifically binding a ligand L,
    and
    iii) a sample, the sample comprising the target cell,
    thereby allowing the receptor molecule binding reagent, the multimerization reagent and the target cell to form a multivalent binding complex comprising the target cell bound to two or more receptor molecule binding reagents that are bound to the multimerization reagent,
        contacting the multivalent binding complex of target cell, receptor molecule binding reagent and multimerization reagent with a solid phase, the solid phase comprising the ligand L,
    thereby allowing reversible immobilization of the target cell on the solid phase via the binding between the ligand L and the ligand binding partner LB, wherein immobilization of the target cell on the solid phase is reversible upon disruption of at least the binding between the binding partner C comprised in the receptor molecule binding reagent and the binding site Z of the multimerization reagent.

In a second aspect, the invention provides an alternative method of isolating a target cell wherein the target cell has a receptor molecule on the target cell surface. This method comprises:
    contacting
    (i) a receptor molecule binding reagent,
    the receptor molecule binding reagent comprising a binding site B and a binding partner C, wherein the binding site B comprised in the receptor molecule binding reagent is capable of specifically binding to the receptor molecule on the target cell surface,
    wherein the binding partner C comprised in the receptor molecule binding reagent is capable of reversibly binding to a binding site Z on a multimerization reagent, and wherein the receptor molecule binding reagent further comprises a ligand binding partner LB, the ligand binding partner LB being capable of specifically binding a ligand L, ii) a (soluble) multimerization reagent, wherein the multimerization reagent comprises two or more binding sites Z capable of reversibly binding to the binding partner C comprised in the receptor molecule binding reagent, and iii) a sample, the sample comprising the target cell, thereby allowing the receptor molecule binding reagent, the multimerization reagent and the target cell to form a multivalent binding complex comprising the target cell bound to two or more receptor molecule binding reagents that are bound to the multimerization reagent, contacting the multivalent binding complex of target cell, receptor molecule binding reagent and multimerization reagent with a solid phase, the solid phase comprising the ligand L, thereby allowing reversible immobilization of the target cell on the solid phase via the binding between the ligand L and the ligand binding partner LB, wherein immobilization of the target cell on the solid phase is reversible upon disruption of a) the binding between the binding partner C comprised in the receptor molecule binding reagent and the binding site Z of the multimerization reagent and/or b) the binding between the ligand L of the solid phase and the ligand binding partner LB comprised in the receptor molecule binding reagent.

As indicated above, in some embodiments of the method of the first or second aspect, the receptor molecule binding reagent, the soluble multimerization reagent and the sample containing the target cells are incubated together at the same time. In other embodiments the receptor molecule binding reagent and the multimerization reagent are contacted with each other to form a complex comprising two or more receptor molecule binding reagents bound to the multimerization reagent prior to contacting (incubating) this complex with the target cell.

In the method of the first or second aspect, the dissociation constant ($K_d$) for the binding between the receptor molecule binding reagent and the receptor molecule may be of low affinity, meaning the dissociation constant ($K_d$) for the binding between said receptor molecule binding reagent and said receptor molecule may be in the range of about $10^{-2}$ to about $10^{-7}$ M. In other embodiments of the invention, the binding between the receptor molecule binding reagent and the receptor molecule may be of high affinity, meaning the dissociation constant ($K_d$) for the binding between said receptor molecule binding reagent and said receptor molecule may be in the range of about $10^{-7}$ to about $10^{-10}$ M.

In some embodiments the method of the first or second aspect may further include contacting the stationary phase with a competition reagent. This competition reagent is capable of disrupting the binding between the binding partner C and the binding site Z. By contacting the stationary phase with this competition reagent the target cell is eluted from the stationary phase.

In a third aspect, the invention provides a method of immobilizing a target cell on a solid phase, wherein the target cell has a receptor molecule on the target cell surface. This method comprises:

contacting (i) a receptor molecule binding reagent, the receptor molecule binding reagent comprising a binding site B and a binding partner C, wherein the binding site B comprised in the receptor molecule binding reagent is capable of specifically binding to the receptor molecule on the target cell surface, and wherein the binding partner C comprised in the receptor molecule binding reagent is capable of reversibly binding to a binding site Z on a multimerization reagent, ii) a (soluble) multimerization reagent, wherein the multimerization reagent comprises two or more binding sites Z capable of reversibly binding to the binding partner C comprised in the receptor molecule binding reagent, wherein the multimerization reagent further comprises a ligand binding partner LB, the ligand binding partner LB being capable of specifically binding a ligand L, and iii) a sample, the sample comprising the target cell, thereby allowing the receptor molecule binding reagent, the multimerization reagent and the target cell to form a multivalent binding complex comprising the target cell bound to two or more receptor molecule binding reagents that are bound to the multimerization reagent, contacting the multivalent binding complex of target cell, receptor molecule binding reagent and multimerization reagent with a solid phase, the solid phase comprising the ligand L, thereby allowing reversible immobilization of the target cell on the solid phase via the binding between the ligand L and the ligand binding partner LB, wherein immobilization of the target cell on the solid phase is reversible upon disruption of at least the binding between the binding partner C comprised in the receptor molecule binding reagent and the binding site Z of the multimerization reagent.

In a fourth aspect, the invention provides an alternative method of immobilising a target cell on a solid phase, wherein the target cell has a receptor molecule on the target cell surface. This method comprises:

contacting i) a receptor molecule binding reagent, the receptor molecule binding reagent comprising a binding site B and a binding partner C, wherein the binding site B comprised in the receptor molecule binding reagent is capable of specifically binding to the receptor molecule on the target cell surface, wherein the binding partner C comprised in the receptor molecule binding reagent is capable of reversibly binding to a binding site Z on a multimerization reagent, and wherein the receptor molecule binding reagent further comprises a ligand binding partner LB, the ligand binding partner LB being capable of specifically binding a ligand L, ii) a (soluble) multimerization reagent, wherein the multimerization reagent comprises two or more binding sites Z capable of reversibly binding to the binding partner C comprised in the receptor molecule binding reagent, and iii) a sample, the sample comprising the target cell, thereby allowing the receptor molecule binding reagent, the multimerization reagent and the target cell to form a multivalent binding complex comprising the target cell bound to two or more receptor molecule binding reagents that are bound to the multimerization reagent, contacting the multivalent binding complex of target cell, receptor molecule binding reagent and multimerization reagent with a solid phase, the solid phase comprising the ligand L, thereby allowing reversible immobilization of the target cell on the solid phase via the binding between the ligand L and the ligand binding partner LB, wherein immobilization of the target cell on the solid phase is reversible upon disruption of
   a) the binding between the binding partner C comprised in the receptor molecule binding reagent and the binding site Z of the multimerization reagent and/or
   b) the binding between the ligand L of the solid phase and the ligand binding partner LB comprised in the receptor molecule binding reagent.

In a fifth aspect, the invention provides an arrangement for isolating a target cell from a sample. This arrangement comprises:
   a solid phase comprising a ligand L, wherein the ligand L is capable of specifically binding a ligand binding partner LB, the ligand binding partner LB being present in a receptor molecule binding reagent or a (soluble) multimerization reagent used for isolating the target cell, the ligand L thereby allowing reversible immobilization of the target cell on the solid phase,
   at least one of
   a) a first stationary phase, wherein the first stationary phase is suitable for cell separation, the first stationary phase being a gel filtration matrix and/or affinity chromatography matrix, wherein the matrix comprises an affinity reagent having a binding site Z specifically binding to a binding partner C comprised in the receptor molecule binding reagent, thereby allowing immobilization of the receptor molecule binding reagent on the first stationary phase and removal of the receptor molecule binding reagent from an eluate comprising the target cell,
   or
   b) a second stationary phase, wherein the second stationary phase comprises the ligand L, wherein the ligand L is capable of specifically binding to the ligand binding partner LB being present in the receptor molecule binding reagent or the multimerization reagent used for isolating the target cell, the ligand L thereby allowing immobilization of the receptor molecule binding reagent or the multimerization reagent on the second stationary phase and removal of the receptor molecule binding reagent or the multimerization reagent from an eluate comprising the target cell.

In a sixth aspect, the invention provides a device for isolating a target cell from a sample. This device comprises an arrangement for isolating a target cell from a sample according to the fifth aspect.

In a seventh aspect, the invention provides the use of a solid phase comprising a ligand L, wherein the ligand L is capable of specifically binding a ligand binding partner LB, for reversible immobilization or isolation of a target cell. The ligand may be biotin or a derivative of biotin. Examples of a suitable derivative of biotin including, but are not limited to, desthiobiotin, iminobiotin, 2-(4'-hydroxyazobenzene) benzoic acid (HABA) or a streptavidin binding peptide. This seventh aspect include the use of a solid phase comprising a ligand L, wherein the ligand L is capable of specifically binding a ligand binding partner LB in a method for isolating a target cell according to the first or second aspect or for immobilization of a target cell according to the third of fourth aspect of this invention.

BRIEF DESCRIPTION OF THE DRAWINGS

The figures illustrate embodiments of the isolation of a cell as presented herein. Without wishing to be bound by theory, the figures include conclusions with regard to the underlying separation mechanism. The conclusions are given for illustrative purposes only and merely serve in allowing a visualization of how the separation achievable can be envisaged on a molecular level.

FIG. 1 depicts an embodiment of a method of isolating a target cell (3) that has a receptor molecule (4) on the target cell surface. The target cell can be defined by the presence of at least one particular specific receptor molecule (4). A receptor molecule binding reagent (1) is provided. The receptor molecule binding reagent (1) has a binding site (B), which can specifically bind to the receptor molecule (4). The receptor molecule binding reagent (1) might be a (monovalent) antibody fragment such as a Fab fragment, meaning the binding site (B) might be an antigen binding site. The dissociation constant ($K_d$) for the binding between (the binding site B of) the receptor molecule binding reagent and the receptor molecule may be of low affinity as defined herein. The receptor molecule binding reagent (1) also includes a binding partner (C), which can reversibly bind to a binding site (Z) of a multimerization reagent (2). The binding partner (C) may, for example be an affinity tag or peptide, such as a streptavidin binding peptide. In more detail, the binding partner (C) may, for example, be a streptavidin-binding peptide such as the peptide Trp-Ser-His-Pro-Gln-Phe-Glu-Lys (SEQ ID NO: 3, also known as the "Strep-Tag®II") that is described in U.S. Pat. No. 5,506,121, for example, or streptavidin binding peptides having a sequential arrangement of two or more individual binding modules as described in International Patent Publication WO 02/077018 or U.S. Pat. No. 7,981,632. An illustrative example of such a sequential arrangement is the sequence Trp-Ser-His-Pro-Gln-Phe-Glu-Lys-(GlyGlyGly-Ser)$_2$-Gly-Gly-Ser-Ala-Trp-Ser-His-Pro-Gln-Phe-Glu-Lys (SEQ ID NO: 13, also known under its trademark name "Twin-Strep-Tag®"). The binding partner (C) can be fused or conjugated to the receptor molecule binding reagent. In the case of the receptor molecule binding reagent (1) being an Fab fragment, the binding partner C might be fused to the C-terminus of either the heavy or the light chain of the antibody fragment.

Figure 4:
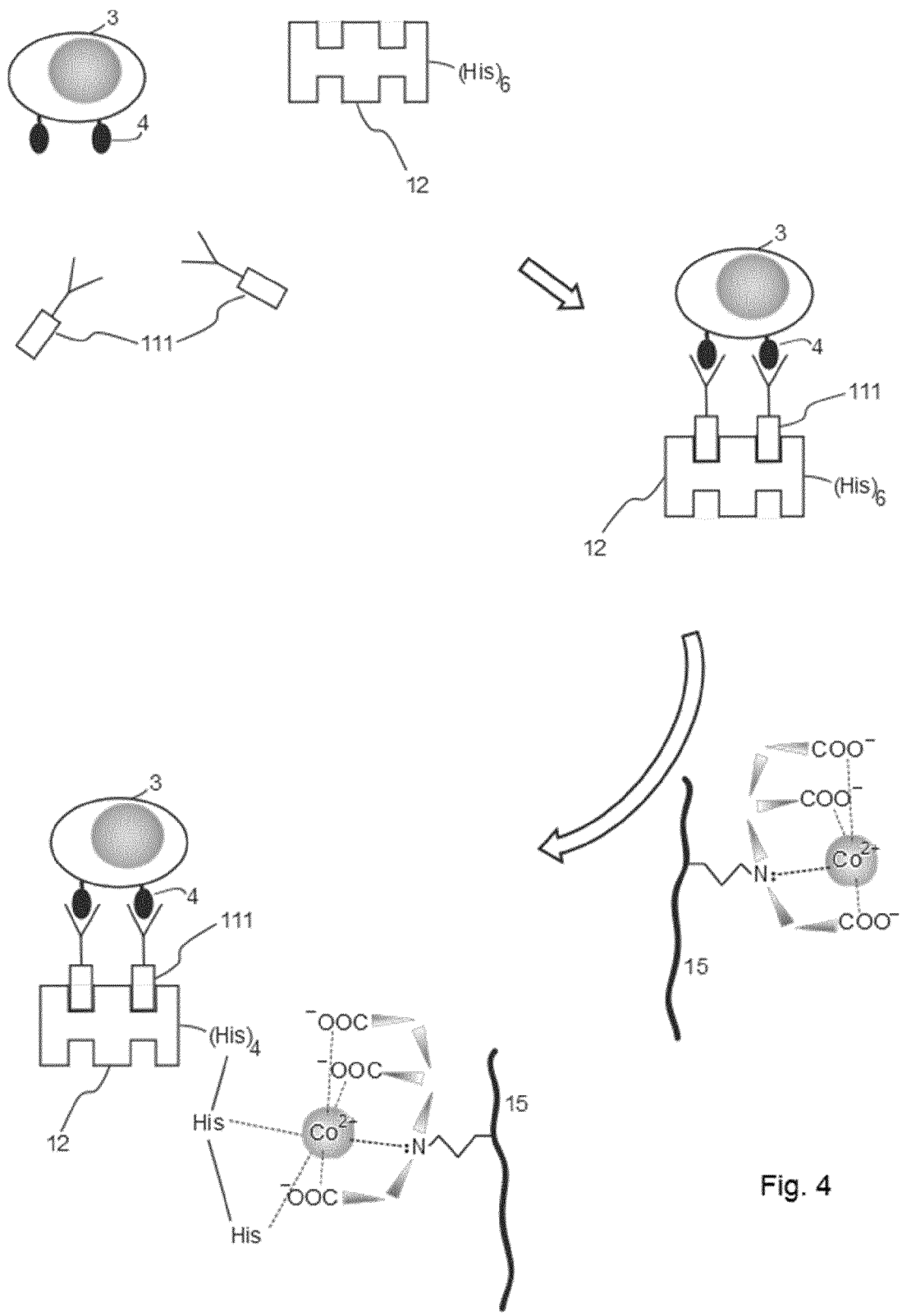

The soluble multimerization reagent (2) contains a plurality of binding sites Z, which are capable of reversibly binding to the binding partner (C). The receptor binding reagent (1) binds via the binding partner (C) to a binding site (Z) on the multimerization reagent (2). When the multimerization reagent (2) and a plurality of the receptor binding reagent (1) bind to each other they form a multivalent binding complex with respect to the binding site (B) of the receptor molecule binding reagent. As described, for example, in International Patent Application WO 02/054065 or U.S. Pat. No. 7,776,562, this multivalent binding complex thus provides an avidity effect compared to the binding of the (monovalent) receptor molecule binding reagent alone, thereby allowing using such low affinity monovalent receptor molecule binding reagents which in single form would not stably bind the target cell but would rapidly dissociate from the receptor molecule. The so multimerized receptor molecule binding reagent (1) contained in this multivalent complexes can later (see below) bind to the target cell (3). When using a streptavidin binding peptide as binding partner (C), the multimerization reagent (2) can be any streptavidin mutein to which the streptavidin peptide (=binding partner C1) reversibly binds via its (biotin) binding sites Z schematically shown in FIG. 1. Such a multimerization reagent may be a streptavidin mutein (analog) comprising the amino acid sequence Val$^{44}$-Thr$^{45}$-Ala$^{46}$-Arg$^{47}$ (SEQ ID NO: 19) at sequence positions 44 to 47 of wild-type streptavidin or a streptavidin mutein (analog) comprising the amino acid sequence Ile$^{44}$-Gly$^{45}$-Ala$^{46}$-Arg$^{47}$ (SEQ ID NO: 20) at sequence positions 44 to 47 of wild-type streptavidin. Such muteins are described in U.S. Pat. No. 6,103,493, for example, and are commercially available from IBA GmbH, Göttingen, Germany in the form of mutein "m1" and mutein "m2 under the trademark Strep-Tactin®.

The multimerization reagent (2) also includes a ligand binding partner (LB), which is capable of specifically binding a ligand (L). In the example shown in FIG. 1, the ligand binding partner (LB) may, for example, be a hexa-histidine tag or glutathione-S-transferase. In this case, the streptavidin mutein (monomer) can be recombinantly produced as a fusion protein with either a hexa-histidine tag or glutathione-S-transferase as fusion partner.

In the method of FIG. 1, a sample which includes the target cell (3) is then contacted with the multivalent binding complex, and the target cell (3) binds to the multivalent binding complex. A chromatography matrix (5) is provided as solid phase (stationary phase). The chromatography matrix (5) contains a ligand (L) to which the ligand binding partner (LB) binds, thereby immobilizing the target cell as a part of the target cell/multivalent binding complex on the stationary phase (5). In the example of FIG. 1, the ligand L may, for example, be chelating groups that have a transition metal complexed thereto and that are capable of binding to an oligohistidine peptide such as a hexa-histidine tag. The solid phase or stationary phase (5) might be an immobilized metal affinity chromatography (IMAC) resin such as the TALON® resin (Westburg, Leusden, The Netherlands). Alternatively, if glutathione-S-tranferase is used as ligand binding partner LB, the ligand L might be glutathione. In this case, the solid phase (5) may be a sepharose matrix, to which glutathione is coupled.

As a result of the binding of the ligand binding partner (LB) to the ligand L, the target cells (3) are immobilized on the solid phase and the sample is being depleted of the target cell (3). The target cell (3) is thus being separated from the other components in the sample. If wanted, the solid phase may then be washed with a suitable washing buffer (not shown in FIG. 1) Thereafter, a competition reagent (6) is contacted with the stationary phase (5). The competition reagent (6) may specifically bind to the ligand (L) and disrupt the binding between the ligand (L) and ligand binding partner (LB). In addition, the binding between the binding partner (C) of the receptor molecule binding reagent and the binding sites (Z) of the multimerization reagent (2) is disrupted. This may be achieved, for example, by a competition reagent (12) that binds to the binding site (Z) of the multimerization reagent, thereby displacing the binding partner C of the receptor molecule binding reagent (2) from the binding site (Z) of the multimerization reagent (2). Since in this example a low affinity receptor molecule binding reagent (1) is used, the receptor molecule binding reagent (1) dissociates from the receptor molecule (4) (not shown in FIG. 1). As a result, the target cell (3) is being released from the stationary phase (5) free of any reagents that are used for the isolation. In the example of the ligand L being chelating groups that have a transition metal complexed thereto and the ligand binding partner LB being an oligohistidine tag, the binding between the ligand L and the ligand binding partner LB may be disrupted by a metal chelator such as EDTA or EGTA. This example, shows that the competition reagent does not have to be a competitor as such but can be any compound that is able to disrupt the bond that is formed either between the ligand binding partner LB and the ligand L or between the binding partner C and the binding site Z of the multimerization reagent. In this example of FIG. 1, where the multimerization reagent (2) is a streptavidin mutein and the binding partner C is a streptavidin binding peptide, the respective competition reagent (12) may be any compound that binds to the biotin binding site of streptavidin, for example, a free streptavidin binding peptide or biotin or a biotin derivate such as iminobiotin or desthiobiotin. Likewise, the competition reagent can also be a shift in pH since the binding of streptavidin binding peptides to streptavidin can be disrupted by a low pH such as pH 4. In addition, it is noted here that for elution/isolation of the target cell (3) that is immobilized on the solid support as shown in FIG. 1, it is not necessary to disrupt the bond between the ligand binding partner LB and the ligand L. Rather, for the release of the target cells from the solid support, it is sufficient that the binding of the binding partner C of the receptor molecule binding reagent (1) to the binding site Z of the multimerization reagent is disrupted. It is noted in this context that accordingly the bond formed between the ligand binding partner LB and the ligand L does not even have to be reversible, it can also be irreversible and only serve for immobilization of the multimerization reagent (2) to which the target cells (3) are bound via the reversible bond formed between of the binding partner C of the receptor molecule binding reagent (1) to the binding site Z of the multimerization reagent. It may, however, be of advantage if the bond formed between the ligand binding partner LB and the ligand L is also reversible since this allows the regeneration of the solid phase. In this context, it is also noted that the ligand binding partner LB can also be contained in the receptor molecule binding reagent (1) instead of being included in the multimerization reagent (2). In this illustrative example of FIG. 1, where the multimerization reagent is a streptavidin mutein and the ligand L are chelating groups that have a transition metal complexed thereto and that are capable of binding an oligohistidine peptide, the receptor molecule binding reagent may be an antibody fragment such an Fab fragment which carries at the C-terminus of one of its two polypeptide chains (for example, the heavy chain) an streptavidin binding peptide as binding partner C (see above) and at the C-terminus of the other polypeptide chain (for example, the light chain) an hexahistidine tag that acts as ligand binding LB. In order to make sure that the hexahistidine tag is sterically accessible, the light chain of the Fab fragment might have as an extender" an artificial linker between the C-terminus of the constant domain and the hexahistidine tag. It is also noted in this context that the disruption of the two bonds, namely the bond between the multimerization reagent (2) and the binding partner C of the receptor molecule binding reagent (1) and the bond between the ligand L of the solid phase and the ligand binding partner LB of the multimerisation reagent can be conveniently achieved simultaneously by addition of a buffer that contains both biotin and EDTA as competition reagents. The biotin will displace the binding partner C (the streptavidin binding peptide) from the multimerisation reagent, EDTA as a metal chelator will complex the metal ion that mediated the binding of hexahistidine tag to the ligand L, thereby releasing the hexahistidine tag and thus the receptor molecule binding reagent from the solid phase FIG. 2 depicts a further embodiment of a method of isolating a target cell (3) with receptor molecules (4) on the target cell surface. A receptor molecule binding reagent (1) is provided, which has a binding site (B) that is able to specifically bind to the receptor molecule (4). The receptor molecule binding reagent (1) also includes a binding partner (C), which can reversibly bind to a binding site (Z) of a soluble multimerization reagent (2). The multimerization reagent (2) has a plurality of binding sites (Z), which specifically bind to the binding partner (C) that is included in the receptor binding reagent (1). A multivalent binding complex is formed which can bind to the target cell (3). The binding site (Z) of the multimerization reagent (2) also defines the ligand binding partner (LB), which is capable of binding a ligand (L) that is comprised in the solid phase. Thus, in the example of FIG. 2, the ligand binding partner LB is identical to the binding site Z. The sample with the target cell (3) is contacted with the multivalent binding complex, and the target cell (3) binds to the binding complex. A solid phase (5) such as a stationary phase for chromatography or a bead is provided, which contains a ligand (L), which can bind to the binding site (Z) that also defines the ligand binding partner (LB). As a result free binding sites (Z) on the multimerization reagent (2) bind to the ligand (L), thereby immobilizing the target cell as a part of the target cell/multivalent binding complex on the stationary phase (5). The sample is thereby being depleted of the target cell (3) and the target cell (3) being separated from the other components of the sample.

In the example of the method of the invention illustrated in FIG. 2 the receptor molecule binding reagent (1) may again be an antibody fragment such as a Fab fragment that exhibits a low affinity binding of its binding site (B) to the receptor molecule (4). The binding partner C of the receptor molecule binding reagent may be a streptavidin binding peptide. For example, the binding partner C can be a streptavidin binding peptide of the sequences Trp-Ser-His-Pro-Gln-Phe-Glu-Lys (SEQ ID NO: 3, the "Strep-Tag®"), of the sequence Trp-Ser-His-Pro-Gln-Phe-Glu-Lys-(GlyGlyGlySer)$_3$-Trp-Ser-His-Pro-Gln-Phe-Glu-Lys (SEQ ID NO: 11, also known as "di-tag3") or of the sequence Trp-Ser-His-Pro-Gln-Phe-Glu-Lys-(GlyGlyGlySer)$_2$-Trp-Ser-His-Pro-Gln-Phe-Glu-Lys (SEQ ID NO: 12, also known as "the di-tag2"), described by Junttila et al., Proteomics 5 (2005), 1199-1203 or U.S. Pat. No. 7,981,632). Such recombinant Fab fragments that bind cell surface receptors such as CD3, CD4, CD8 (T cell markers), CD8, CD62L, CD45RA (marker for memory T cells), CD4, CD25, CD45RA (markers for regulatory T cells), CD56 (marker for natural killer cells), CD19 (B cell marker) and CD34 (stem cell marker), are for example, commercially available as "Streptamer®" reagents from IBA GmbH (Göttingen, Germany) and can thus be used as receptor binding molecules for isolating the respective cells using the method of the invention. All the streptavidin binding peptides mentioned here bind to the same binding site, namely the biotin binding site of streptavidin. If one or more of such streptavidin binding peptides is used as binding partner C the multimerization reagent (2) is a streptavidin mutein such as the streptavidin mutein "m1" that comprises the amino acid sequence Val$^{44}$-Thr$^{45}$-Ala$^{46}$-Arg$^{47}$ (SEQ ID NO: 19) at sequence positions 44 to 47 of wild-type streptavidin or the streptavidin mutein (analog) "m2" that comprises the amino acid sequence Ile$^{44}$-Gly$^{45}$-Ala$^{46}$-Arg$^{47}$ (SEQ ID NO: 20) at sequence positions 44 to 47 of wild-type streptavidin. Typically, a soluble multimerization reagent (2) is used. In the case of a streptavidin mutein, this soluble multimerization reagent may, for example, be an oligomer or a polymer of streptavidin or avidin or of any mutein (analog) of streptavidin or avidin. Such a multimerization reagent is, for example, commercially available from IBA GmbH, Göttingen, Germany as "Strep-Tactin® PE for Fab Streptamers" (catalogue number 6-5001-010 or 6-5011-010). The oligomer may comprise three or more tetramers of streptavidin, avidin or a mutein thereof. The oligomer or polymer may be crosslinked by a polysaccharide. Such oligomers or polymers of streptavidin or avidin or of muteins of streptavidin or of avidin can in a first step be prepared by the introduction of carboxyl residues into a polysaccharide, e.g. dextran, essentially as described in "Noguchi, A., Takahashi, T., Yamaguchi, T., Kitamura, K., Takakura, Y., Hashida, M. & Sezaki, H. (1992). Preparation and properties of the immunoconjugate composed of anti-human colon cancer monoclonal antibody and mitomycin C dextran conjugate. Bioconjugate Chemistry 3, 132-137". In a second step, streptavidin or avidin or muteins thereof are coupled via primary amino groups of internal lysine residue and/or the free N-terminus to the carboxyl groups in the dextran backbone using conventional carbodiimide chemistry. Alternatively, suitable cross-linked oligomers or polymers of streptavidin or avidin or of any mutein of streptavidin or avidin may also be obtained by crosslinking via bifunctional linkers such as glutardialdehyde or by other methods described in the literature. It is also possible to obtain oligomers or polymers of streptavidin by "click chemistry", for example, by an 1,3-dipolar cycloaddition between an azide and a terminal alkyne group. For this purpose, azide and alkyne groups, respectively, can be introduced into streptavidin or a streptavidin mutein by commercially available reagents such as azide succinimidyl ester (available from Life Technologies, catalogue number A10280) and alkyne succinimidyl ester (available from Life Technologies, catalogue number A10279). Streptavidin or the streptavidin mutein that carries the azide group is then reacted with usually the stochiometric molar amount of streptavidin or streptavidin mutein that carries the alkyne group to yield the oligomeric (i.e. with 3 or more individual streptavidin tetramers) or polymeric multimerization reagent.

In the example of FIG. 2, the ligand L of the solid phase can, for example, be biotin that is covalently attached to the solid phase. The biotin of the solid phase binds to free binding sites (Z) of the multimerization reagent (2), thereby immobilizing the target cells as a part of the target cell/multivalent binding complex on the stationary phase (5). Such a solid phase may, for example, be (d)-biotin Sepharose™ obtainable from Affiland S.A. (Ans-Liege, Belgium), Biotin-agarose obtainable from IBA GmbH, Göttingen, Germany or Superflow® agarose with covalently bound biotin that is obtained using the experimental protocol described here in the Experimental Section. In this example, the ligand L of the solid phase may alternatively be a derivative of biotin such as desthiobiotin, iminobiotin, 2-(4'-hydroxyazobenzene) benzoic acid (HABA) or a streptavidin binding peptide.

The stationary phase (5) is then contacted with a competition reagent (7). The competition reagent (7) may as such be able to bind (as a whole) to the binding site (Z) of the multimerization reagent (2). Alternatively, the competition reagent (7) may have a binding site (8) that binds to the binding site (C) of the receptor molecule binding reagent (1). By competitive binding of the competition reagent (7) to the multimerization reagent (2), the competition reagent disrupts, for example, by displacement, the binding between the binding site C of the receptor molecule binding reagent (1) and the binding sites (Z) of the multimerization reagent (2). As explained above, the ligand L of the solid phase also binds to binding sites (Z) of the multimerization reagent (2). Thus, the competition reagent also displaces bound ligand L from the multimerization reagent (2). By so doing, the multimerization reagent (2) is being released from the solid phase (5). Since the target cell (3) was bound to the multimerized receptor molecule binding reagent (1), the target cell (3) is also being released from the solid phase (stationary phase) (5) and does, for example, elute from a column in which the stationary phase (5) is a chromatography matrix. In this example of FIG. 2, the competition reagent (7) might be biotin, which binds "as a whole" to the binding sites (Z) of the multimerization reagent (2). The free biotin will thus (competitively) displace in the multimerization reagent (2) the biotin that is covalently coupled to the solid phase (5) and acts as ligand L as well as Fab fragments that act as receptor molecule binding reagent and that carry a streptavidin binding peptide. Thus, in case the solid phase (5) is a chromatography material, after contacting the immobilized target cells (3) with free biotin, the resulting eluate contains the isolated target cells (3), free receptor molecule binding reagent (1), the (soluble) streptavidin multimerization reagent (2) as well as free biotin. Thus, the isolation mixture contains the same reagents as the eluate of the "selection cartridge described in International patent application WO 2013/124474. This means, if the solid phase (5) is a stationary phase (5) for chromatography, the method of the present invention can replace the method of isolating a target cell as practiced on the "selection cartridge" of International patent application WO 2013/124474. Consequently, the method of the invention when implemented in column chromatography can replace the "selection cartridge" of International patent application WO 2013/124474. In addition, the reagents of the eluate of such a chromatography column can be removed via a "removal cartridge" as described in International patent application WO 2013/124474. In this context, it is noted that the solid phases such as biotin-Sepharose™ can be obtained in sterile form. Accordingly, using sterile biotin-Sepharose™ containing cartridges, the method of the invention can be easily implemented in an automated, closed system for isolation of cells under GMP conditions. Thus, the present invention provides a simple and yet elegant approach to obtain target cells of interest, for example, T cells or B cells for cell based therapy. In this context, it is also noted that the invention provides the added advantages that the same (standardized) multimerisation reagent can be used for the isolation of any desired cell type. Since the multimerization reagent can be used together with the same solid phase (such as biotin-Sepharose™) it is possible to always use the same multimerization reagent such as an oligomeric streptavidin mutein that offers a) sufficient free binding sites Z for immobilization on the solid phase and b) the same defined (excess) number of free binding sites Z for the formation of multivalent complexes of the receptor molecule binding reagent. Thus, the invention allows ensuring that regardless of the specific receptor molecule binding reagent that is used for isolation of a particular cell type, a sufficient numbers of binding sites Z are offered for the formation of multivalent binding complexes. In addition, it is a further advantage of the method of the invention that the target cells are incubated with the multimerization reagent and the receptor molecule binding reagent prior to immobilization of the cells on the solid phase. This incubation for the formation of multivalent complexes that contain the bound cells can be carried out a) in a defined small volume, thereby increasing the concentration of the formed complexes and b) in a defined amount of time, again independent of the cell type to be isolated. Thus, the present invention provides the possibility to standardize the isolation of target cells, independent of the nature of the target cells.

FIG. 3 shows an embodiment of a method of separating/isolating a target cell, in which the receptor molecule binding reagent (1) is formed from two or more reagents or subunits. An adapter reagent (9) and a receptor molecule binding pre-reagent (100) are being contacted with each other. The receptor molecule binding pre-reagent (100) has a binding site (11) for a binding portion (10) included in the adapter reagent (9). The adapter reagent (9) and the receptor binding pre-reagent (100) bind to each other via the binding site (11) and the binding portion (10). The receptor binding reagent (1) thus formed has a binding site (B), which may have been included in the receptor binding pre-reagent (100). The receptor binding reagent (1) also includes a binding partner (C), which can specifically and reversibly bind to a binding site (Z) of a multimerization reagent (2). The binding partner (C) may have been included in the adapter reagent (9). The method may then be carried out as depicted in FIG. 1. A multimerization reagent (2) may be added, which contains a plurality of binding sites (Z), capable of binding to the binding partner (C). The multimerization reagent (2) also includes a ligand binding partner (LB), which is capable of specifically binding a ligand (L). Via the binding partner (C) the receptor molecule binding reagent (1) binds to a binding site (Z) on the multimerization reagent (2). A multivalent binding complex is formed, which can bind to the target cell (3). If a sample containing the target cell (3) is contacted with the multivalent binding complex, the target cell (3) binds to the multivalent binding complex. A stationary phase (5) is provided, which contains a ligand (L) to which the ligand binding partner (LB) binds. As a result the target cell/multivalent binding complex is being immobilized on the stationary phase (5). A competition reagent (6) is added, which specifically binds to the ligand (L). Thereby the binding between the ligand (L) and ligand binding partner (LB) is disrupted and the target cell/multivalent binding complex is being released from the stationary phase (5).

FIG. 4 further illustrates an embodiment of a method of separating/isolating a target cell, in which the receptor molecule binding reagent is a Fab fragment (111), carrying a streptavidin binding peptide as mentioned in the example of FIG. 2, for example. The Fab molecule binds a receptor molecule on the target cell surface, for example a cell surface receptor such as CD3 or CD8 that is present on T cells. The multimerization reagent is a multimeric streptavidin mutein (12), e.g. an oligomer of the streptavidin mutein "m1" that comprises the amino acid sequence $Val^{44}$-$Thr^{45}$-$Ala^{46}$-$Arg^{47}$ (SEQ ID NO: 19) at sequence positions 44 to 47 of wild-type streptavidin or an oligomer of the streptavidin mutein "m2" that comprises the amino acid sequence $Ile^{44}$-$Gly^{45}$-$Ala^{46}$-$Arg^{47}$ (SEQ ID NO: 20) at sequence positions 44 to 47 of wild-type streptavidin. This oligomer may be formed by chemically coupling a plurality of the molecules of the streptavidin mutein. This multimeric streptavidin mutein (12) contains a plurality of binding sites Z for the streptavidin binding peptide of the Fab-fragment (111). The multimeric streptavidin mutein (12) also contains a 6×His-tag, which can bind to a metal affinity matrix such as Ni Sepharose™, NTA-agarose, His60 Ni, HisPur resin, or TALON resin, to mention only a few commercially available solid phases. If the Fab fragment (111) carrying the streptavidin binding peptide, the multimeric streptavidin mutein (12) and a target cell with a receptor molecule on the target cell surface are being contacted, a target cell/multivalent binding complex is formed. If this target cell/multivalent binding complex is contacted with a stationary phase that includes immobilized metal ions, the complex, and thereby the target cell, is being immobilized on the stationary phase. The target cell can then be eluted by adding, for instance, biotin and EDTA or imidazole.

Figure 5D:
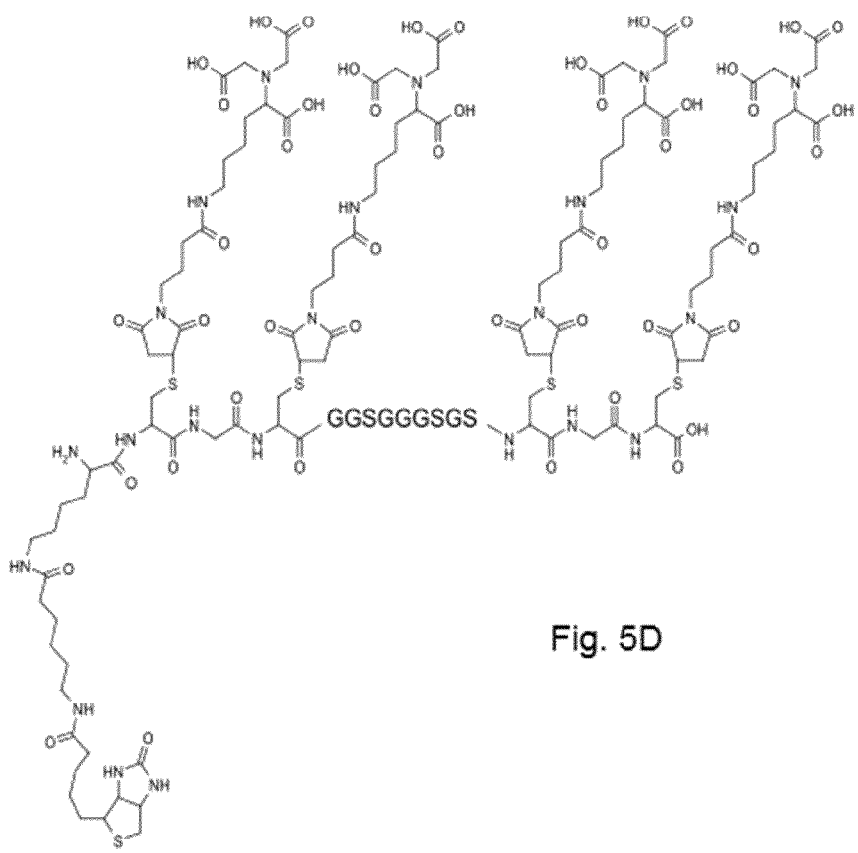
Figure 6A:
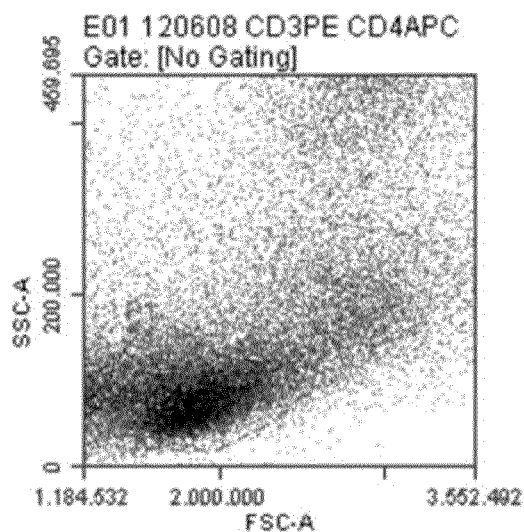
Figure 6B:
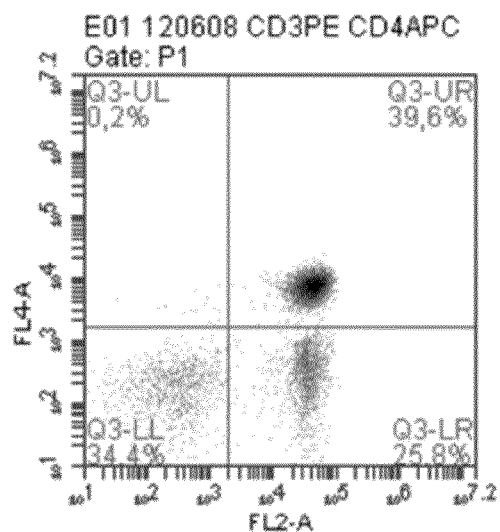
Figure 6C:
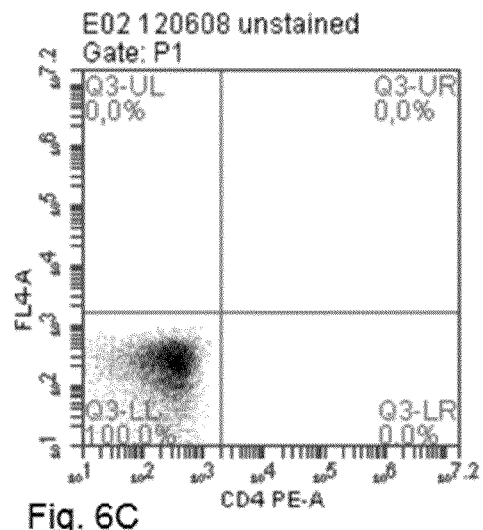
Figure 6D:
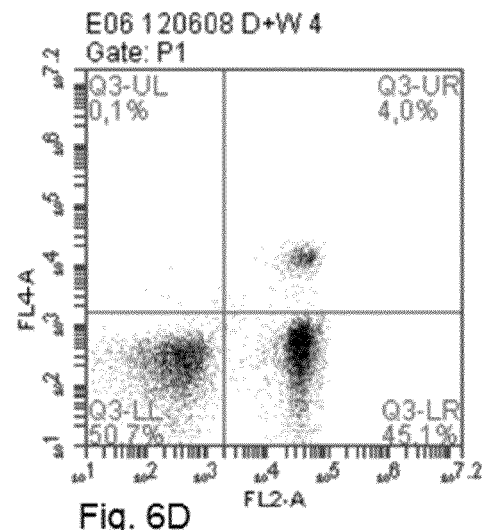
Figure 6E:
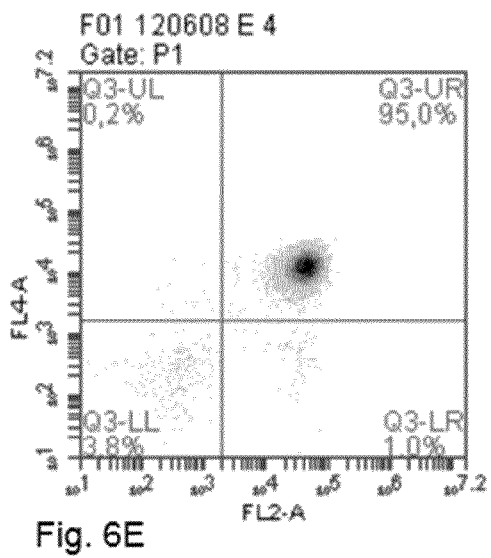
Figure 6F:
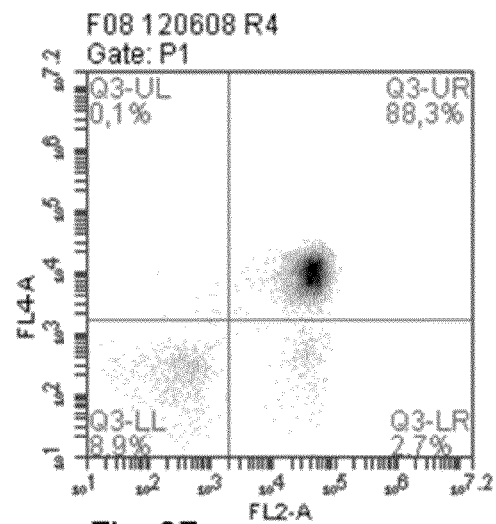

FIG. 5 depicts suitable moieties that allow the assembly of multimerization reagents that are able to bind to oligohistidine tags. The moieties shown in FIG. 5A to FIG. 5D are taken from Schmidt, J. et al., J. Biol. Chem. [2011] 286, 48, 41723-41735). These compounds contain biotin and a plurality of nitrilotriacetic acid (NTA) moieties that are capable of binding an oligohistidine tag. A multimerization agent is obtained by reacting any of these reagents with streptavidin. Since streptavidin is a homotetramer that thus provides four binding sites for biotin and biotin binds irreversibly to streptavidin, the reaction of these biotinylated compounds generates a reagent that carries a plurality (4 to 16) chelating groups K, wherein each chelating group K is capable of binding to a transition metal ion such as $Ni^{2+}$, or $Co^{2+}$, thereby rendering the multimerization reagent capable of binding to an oligohistidine peptide. Thus, when the chelating groups of the moieties in FIG. 5 are complexed with such transition metal, the multimerization reagent can form multivalent complexes with receptor molecule binding reagents that carry an oligohistidine tag. As described by Schmidt et al. (2011, supra), the receptor molecule binding reagents may, for example be, soluble major histocompatibilty complex (MHC) peptides which have fused an oligohistidine tag to their N-terminus. As a purely illustrative example, such an MHC peptide may be an HLA-A 0201-peptide containing a His-6 tag, a His-12tag or a 2_His-6 tag as described by Schmidt et al. (2011, supra). Such receptor binding reagents are also called "Histamers" and are commercially available from TC Metrix SA, Epalinges, Switzerland together with the multimerization reagents described here which use multimeric nitrilotriacetic acid (NTA) moieties as binding sites Z.

FIG. 6 shows the results of an experiment for enriching CD4+ cells from peripheral blood. Multimeric Strep-Tactin® was used as the multimerization reagent and an anti CD4 Fab fragment carrying a streptavidin-binding peptide was used as the receptor molecule binding reagent. CD4+ leukocytes from human blood served as exemplary target cells. The stationary phase contained biotin as a ligand L. Cells were characterized by flow cytometric analysis using Fluorescence-Activated Cell Sorting (FACS). FIG. 6A depicts a plot (Accuri C6 Flow Cytometer) of total cells (no gating). Cells were stained for CD3-PE and CD4-APC. FIG. 6B depicts a plot of total cells (gate P1). Cells were stained for CD3-PE and CD4-APC. FIG. 6C depicts a plot of total cells (gate P1). Cells were left unstained. FIG. 6D depicts a plot of cells of the fraction D+W (gate P1). Cells were stained for CD3-PE and CD4-APC. FIG. 6E depicts a plot of the fraction E (gate P1). Cells were stained for CD3-PE and CD4-APC. FIG. 6F depicts a plot of cells of the fraction R (gate P1). Cells were stained for CD3-PE and CD4-APC.

FIG. 7 shows a table summarizing the results of the FACS analysis depicted in FIG. 6. Analysis of total cells revealed a concentration of 39.56% CD4+ cells within the population of gated lymphocytes. Cells in the flow through and washing fractions were depleted to a concentration of 4.01% CD4+ cells. Elution by biotin revealed a purity of 95.04% of CD4+ cells. After pipette treatment of the column resin, physically eluted cells still showed a purity of 88.26%.

Figure 8A:
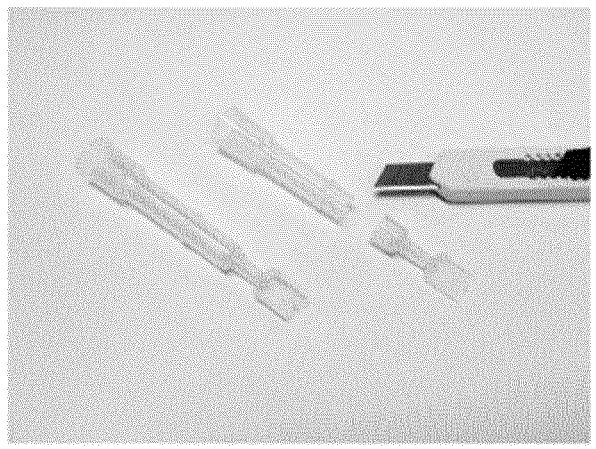
Figure 8B:
Figure 8C:
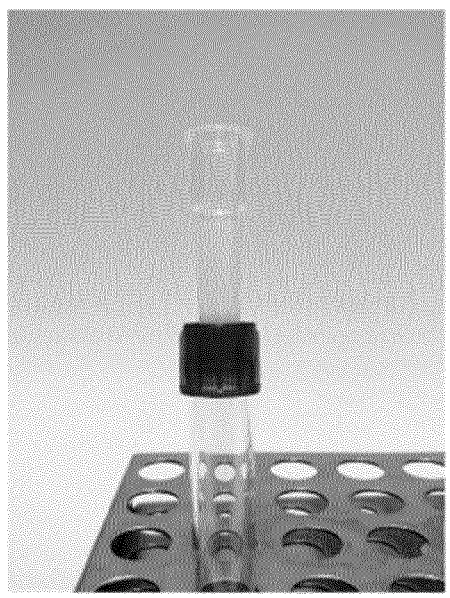
Figure 9A:
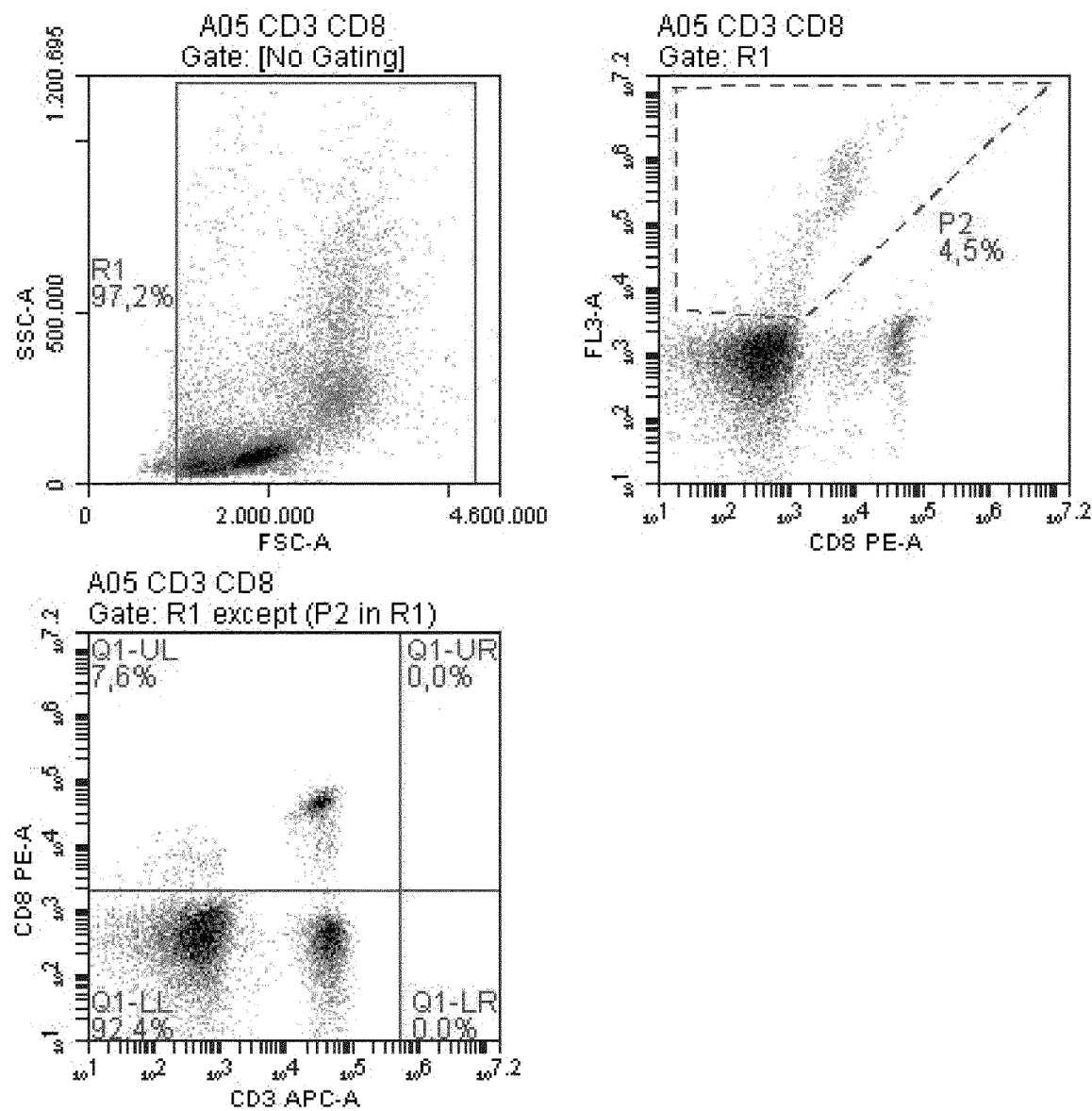
Figure 9A:
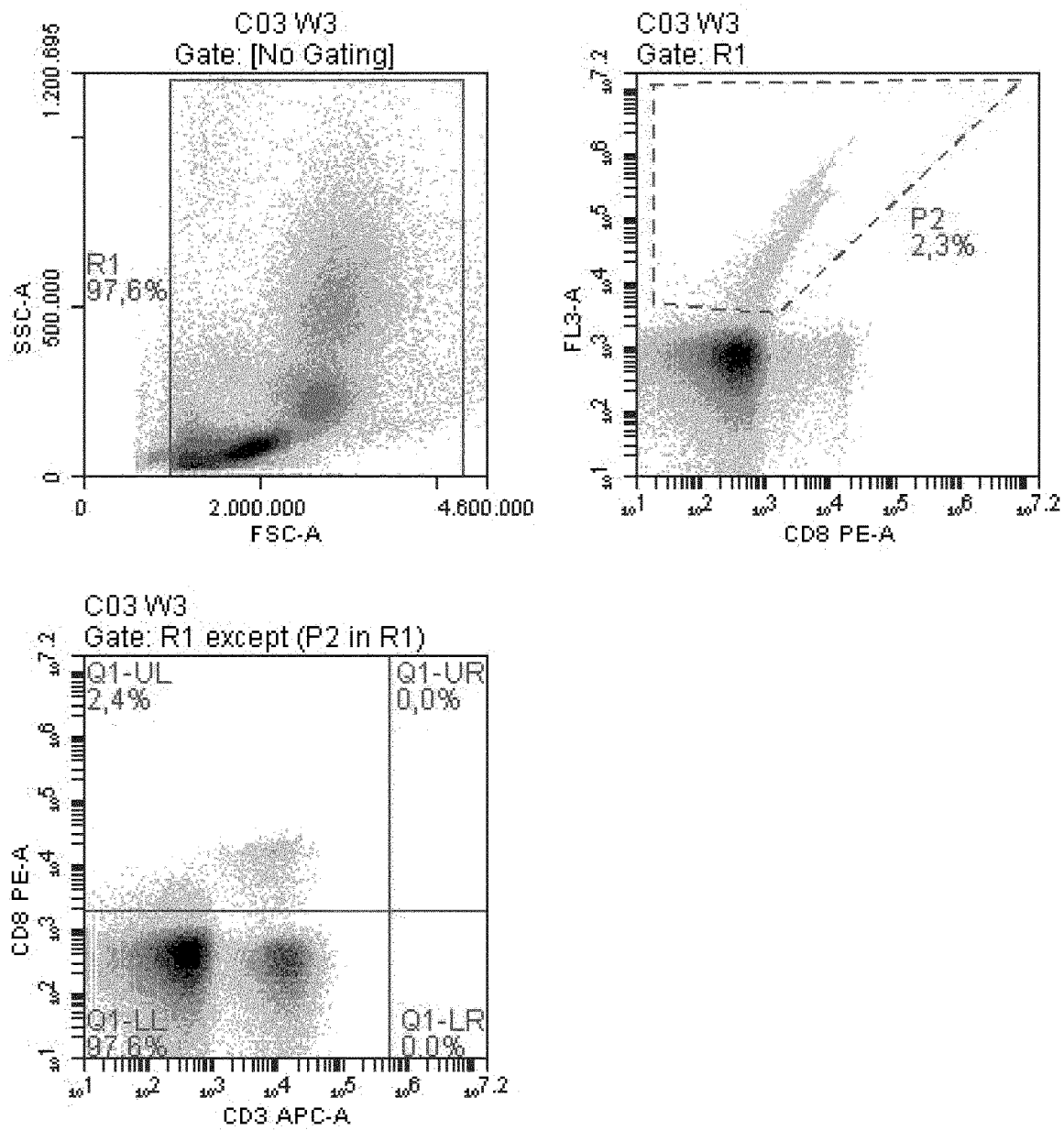
Figure 9A:
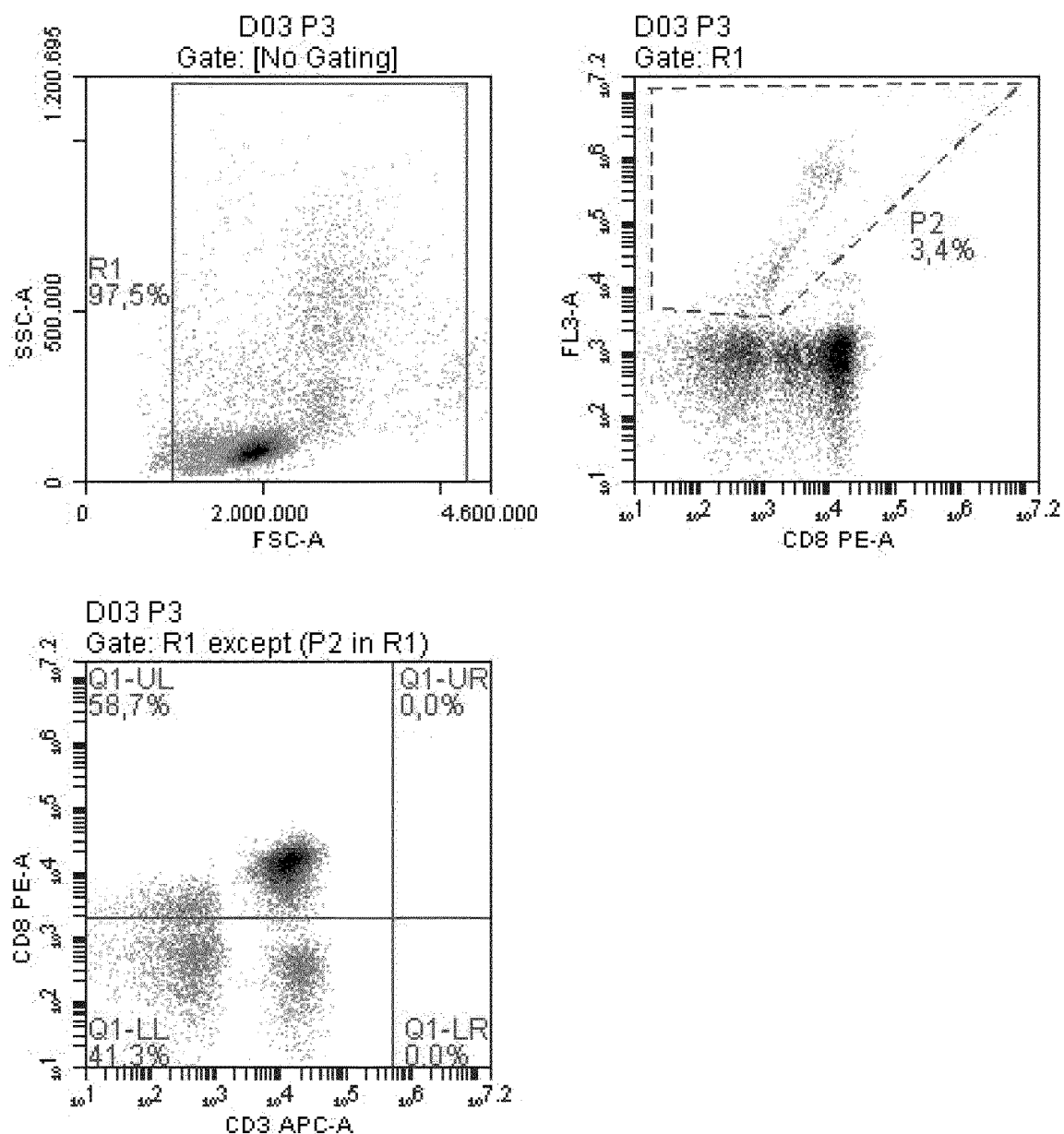
Figure 9B:
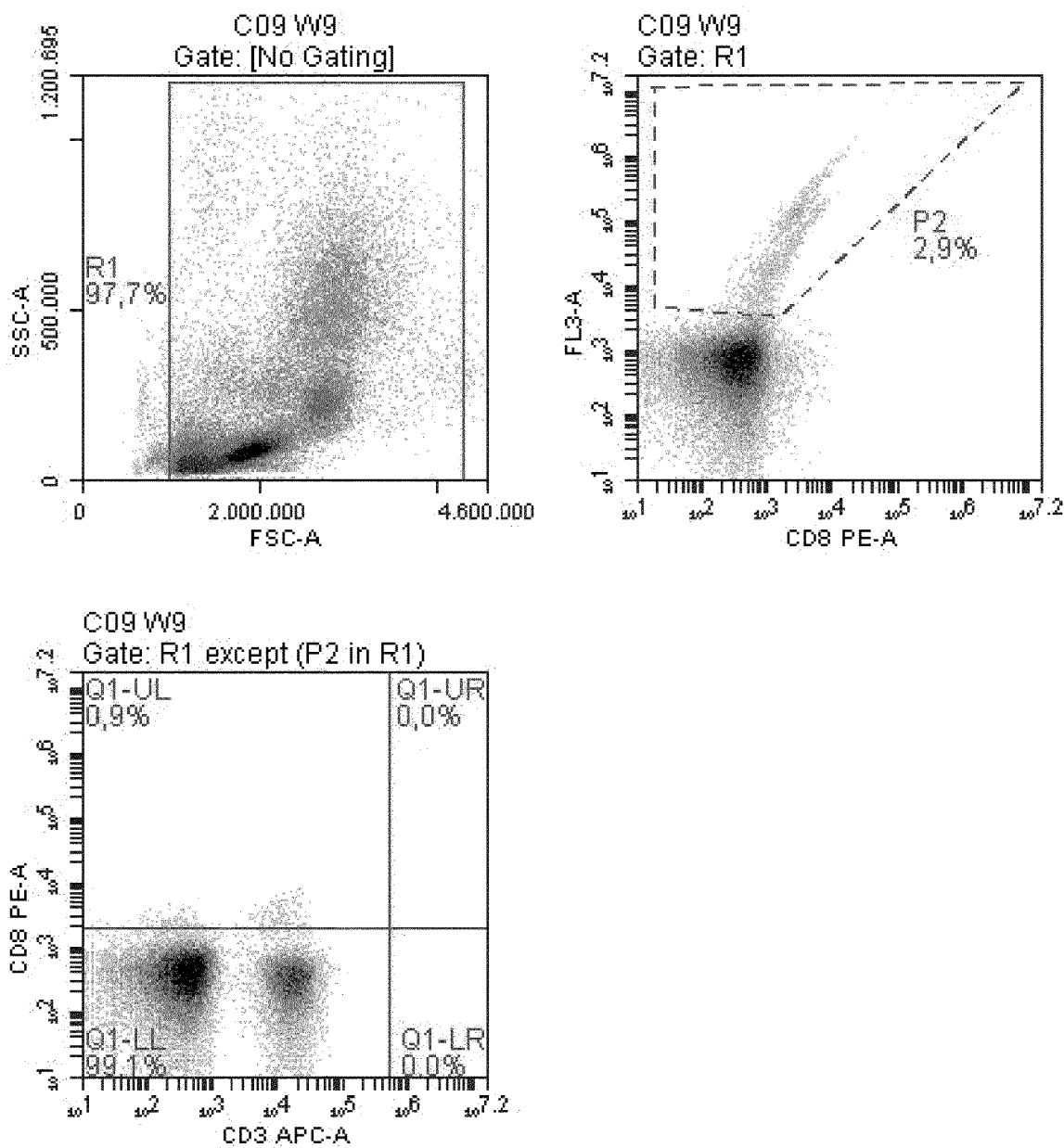
Figure 9B:
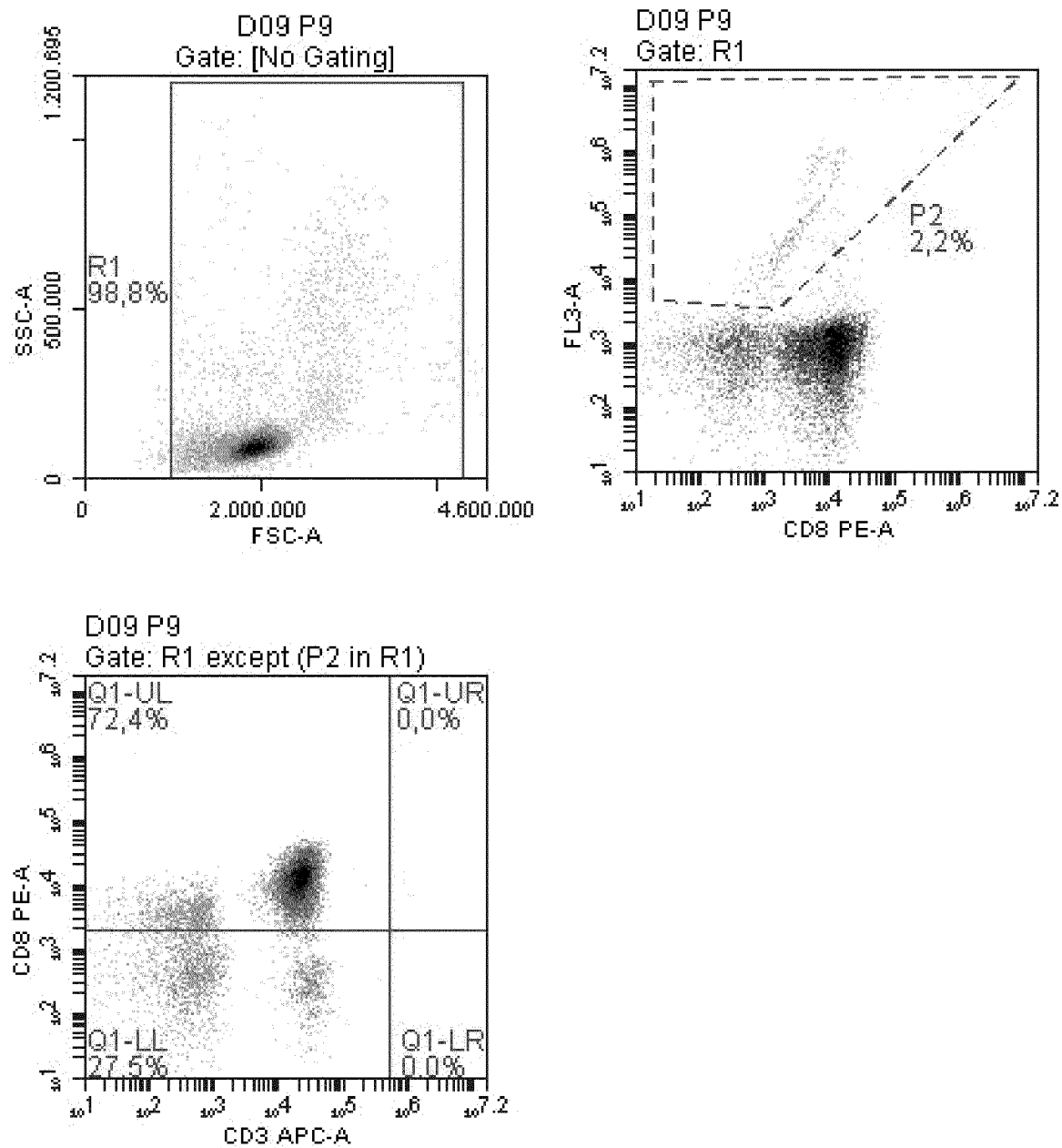
Figure 9C:
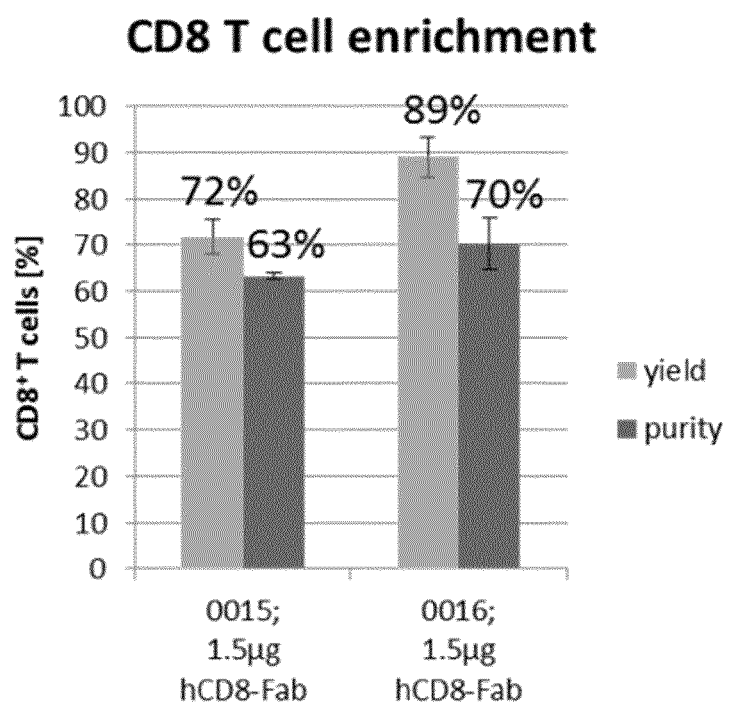
Figure 10A:
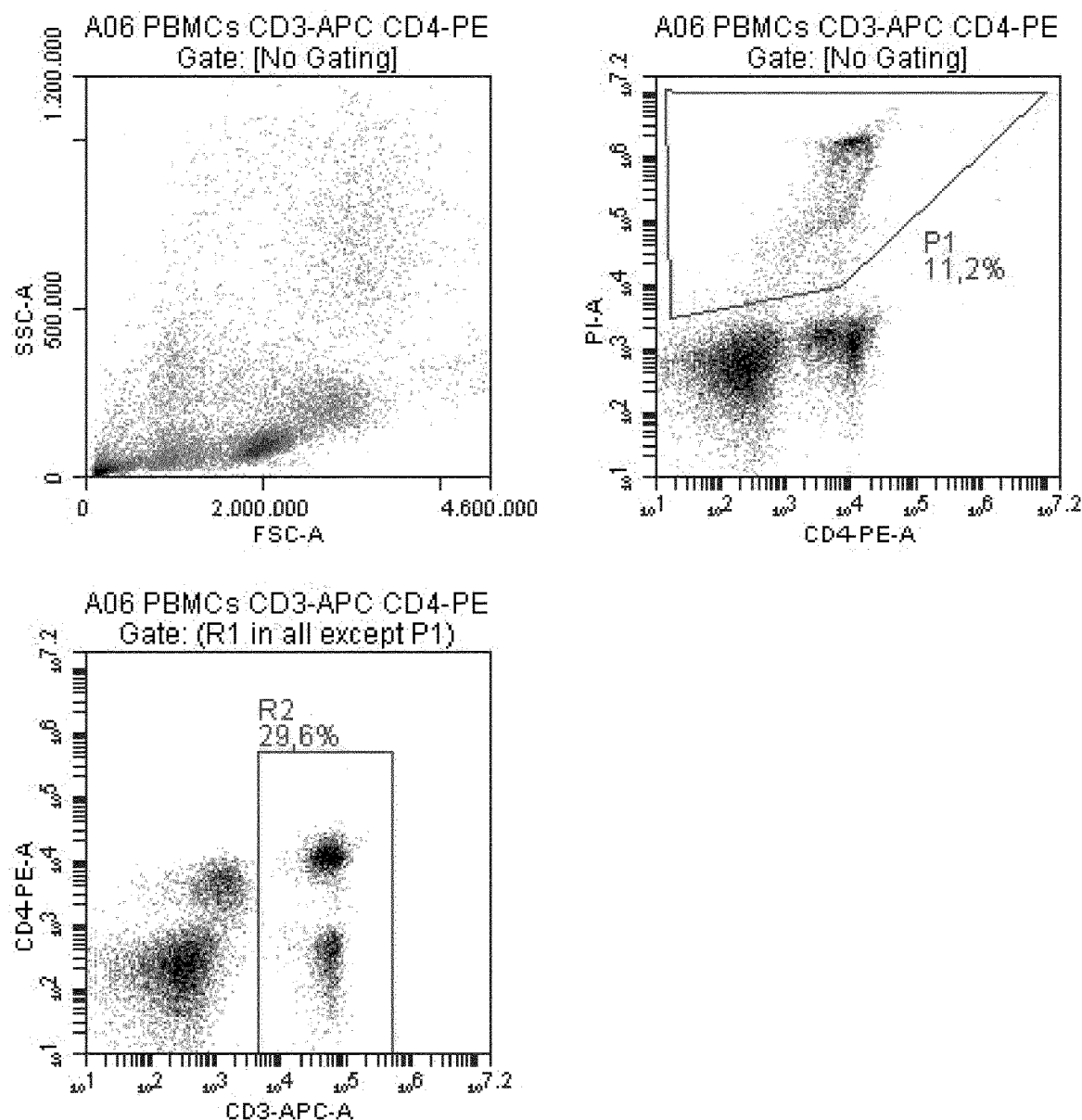
Figure 10A:
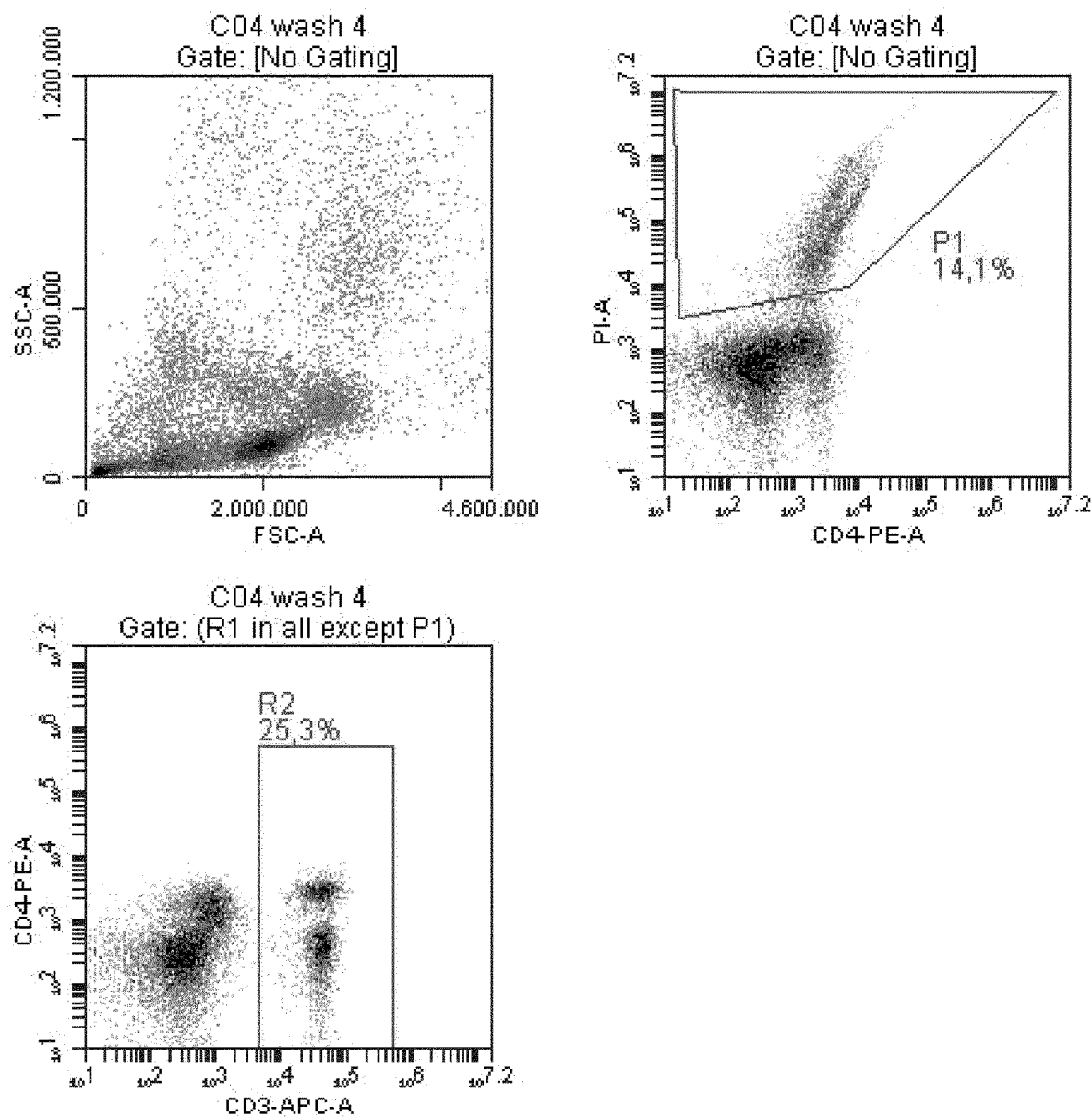
Figure 10A:
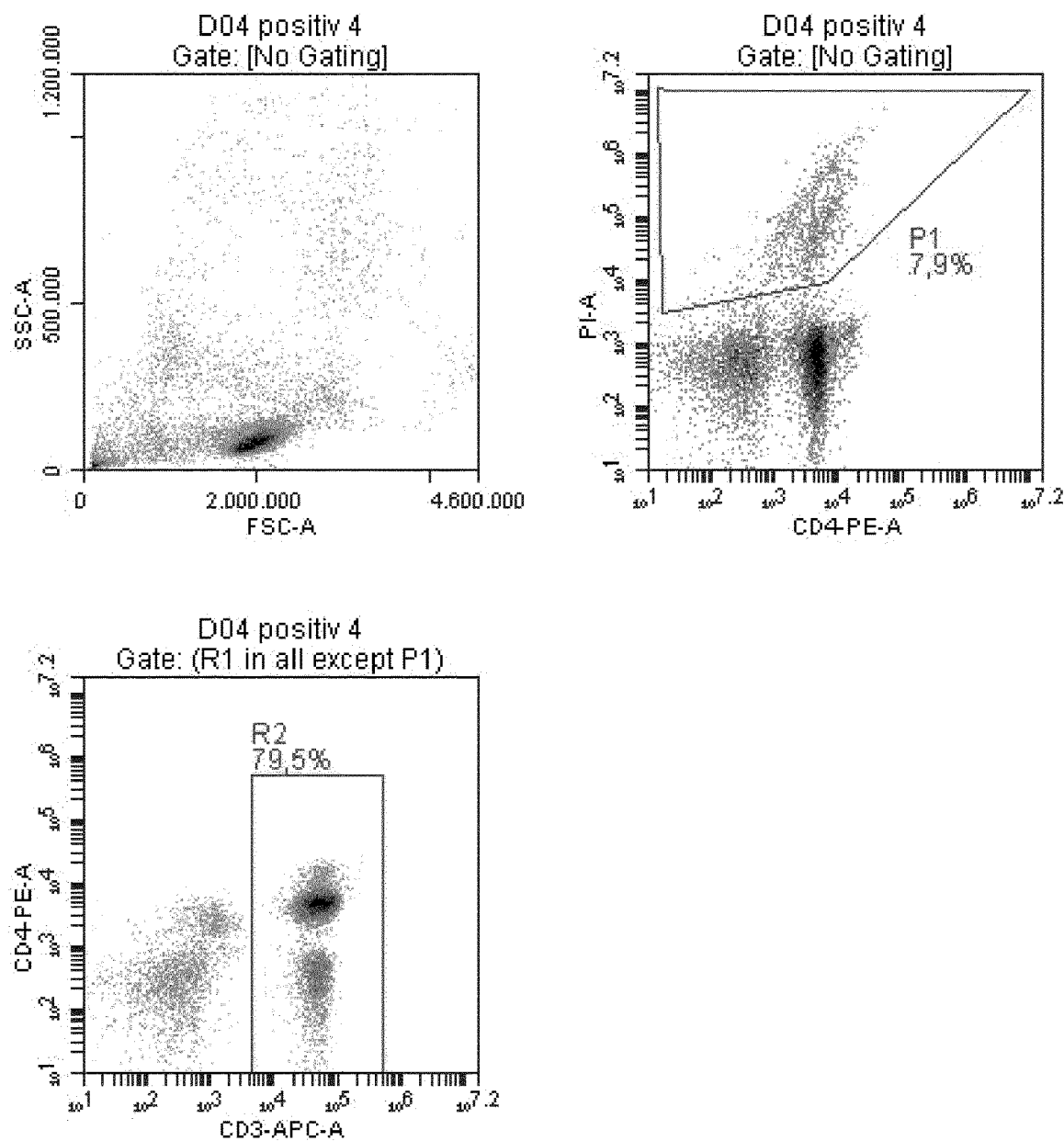
Figure 10B:
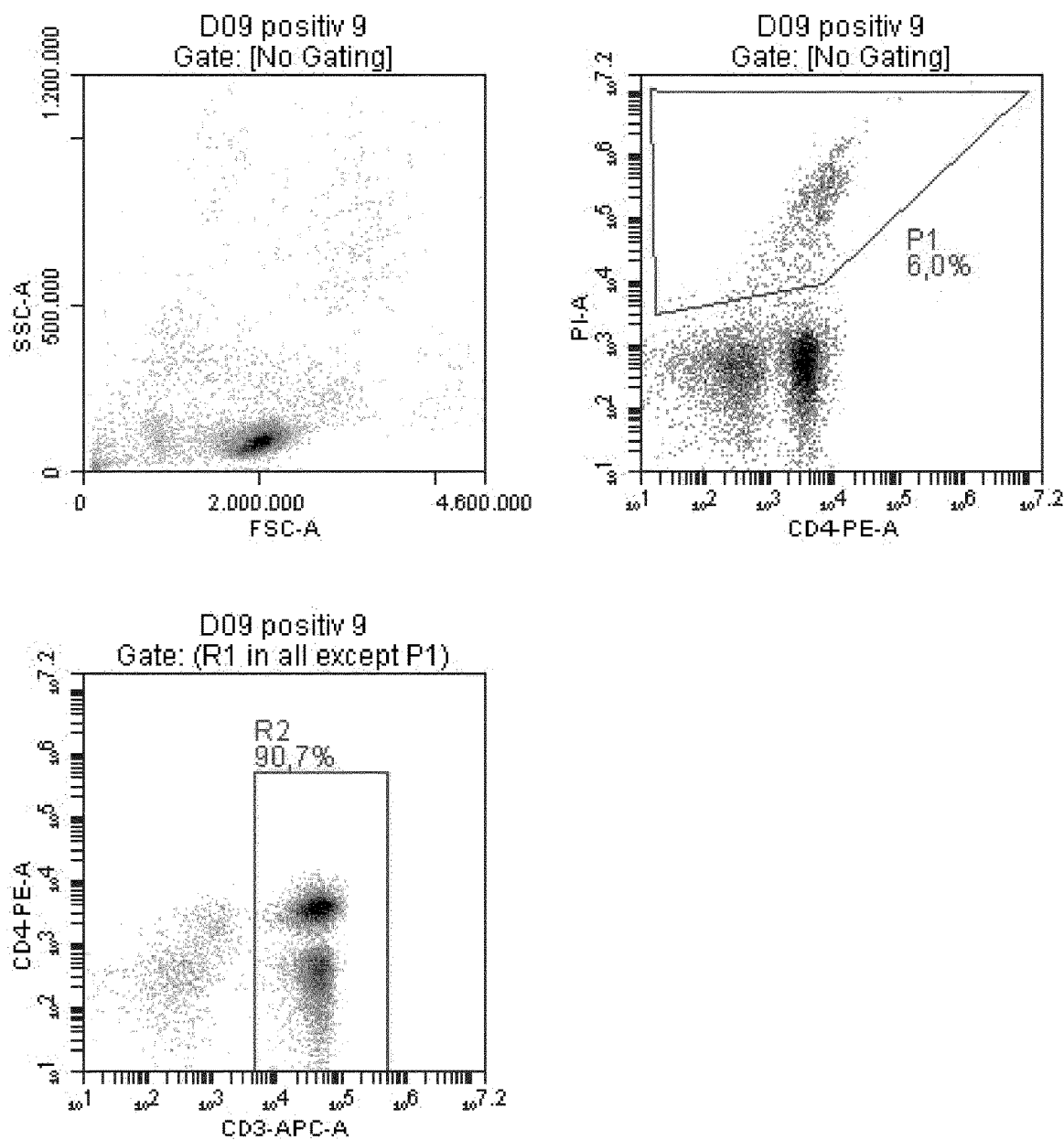
Figure 10C:
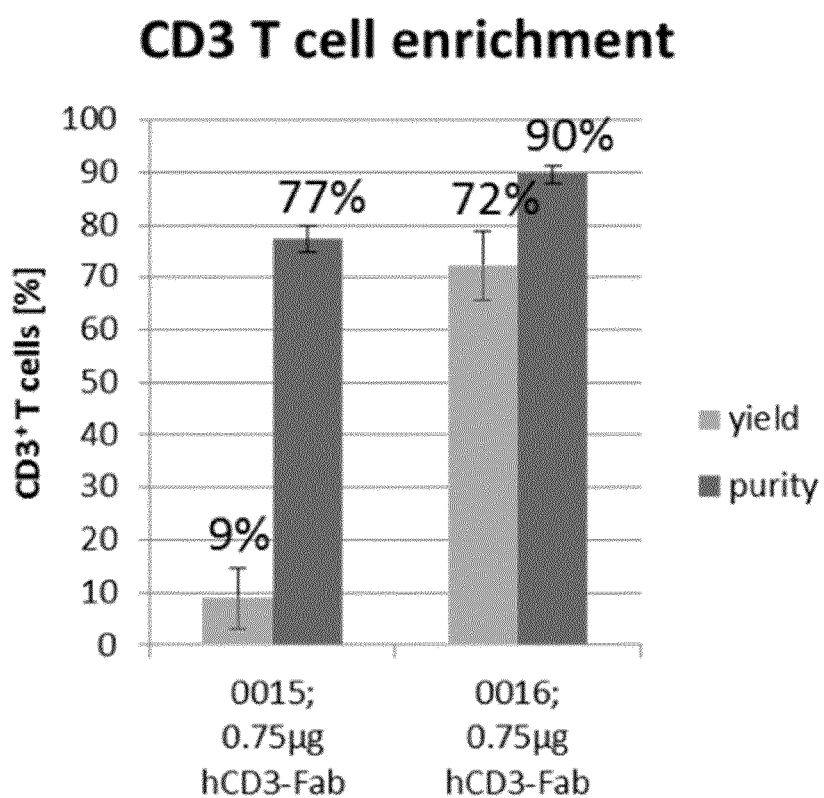

FIG. 8 shows an illustrative assembly of a cell purification column as carried out in the Working Examples. A commercially available spin column is cut to remove the lower end (FIG. 8A). The upper part of the column is then inserted into a suitable cap of a commercially available centrifuge tube, which contains a membrane (FIG. 8B). The cap with the upper column part is placed onto the appendent tube (FIG. 8C).

FIG. 9 shows the results of a comparative experiment for isolating CD8+ cells from a preparation of peripheral blood mononuclear cells (PBMC) by either chromatographic purification using a pipette tip as column as described in International Patent Application WO 2013/124474 (Example 10.1) or using an embodiment of the method of the present invention in which cells were pre-incubated with an CD8 binding Fab fragment and a biotinylated solid phase (Example 10.2). FIG. 9A shows Accuri C6 plots of flow cytometric analysis using Fluorescence-Activated Cell Sorting (FACS) of the initial PBMC preparation before selection (isolation) of the target cells, of the wash through fraction as well as the elution fraction (the CD8+ cells positive fraction) of the isolation as described in International Patent Application WO 2013/124474, while FIG. 9B shows Accuri C6 plots of the FACS analysis of the initial PBMC preparation before selection (isolation) of the target cells, of the wash through fraction as well as the elution fraction (the CD8+ cells positive fraction) of the isolation using an embodiment of the method of the invention. FIG. 9C shows a bar diagram in which yield and purity of the isolated CD8+ cells are compared for both methods. In FIG. 9C the number 0015 denotes the result of the method according to International Patent Application WO 2013/124474, while the number 0016 denotes the result of this embodiment of the method of the invention. The numbers for yield and purity given in % in FIG. 9C are mean values of three independent experiments.

FIG. 10 shows the results of a comparative experiment for isolating CD3+ cells from a preparation of peripheral blood mononuclear cells (PBMC) by either chromatographic purification using a pipette tip as column as described in International Patent Application WO 2013/124474 or using an embodiment of the method of the present invention in which cells were pre-incubated with an CD3 binding Fab fragment and a biotinylated solid phase. FIG. 10A shows Accuri C6 plots of flow cytometric analysis using Fluorescence-Activated Cell Sorting (FACS) of the initial PBMC preparation before selection (isolation) of the target cells, of the wash through fraction as well as the elution fraction (the CD3+ cells positive fraction) of the isolation as described in International Patent Application WO 2013/124474, while FIG. 10B shows Accuri C6 plots of the FACS analysis of the initial PBMC preparation before selection (isolation) of the target cells, of the wash through fraction as well as the elution fraction (the CD8+ cells positive fraction) of the isolation using an embodiment of the method of the invention. FIG. 10C shows a bar diagram in which yield and purity of the isolated CD3+ cells are compared for both methods. In FIG. 10C the number 0015 denotes the result of the method according to International Patent Application WO 2013/124474, while the number 0016 denotes the result of this embodiment of the method of the invention. The numbers for yield and purity given in % in FIG. 10C are mean values of three independent experiments.

DETAILED DESCRIPTION OF THE INVENTION

Provided herein are methods for the isolation or separation of cells and other biologic entities such as cell organelles, viruses, liposomes or prions that are defined by a common specific receptor molecule on the surface—generally by fluid chromatography (which can either by carried out in a batch mode or in a continuous mode). The term "target cell" as used in the following generally refers to all such biological entities (cells, cell organelles, viruses, liposomes or prions).

While the invention is generally explained in the following disclosure with reference to the method of the first aspect of the invention, it is clear that the following disclosure can be equally practiced with the method of the second, third and fourth aspect of the invention as defined herein.

The present invention is based on the surprising finding that the use of a soluble multimerization reagent in combination with a stationary phase having a ligand L that binds a ligand binding partner LB that is part either of a receptor molecule binding reagent or the soluble multimerization reagent provides several advantages over the known methods as described in International Patent Application WO 2013/124474, for example.

First, the invention allows incubating the receptor binding reagent, the multimerization reagent and the sample of the target cells before contacting this reaction mixture with the stationary phase. By so doing, it can be ensured that an equilibrium for the binding of the receptor molecule binding reagent to the receptor molecules and thus to the target cells is reached. Since this incubation includes multimerising monovalent receptor molecule binding reagents by binding them to the plurality of binding sites Z of the multimerization reagent, this ensures that an avidity effect can indeed be achieved when incubating the receptor molecule binding reagent with the target cells. In addition, since a defined multimerization reagent can be use, independent of the kind of receptor molecule binding reagent and/or the selected target cell, the purification protocol can be standardized, irrespective of the used receptor molecule binding reagent and the target cell.

Second, it is believed that the soluble multimerization reagent improves the accessibility of the receptor molecule binding reagent to the (multimerized) receptor molecule binding reagent since, being soluble, the multimerization reagent can, for example, better reach crevices or interact with complex receptor molecules on the surface of the target cells than a sterically and mobility-restricted multimerization reagent that is immobilized on a solid surface such as a chromatography matrix.

As a third advantage, compared to the method of International Patent Application WO 2013/124474 in which a chromatography matrix with a low pore size should ideally be used in order to prevent the receptor molecule binding reagent entering pores and thereby being not available for the isolation of the target cells, any solid phase can be used in the present method, since the unbound receptor molecule binding reagent does not get in contact with the solid phase.

Fourth, due to the possibility of using always the same defined multimerization reagent, a defined and smaller amount receptor molecule binding reagent can be used for the isolation of cells.

Fifth, since the immobilization of the target cells (as part of the multimeric binding complexes formed) is mediated via the ligand binding partner LB of either the receptor molecule binding reagent or the multimerization reagent, this immobilization is independent from the type of used receptor molecule binding reagent and the target cell. Indeed, the same interaction (binding of LB to the ligand L) can be used for immobilization of any given cell type. Thus, also this allows the standardization of the isolation/purification protocol.

Finally, as also explained herein, the use of the soluble multimerization reagent allows the removal of all used reagents (receptor molecule binding reagent, multimerization reagent and competition reagent) by chromatography. This allows the use of an arrangement of a solid phase comprising the ligand L together with at least one of a first stationary phase or a second stationary phase as explained herein. Such an arrangement in turn allows an easy automatization of the isolation methods described herein and thus the development of an automated and closed device for isolation of a target cell, for example, under GMP conditions (it is noted here that all reagents described herein as well as the solid phase comprising the ligand L and the first stationary phase or a second stationary phase can all be prepared under GMP conditions).

Unless otherwise stated, the following terms used in this document, including the description and claims, have the definitions given below.

The term "competition reagent" as used herein refers to any reagent or condition that is able to reduce, interfere with or abrogate the formation of a complex between a pair of binding agents or moieties, such as a binding site B included in a receptor binding reagent and a receptor molecule on the target cell surface, a binding partner C included in a receptor binding reagent and a binding site Z included in a multimerization reagent, or a ligand L and a ligand binding partner LB. The term "competition" is meant to refer any interference with binding, regardless of the nature of such interference. Such interference may in some embodiments also be a non-competitive binding to a certain binding site. An example of such a competition mechanism is the metal chelation by a chelating reagent such as EDTA or EGTA, when the reversibly bond is mediated by complexed metal ions such as $Ca^{2+}$, $Ni^{2+}$, $Co^{2+}$, or $Zn^{2+}$. This mechanism applies for binding pairs such as calmodulin and calmodulin binding peptides that bind in the presence of $Ca^{2+}$ or for binding pairs that are used in Immobilized Metal-chelate Affinity Chromatography (IMAC). In some embodiments a competition reagent may have a binding site that is capable of specifically binding to the binding site included on one of the binding partners, e.g. binding site B, binding site Z, binding partner C or ligand binding partner LB. It is also possible that the entire competition reagent is capable of specifically binding to the binding site included on one of these binding partners. In some embodiments competition is provided by a change in pH or the salt strength of a buffer and the competition reagent is then either an increased or decreased pH or salt strength. A change in pH can, for example, be used for displacing/disrupting the binding of streptavidin to a streptavidin binding peptide or for displacing/disrupting the binding between protein A or protein G and an antibody Fc domain.

The term "isolated" indicates that the target cell or cells, has/have been removed from its/their normal physiological environment, e.g. a natural source. An isolated cell or isolated cells may, for instance, be included in a different medium such as an aqueous solution than provided originally, or placed in a different physiological environment. Typically isolated cells constitute a higher fraction of the total cells present in their environment, e.g. solution/suspension as applicable, than in the environment from which they were taken. Isolation of a desired target cell may in some embodiments include, in addition to the method described herein, general cell enrichment techniques such as centrifugation, filtration or cell chromatography. Lymphocytes such as B cells or T cells may for instance be obtained from peripheral blood, from blood, cerebrospinal fluid, or enriched fractions thereof. B cells or T cells may be obtained from peripheral blood mononuclear cells (PBMC) such as human PBMC. Such PBMC may, for instance, be enriched using know standard techniques based on cell density and/or cell size. As an illustrative example, PBMC may be enriched or isolated via density gradient centrifugation, for example using sucrose, dextran, Ficoll® or Percoll®.

"Isolated" typically means that a sample, e.g. eluate or fraction, obtained contains the target cell as essentially the predominant type of cell (cell population), for example, the target cells represents more than about 10%, about 20%, about 30%, about 40%, about 50%, about 60%, about 70%, about 80%, about 85%, or more than about 90% of the cells present in a sample. In some embodiments isolated target cells define more than about 95%, or more than about 97% of the cells present in a sample. In one embodiment isolated target cells define more than about 99% of the cells present in a sample. "Isolated" also includes that a sample containing the target cell is devoid of reactants—for example, receptor binding reagents, multimerization reagents, or competition reagents as defined herein—after having undergone an isolation/purification method as described herein.

"Isolation" as used herein means that the target cell is enriched in a sample that is obtained as a result of a method described herein compared to the content (concentration) of the sample that was for the isolation of the target cell. In line with the above, this means the target cell may be enriched in a sample, for example from about a content of about 0.1% of the entire amount of cells in a sample to say about 10% or more, or 20% or more in a sample such as an eluate or a fraction obtained using a method disclosed herein. In some embodiments the target cell may be enriched from about a content of about 0.1% of the entire amount of cells in a sample to 30% or more such as 40% or more, in a sample obtained in a method described herein. The term "isolation" also includes the detection of the presence of non-presence of target cells in a sample. Accordingly, the isolation of target cells of can be used either for analytical or preparative purposes (for example, for detecting the presence of a target cell population but also for quantification of cells present in a sample or for isolation of cells on a large scale for cell-based therapy). Analytical purposes may include diagnostic applications as well as applications in basic research in which for example, an isolation method described in this document is used for screening purposes, for example, whether a particular receptor molecule, for example, a G-protein coupled receptor (GPCR) or any other physiologically relevant receptor (e.g. insulin receptor) is recombinantly expressed in a chosen host cells (see also below).

A "stationary phase" in the context of isolating, purifying or enriching a target cell is the part of a chromatographic system that is in contact with a mobile phase. Individual components of a sample applied to the chromatography system may show individual partitioning between the mobile phase and the stationary phase. During chromatography the stationary phase is maintained within a certain space, and has in many embodiments an at least essentially fixed position. The terms "chromatography matrix" and "stationary phase" are used interchangeable herein. In the invention, the stationary phase may be used either in a batch mode or in a flow-through mode.

The term "target cell" as used herein encompasses all biological entities/vesicles in which a membrane, which can also be a lipid bilayer, separates the interior from the outside environment (ambience) and which include one or more kinds of specific receptor molecule(s) on the surface of the biological entity/vesicle. Accordingly the target cell/biological entity/vesicle or the population of target cells is defined by the presence of at least one common specific receptor molecule on the surface thereof.

A target cell or a population of target cells is isolated from a sample that, for example, may include a variety of different cells or cell populations. Virtually any target cell that contains at least one particular receptor molecule can be separated from other components included in a sample. In order to achieve an avidity effect, as discussed below, for a method as as described herein, the receptor molecule is typically present in two or more copies on the surface of the target cell.

In some embodiments the target cell may be a prokaryotic cell, such as a bacterial cell. The cell may in some embodiments be an archaeon. The cell may in some embodiments be a virus or an organelle such as a mitochondrion, a chloroplast, a microsome, a lysosome, a Golgi apparatus or a nucleus. In some embodiments the cell may be a eukaryotic cell, such as a plant cell, a fungal cell, a yeast cell, a protozoon or an animal cell. The target cell includes in some embodiments a cell nucleus. In some embodiments the target cell is a mammalian cell, including but not limited to cells obtained from a human, mouse, rabbit, guinea pig, squirrel, hamster, cat, dog, lemur, goat, pig, horse, rhesus monkey, macaque, or a chimpanzee. Examples of a mammalian cell include, but are not limited to, a blood cell or a tissue cell, e.g. a hepatocyte or a stem cell, e.g. CD34-positive peripheral stem cells or Nanog or Oct-4 expressing stem cells derived from a suitable source. A blood cell may for instance be a leukocyte or an erythrocyte. A leukocyte may for example be a neutrophil, an eosinophil, a basophil, a monocyte, a lymphocyte, a macrophage or a dendritic cell. A respective lymphocyte may for example be a T cell—including a CMV-specific CD8+ T-lymphocyte, a cytotoxic T-cell a, memory T-cell (an illustrative example of memory T-cells are $CD62L^+CD8^+$ specific central memory T-cells) or a regulatory T-cell (an illustrative example of Treg are $CD4^+CD25^+CD45RA+$ Treg cells), a T-helper cell (for example, a $CD4^+$ T-helper cell), a B cell or a natural killer cell, to mention only a few illustrative examples.

The target cell is typically a cell, including a cell population or, as mentioned above, any other population of a biological entity, in which a membrane, which may in some embodiments be a lipid bilayer, separates the interior from the ambience. The target cell is further characterized by having a particular specific receptor molecule on the surface. Such a target cell can be purified by the methods described herein, under subsequent removal of any used purification reagent, such as a receptor binding reagent; a competition reagent; and/or a multimerization reagent. A respective method or use offers—beyond the advantage that, if the target is a cell or an organelle, the physiological status is not altered—the regulatory advantage that the purification reagents are not administered to a subject such as a patient during the use of such purified biological entities as medicaments.

The target cell may, for instance, be a cell of a tissue, such as an organ or a portion thereof. Examples of a respective organ include, without being limited thereto, adrenal tissue, bone, blood, bladder, brain, cartilage, colon, eye, heart, kidney, liver, lung, muscle, nerve, ovary, pancreas, prostate, skin, small intestine, spleen, stomach, testicular, thymus, tumour, vascular or uterus tissue, or connective tissue. In some embodiments the cell is a stem cell, a lymphocyte or a cancer cell.

A sample from which the target cell is to be isolated may be of any origin. It may for instance, but not limited to, be derived from humans, animals, plants, bacteria, fungi, or protozoae. Accordingly, any of the following samples selected from, but not limited to, the group consisting of a soil sample, an air sample, an environmental sample, a cell culture sample, a bone marrow sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a space sample or any combination thereof. Where desired, a respective sample may have been preprocessed to any degree. As an illustrative example, a tissue sample may have been digested, homogenised or centrifuged prior to being used in a method described herein. In another illustrative example, a sample of a body fluid such as blood might be obtained by standard isolation of blood cells. If an isolation method described here is used in basic research, the sample might be cells of in vitro cell culture experiments. The sample will typically have been prepared in form of a fluid, such as a solution or dispersion.

The receptor molecule that is located on the target cell surface, including located on an accessible surface of a biological entity, may be any molecule present on the cell surface during a separation process in a method according to the invention. The receptor molecule is a molecule against which a receptor molecule binding reagent is directed. In some embodiments the receptor is a peptide or a protein, such as a membrane receptor protein. In some embodiments the receptor is a lipid or a polysaccharide. A receptor molecule that is a protein may be a peripheral membrane protein or an integral membrane protein. It may in some embodiments have one or more domains that span the membrane. As a few illustrative examples, the membrane protein may be a CD molecule (cluster of differentiation) such as CD3, CD4, CD8, CD247 (T cell markers), CD8, CD62L, CD45RA (marker for memory T cells), CD4, CD25, CD45RA (markers for regulatory T cells), CD56 (marker for natural killer cells), CD19 (B cell marker) and CD34, Oct-4, Nanog (stem cell markers), to name only a few illustrative example. Accordingly, the target cell may, for instance, a population or subpopulation of blood cells; e.g. lymphocytes such as T cells, T-helper cells, for example, CD4 T-helper cells, B cells or natural killer cells; monocytes; or stem cells, e.g. CD34-positive peripheral stem cells or Nanog or Oct-4 expressing stem cells. Most T cells that have CD8 on their surface are cytotoxic T cells. The target cell may thus be $CD8^+$ a cytotoxic T-cell. The receptor may also be a marker for a tumour cell. The membrane protein may also be a G-protein coupled receptor, such as an odorant receptors, a rhodopsin receptor, a rhodopsin pheromone receptor, a peptide hormone receptor, a taste receptor, a GABA receptor, an opiate receptor, a serotonin receptor, a $Ca^{2+}$ receptor, melanopsin, a neurotransmitter receptor, a receptor kinase such as a serin/threonin kinase, a tyrosine kinase, a porin/channel such as a chloride channel, a potassium channel, or a cell adhesion receptor such as metallo protease, an integrin or a cadherin.

The method described herein may be practiced as part of fluid chromatography, typically a liquid chromatography. Any material may be employed as chromatography matrix in the context of the invention, as long as the material is suitable for the chromatographic isolation of the chosen biological entity such as target cells. A suitable chromatography material is at least essentially innocuous, i.e. not detrimental to cell viability (or the viability or stability of the biological entity), when used in a packed chromatography column under desired conditions for cell isolation and/or cell separation. A chromatography matrix as used in a method described herein typically remains in a predefined location, typically in a predefined position, whereas the location of the sample to be separated and of components included therein, is being altered. As an illustrative example, if packed-bed chromatography columns are employed, the stationary phase is generally confined between the bottom of the column and the flow adapter. Where chromatography is carried out as expanded bed adsorption, the resin becomes fluidized in use, and beads employed arrange in the form of a concentration gradient, individual beads taking a position where their sedimentation velocity matches the upward liquid flow velocity. The chromatography matrix is thus a "stationary phase" in line with the common understanding of the person skilled in the art in that the stationary phase is that part of a chromatographic system through which the mobile phase flows and where components included in the liquid phase are being disseminated between the phases.

If beads are employed, in column chromatography beads are commonly rather uniform in size, whereas in expanded bed adsorption beads are variable in size, typically ranging from about 50 to about 400 mm. In this regard, it is noted that particles such as freely moveable magnetic beads that are added to a liquid sample, mixed with the sample and are then removed from the sample, for example, by discarding the supernatant (liquid) while holding the beads temporarily in place (for example, by an external magnetic or by centrifugation) are in one embodiment not a stationary phase as used herein. However, the method of the invention can also be practiced in a batch mode. In such a method (magnetic) beads can be added to a sample containing the target cells for immobilization of the target cells (via a complex formed between the target cells, the receptor binding reagent and the affinity/multimerization reagent) on such beads, and the beads are then separated from the sample, for example by temporarily holding the beads in place, while discarding the supernatant. Such a batch method is also a method according to the invention.

Typically, the respective chromatography matrix has the form of a solid or semi-solid phase, whereas the sample that contains the target cell to be isolated/separated is a fluid phase. The mobile phase used to achieve separation is likewise a fluid phase. The chromatography matrix can be a particulate material (of any suitable size and shape) or a monolithic chromatography material, including a paper substrate or membrane. Thus, the chromatography can for example be column chromatography. In some embodiments the chromatography may be planar chromatography. In some embodiments the chromatography may be expanded bed chromatography. If a particulate matrix material is used in column chromatography, the particulate matrix material may, for example, have a mean particle size of about 5 μm to about 200 μm, or from about 5 μm to about 400 μm, or from about 5 μm to about 600 μm. As explained in detail the following, the chromatography matrix may, for example, be or include a polymeric resin or a metal oxide or a metalloid oxide. If planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetisable material.

Non-magnetic or non-magnetisable chromatography stationary phases that are used in the art, and that are also suitable in a method described herein, include derivatized silica or a crosslinked gel. A crosslinked gel (which is typically manufactured in a bead form) may be based on a natural polymer, i.e. on a polymer class that occurs in nature. For example, a natural polymer on which a chromatography stationary phase is based is a polysaccharide. A respective polysaccharide is generally crosslinked. An example of a polysaccharide matrix is an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

A crosslinked gel may also be based on a synthetic polymer, i.e. on a polymer class that does not occur in nature. Usually such a synthetic polymer on which a chromatography stationary phase for cell separation is based is a polymer that has polar monomer units, and which is therefore in itself polar. Such a polar polymer is hydrophilic. Hydrophilic ("water-loving") molecules, also termed lipophobic ("fat hating"), contain moieties that can form dipole-dipole interactions with water molecules. Hydrophobic ("water hating") molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments a chromatography stationary phase may also include natural and synthetic polymer components, such as a composite matrix or a composite or a copolymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. A derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

A solid phase such as a chromatography matrix employed in a method described herein may also include magnetically attractable particles. Also such respective magnetically attractable particles may include a ligand L that is capable of binding a ligand binding partner LB of a multimerization reagent. Magnetically attractable particles may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic Micro-Beads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hütten, A. et al. (J. Biotech. (2004), 112, 47-63). In some embodiments a chromatography matrix employed in a method disclosed herein is void of any magnetically attractable matter.

In a method of isolating a target cell, a chromatography matrix may be employed as an affinity chromatography matrix. An affinity chromatography matrix may itself include permanently bonded (usually covalently bonded) moieties that are capable to specifically bind a selected target. For example, a conventional affinity chromatography matrix may include an antibody that binds a particular given target. Alternatively, a chromatography matrix that is used for Immobilized Metal-chelate Affinity Chromatography (IMAC) is modified with a chelating ligand agent such as tridentate iminodiacetic acid to be able to form coordination bonds between metal ions and certain exposed side chains of a protein or with oligohistidine tags, for example. Thus, in the art an affinity chromatography matrix is generally designed such that it, by itself, is able to specifically bind the target that is to be isolated. In some embodiments of a method as disclosed herein, a stationary phase is used as a replacement for a "selection cartridge" as described in International Patent Application WO 2013/124474.

The multimerization reagent includes two or more binding sites Z for the binding partner C included in the receptor binding reagent. In the then non-covalent binding complex formed, two or more receptor binding reagents are bound to the multimerization reagent. The bound receptor binding reagents are closely arranged to each other such that an avidity effect can take place if a target cell having (at least two copies of) a receptor molecule is present in the sample, is brought into contact with the receptor binding reagent that has one or more binding sites B being able to bind the particular receptor molecule. In some embodiments the receptor binding reagent includes a plurality of, such as two or more, binding sites B for the receptor on the target cell.

Thus, in a method described herein where a plurality of receptor binding reagents are bound to the multimerization reagent, an avidity (multimerization) effect as the one described in U.S. Pat. No. 7,776,562 or International Patent application WO 02/054065 can take place, allowing the formation of a target cell/multivalent binding complex. This target cell/multivalent binding complex can be reversibly immobilized on a stationary phase, thereby immobilizing the target cells on the stationary phase. Since the bond between the binding sites Z of the multimerization reagent and the binding partner C of the receptor molecule binding reagent can be disrupted by addition of a competition agent, the target cells can be subsequently eluted under mild conditions under which the receptor molecule binding reagent completely dissociates from the target cell, thereby avoiding that the receptor molecule binding reagent affects the functional status of the target cell. This isolation of target cells via this affinity chromatography method thus does not only have the advantage that it allows for the isolation/purification of target cell population (or any other biological entity described herein) without altering the functional status of the target cell population that is defined by a common specific receptor molecule. Rather, this method also has the added advantage that it entirely abolishes the need to use magnetic beads for cell purification and thereby simplifies any further handling of the cell and further opens the way to automatization of the isolation of target cells, as also described herein.

A chromatography matrix, such as a first or, if employed, a second stationary phase, is in some embodiments included in a chromatography column, for example packed therein. In some embodiments a first and a second stationary phase is employed. The first stationary phase corresponds to the stationary phase described above, it includes for instance a ligand L. The second stationary phase may be used to deplete the eluate of the first stationary phase from reagents used such as the receptor binding reagent, a competition reagent and/or a multimerization reagent. Such a second stationary phase can thus be a "removal cartridge" as described in International Patent Application WO 2013/124474. In some embodiments the second stationary phase includes an affinity reagent, typically covalently attached thereto. The affinity reagent is able to bind a binding partner C that is included in a receptor binding reagent. The affinity reagent may also be able to bind a competition reagent. Such a chromatography matrix may be an affinity chromatography matrix. It may also be a gel filtration matrix, to which the affinity reagent has been coupled. By means of the immobilized affinity reagent the chromatography matrix can deplete a mobile phase of the receptor molecule binding reagent. A sample that is contacted with the chromatography matrix, for example, loaded onto a column packed therewith, can likewise be depleted of the receptor binding reagent. As an illustrative example, in case of using streptavidin binding peptides as binding partner C and biotin as competition reagent, the affinity reagent can streptavidin coupled to a chromatography matrix such as Sephararose™ (see International Patent Application WO 2013/124474 for a detailed description of such a "removal cartridge"). In addition, in case soluble oligomers of streptavidin or a streptavidin mutein are used as soluble multimerization reagent, such a multimerization reagent can be removed from the eluate by a further (third) stationary phase which has biotin immobilized/covalently coupled thereon (see the biotin-sepharose commercially available from Affiland S.A. (Ans-Liege, Belgium, or the Superflow® agarose with covalently bound biotin prepared here in the Experimental Section). The soluble streptavidin based multimerization reagent will be immobilized on the solid phase by binding to its biotin groups. Thus, the present invention provides the possibility of automated isolation of the target cells under removal of all reagents used in the method of the invention.

After applying a sample that contains the target cell, a chromatography matrix as used herein may subsequently be washed with a mobile phase, such as an aqueous medium, e.g. a buffer, in order to remove any matter that has not been immobilized on the chromatography matrix. Such washing may be carried out on any stationary phase employed in the context of a method or use described herein. The respective chromatography matrix may be used as a first stationary phase or as a secondary stationary phase.

Dissociation of the above described non-covalent multivalent complexes, the formation of which immobilizes the target cell on the affinity chromatography matrix, may then be induced, for example, by a change in conditions. Such a change in conditions may for instance be a change in the pH or ionic strength of an aqueous mobile phase. In some embodiments, a competition reagent is employed in order to induce dissociation of the reversible non-covalent complex between the receptor molecule binding reagent and multimerization reagent. The competition reagent is able to associate to the multimerization reagent by occupying or blocking the binding site of the multimerization reagent for the binding partner included in the receptor binding reagent. By using a competition reagent with a particularly high affinity for the multimerization reagent or by using an excess of the competition reagent relative to concentration of the receptor molecule binding reagent (in this case, the competition reagent might also have a lower affinity to the binding site Z of the multimerization reagent than the binding partner C of the receptor binding reagent) the non-covalent bonding between the receptor binding reagent and the multimerization reagent may be disrupted. The target cell is allowed to elute from the chromatography matrix, e.g. from the column into which the chromatography matrix is packed. The eluate is collected and the target cell thereby collected.

The fluid phase used as the mobile phase in chromatography may be any fluid suitable for preserving the biological activity of the target cell. Typically, the fluid is a liquid. In some embodiments the respective liquid is or includes water, for example in the form of an aqueous solution. Further components may be included in a respective aqueous solution, for example dissolved or suspended therein. As an illustrative example an aqueous solution may include one or more buffer compounds. Numerous buffer compounds are used in the art and may be used to carry out the various processes described herein. Examples of buffers include, but are not limited to, solutions of salts of phosphate such as phosphate buffered saline (PBS), carbonate, succinate, carbonate, citrate, acetate, formate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methylamino]-1-ethansulfonic acid (also called TES), 2-cyclohexylamino-ethanesulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, zwitter-ionic buffers such as betaine, ethylamine, triethylamine, glycine, glycylglycine, histidine, tris-(hydroxymethyl)aminomethane (also called TRIS), bis-(2-hydroxyethyl)-imino-tris(hydroxymethyl)-methane (also called BIS-TRIS), and N-[Tris(hydroxymethyl)-methyl]-glycine (also called TRICINE), to name only a few. The buffer may further include components that stabilize the target cell to be isolated, for example proteins such as (serum) albumin, growth factors, trace elements and the like. The choice of the suitable mobile phase is within the knowledge of the person of average skill in the art and can be carried out empirically.

In line with international patent application International Patent Application WO2013/011011, the strength of the binding between the receptor molecule binding reagent and the receptor molecule on a target cell may not be essential for the reversibility of the binding of the target cell to the multimerization reagent via the receptor binding reagent. Rather, irrespective of the strength of the binding, meaning whether the dissociation constant ($K_d$) for the binding between the receptor binding reagent via the binding site B and the receptor molecule is of low affinity, for example, in the range of a $K_d$ of about $10^{-3}$ to about $10^{-7}$ M, or of high affinity, for example, in the range of a $K_d$ of about $10^{-7}$ to about $1 \times 10^{-10}$ M, a target cell can be reversibly bound as long as the dissociation of the binding of the receptor binding reagent via the binding site B and the receptor molecule on the target cell surface occurs sufficiently fast. In this regard the dissociation rate constant ($k_{off}$) for the binding between the receptor binding reagent via the binding site B and the receptor molecule may have a value of about $3\times10^{-5}$ $sec^{-1}$ or greater. This dissociation rate constant is the constant characterizing the dissociation reaction of the complex formed between the binding site B of the receptor binding reagent and the receptor molecule on the surface of the target cell. The association rate constant ($k_{on}$) for the association reaction between the binding site B of the receptor binding reagent and the receptor molecule on the surface of the target cell may have any value. In order to ensure a sufficiently reversible binding between receptor molecule and receptor binding reagent it is advantageous to select the $k_{off}$ value of the binding equilibrium to have a value of about $3\times10^{-5}$ $sec^{-1}$ or greater, of about $5\times10^{-5}$ $sec^{-1}$ or greater, such as about $1\times10^{-4}$ $sec^{-1}$ or greater, about $1.5\times10^{-4}$ $sec^{-1}$ or greater, about $2.0\times10^{-4}$ $sec^{-1}$ or greater, about $2.5\times10^{-4}$ $sec^{-1}$ or greater, about $3\times10^{-4}$ $sec^{-1}$ or greater, about $3.5\times10^{-4}$ $sec^{-1}$ or greater, about $4\times10^{-4}$ $sec^{-1}$ of greater, about $5\times10^{-4}$ $sec^{-1}$ or greater, about $7.5\times10^{-4}$ $sec^{-1}$ or greater, about $1\times10^{-3}$ $sec^{-1}$ or greater, about $1.5\times10^{-3}$ $sec^{-1}$ or greater, about $2\times10^{-3}$ $sec^{-1}$ or greater, about $2.5\times10^{-3}$ $sec^{-1}$ or greater, about $3\times10^{-3}$ $sec^{-1}$ or greater, about $4\times10^{-3}$ $sec^{-1}$, about $5\times10^{-3}$ $sec^{-1}$ or greater, about $7.5\times10^{-3}$ $sec^{-1}$ or greater, about $1\times10^{-2}$ $sec^{-1}$ or greater, about $5\times10^{-2}$ $sec^{-1}$ or greater, about $1\times10^{-1}$ $sec^{-1}$ or greater or about $5\times10^{-1}$ $sec^{-1}$ or greater. The term "about" when used herein in relation to the $k_{off}$ rate, the $k_{on}$ rate or the $K_D$ (see below) is meant to include an error margin of ±20.0%, including ±15.0%, ±10.0%, ±8.0%, ±9.0%, ±7.0%, ±6.0%, ±5.0%, ±4.5%, ±4.0.%, ±3.5%, ±3.0%, ±2.8%, ±2.6%, ±2.4,%, ±2.2%, ±2.0%, ±1.8,%, ±1.6%, ±1.4%, ±1.2%, ±1.0, %, ±0.9%, ±0.8%, ±0.7%, ±0.6%, ±0.5%, ±0.4%, ±0.3%, ±0.2%, ±0.1%, or ±0.01%. It is noted here that the values of the kinetic and thermodynamic constants as used herein, refer to conditions of atmospheric pressure, i.e. 1.013 bar, and room temperature, i.e. 25° C.

In some embodiments the receptor molecule binding reagent has a single (monovalent) binding site B capable of specifically binding to the receptor molecule. Examples of such monovalent receptor molecule binding reagents are soluble MHC I peptides (which are being complexed with an cell specific antigen presenting peptides (such MHC molecules are, for example, described in International Patent Application, WO 02/054065 or, Schmidt, J. et al., J. Biol. Chem. [2011] 286, 48, 41723-41735 and are commercially available from IBA GmbH or TC Metrix S.A., for example), mononvalent antibody fragments such as, for example, Fab fragments, Fv fragments or single chain Fv fragments (scFv) or a monovalent artificial binding molecule (proteinaceous or other) such as a mutein based on a polypeptide of the lipocalin family (also known as "Anticalin®). Alternatively, the receptor molecule binding reagent may also have two or more binding sites B. Examples of such receptor molecule binding reagents are intact (bivalent) antibody molecules or an antibody fragments in which both binding sites are retained such as an F(ab')$_2$ fragment. The receptor molecule binding reagent may be a multivalent molecule such as a pentameric IgE molecule.

In some embodiments, it is on a molecular level not the $k_{off}$ rate (of $3\times10^{-5}$ $sec^{-1}$ or greater) of the binding of the receptor molecule binding reagent via the at least binding site B and the receptor molecule on the target cell that allows in combination with the reversible reagents described here the isolation of target cells as described here. Rather, and as described, for example, in U.S. Pat. No. 7,776,562 or International Patent application WO 02/054065, a low affinity binding between the receptor molecule and the binding site B of the receptor molecule binding reagent together with an avidity effect mediated via the immobilized multimerization reagent allows for a reversible isolation of a target cell. In these embodiments a complex between the two or more binding sites Z of the multimerization reagent and the binding partner C of at least two receptor binding reagents can form, allowing a reversible immobilization and subsequent elution of the target cells from the solid phase (via addition of the competing reagent that will disrupt the binding (complex) formed between the binding partner C and the binding sites Z which in turn leads to the dissociation of the receptor binding reagent from the target cell). Such a low binding affinity may be characterized by a dissociation constant ($K_D$) in the range from about the range of about $10^{-2}$ M or $10^{-3}$ M to about $10^{-7}$ M, or about $10^{-3}$ M to about $10^{-6}$ M, or to about $10^{-4}$ M to about $10^{-7}$ M.

As indicated above, the receptor molecule binding reagent has, in addition to the binding site B that is able to bind the receptor molecule, a binding partner C. This binding partner C is able to reversibly bind to a binding site Z of the multimerization reagent, wherein the multimerization reagent has one or more binding sites for the binding partner C. The non-covalent bond that is formed between the binding partner C that is included in the receptor binding reagent and the binding site(s) Z of the multimerization reagent may be of any desired strength and affinity, as long as it is disruptable or reversible under the conditions under which the method of the invention is performed. The dissociation constant ($K_D$) of the binding between the binding partner C that is included in the receptor molecule binding reagent and the binding site Z of the multimerization reagent may have a value in the range from about $10^{-2}$ M to about $10^{-13}$ M. Thus, this reversible bond can, for example, have a $K_D$ from about $10^{-2}$ M to about $10^{-13}$ M, or from about $10^{-3}$ M to about $10^{-12}$ M or from about $10^{-4}$ M to about $10^{-11}$M, or from about $10^{-5}$ M to about $10^{-10}$M. The $K_D$ of this bond as well as the $K_D$, $k_{off}$ and $k_{on}$ rate of the bond formed between the binding site B of the receptor molecule binding reagent and the receptor molecule can be determined by any suitable means, for example, by fluorescence titration, equilibrium dialysis or surface plasmon resonance. The receptor molecule binding reagent may include at least one, including two, three or more, second binding partners C and the multimerization reagent may include at least two, such as three, four, five, six, seven, eight or more binding sites for the binding partner that is included in the receptor molecule binding reagent. As described in U.S. Pat. No. 7,776,562 or International Patent application WO 2002/054065 any combination of a binding partner C and an multimerization reagent with one or more corresponding binding sites Z can be chosen, as long as the binding partner C and the binding site Z of the multimerisation reagent are able to reversibly bind or multimerize in a (multivalent) complex to cause an avidity effect.

The binding partner C included in the receptor molecule binding may be an oligopeptide, a polypeptide, a protein, a nucleic acid, a lipid, a saccharide, an oligosaccharide, or a polysaccharide. Such a binding partner has a higher affinity to the binding site of the multimerization reagent than to other matter. Examples of a respective binding partner include, but are not limited to, an immunoglobulin molecule, a fragment thereof and a proteinaceous binding molecule with antibody-like functions.

In some embodiments the binding partner C that is included in the receptor binding reagent includes biotin and the multimerization reagent includes a streptavidin analog or an avidin analog that reversibly binds to biotin. In some embodiments the binding partner C that is included in the receptor binding reagent includes a biotin analog that reversibly binds to streptavidin or avidin, and the multimerization reagent includes streptavidin, avidin, a streptavidin analog or an avidin analog that reversibly binds to the respective biotin analog. In some embodiments the binding partner C that is included in the receptor binding reagent includes a streptavidin or avidin binding peptide and the multimerization reagent includes streptavidin, avidin, a streptavidin analog or an avidin analog that reversibly binds to the respective streptavidin or avidin binding peptide.

In some embodiments the binding partner C that is included in the receptor binding reagent may include a streptavidin-binding peptide that comprises or consists of one of the following sequences:

a) -Trp-Xaa-His-Pro-Gln-Phe-Yaa-Zaa- (SEQ ID NO: 1), wherein Xaa is any amino acid and Yaa and Zaa are both Gly or Yaa is Glu and Zaa is Lys or Arg, b)
                                         (SEQ ID NO: 2)
-Trp-Arg-His-Pro-Gln-Phe-Gly-Gly-, c)
                                         (SEQ ID NO: 3)
-Trp-Ser-His-Pro-Gln-Phe-Glu-Lys-, d) a sequential arrangement of at least two streptavidin binding peptides, wherein each peptide binds streptavidin, wherein the distance between two peptides is at least 0 and not greater than 50 amino acids and wherein each of the at least two peptides comprises the amino acid sequence -His-Pro-Baa- in which Baa is selected from the group consisting of glutamine, asparagine and methionine, e) a sequential arrangement as recited in d), wherein one of the at least two peptides comprises the sequence -His-Pro-Gln-, f) a sequential arrangement as recited in d), wherein one of the peptides comprises an amino acid sequence -His-Pro-Gln-Phe- (SEQ ID NO: 4), g) a sequential arrangement as recited in d) wherein at least one peptide includes at least the amino sequence -Oaa-Xaa-His-Pro-Gln-Phe-Yaa-Zaa- (SEQ ID NO: 5), where Oaa is Trp, Lys or Arg, Xaa is any amino acid and where either Yaa and Zaa are both Gly or Yaa is Glu and Zaa is Lys or Arg, h) a sequential arrangement as recited in d) wherein at least one peptide includes at least the amino acid sequence -Trp-Xaa-His-Pro-Gln-Phe-Yaa-Zaa- (SEQ ID NO: 6) where Xaa is any amino acid and where either Yaa and Zaa are both Gly or Yaa is Glu and Zaa is Lys or Arg, i) a sequential arrangement as recited in d) wherein at least one peptide includes at least the amino acid sequence -Trp-Ser-His-Pro-Gln-Phe-Glu-Lys- (SEQ ID NO: 7), j) the amino acid sequence -Trp-Ser-His-Pro-Gln-Phe-Glu-Lys-(Xaa)n-Trp-Ser-His-Pro-Gln-Phe-Glu-Lys- (SEQ ID NO: 8) wherein Xaa is any amino acid and n is an integer from 0 to 12.

k) an amino acid sequence selected from the group consisting of Trp-Arg-His-Pro-Gln-Phe-Gly-Gly (SEQ ID NO: 9), Trp-Ser-His-Pro-Gln-Phe-Glu-Lys (SEQ ID NO: 10), Trp-Ser-His-Pro-Gln-Phe-Glu-Lys-(GlyG-lyGlySer)$_3$-Trp-Ser-His-Pro-Gln-Phe-Glu-Lys (SEQ ID NO: 11), Trp-Ser-His-Pro-Gln-Phe-Glu-Lys-(GlyGlyGlySer)$_2$-Trp-Ser-His-Pro-Gln-Phe-Glu-Lys (SEQ ID NO: 12) or Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 13).

In these cases, the multimerization reagent may include the streptavidin mutein (analog) Val$^{44}$-Thr$^{45}$-Ala$^{46}$-Arg$^{47}$ or the streptavidin mutein (analog) Ile$^{44}$-Gly$^{45}$-Ala$^{46}$-Arg$^{47}$, both of which are described in U.S. Pat. No. 6,103,493, for example, and are commercially available under the trademark Strep-Tactin®. Such multimeric streptavidin muteins may also be referred to as multimerized Strep-Tactin.

In some embodiment the binding partner C of the receptor molecule binding reagent includes a moiety known to the skilled artisan as an affinity tag. In such an embodiment the multimerization reagent includes a corresponding binding partner, for example, an antibody or an antibody fragment, known to bind to the affinity tag. As a few illustrative examples of known affinity tags, the binding partner C that is included in the receptor molecule binding reagent may include an oligohistidine, maltose-binding protein, glutathione-S-transferase (GST), chitin binding protein (CBP) or thioredoxin, calmodulin binding peptide (CBP), FLAG-peptide, the HA-tag (sequence: Tyr-Pro-Tyr-Asp-Val-Pro-Asp-Tyr-Ala, SEQ ID NO: 15), the VSV-G-tag (sequence: Tyr-Thr-Asp-Ile-Glu-Met-Asn-Arg-Leu-Gly-Lys, SEQ ID NO: 16), the HSV-tag or HSV epitope of the herpes simplex virus glycoprotein D (sequence: Gln-Pro-Glu-Leu-Ala-Pro-Glu-Asp-Pro-Glu-Asp, SEQ ID NO: 17), the T7 epitope (Ala-Ser-Met-Thr-Gly-Gly-Gln-Gln-Met-Gly, SEQ ID NO: 21), maltose binding protein (MBP), the "myc" epitope of the transcription factor c-myc of the sequence Glu-Gln-Lys-Leu-Ile-Ser-Glu-Glu-Asp-Leu (SEQ ID NO: 14), the VS-tag (sequence: Gly-Lys-Pro-Ile-Pro-Asn-Pro-Leu-Leu-Gly-Leu-Asp-Ser-Thr, SEQ ID NO: 18), or glutathione-S-transferase (GST). In such an embodiment the complex formed between the one or more binding sites of the multimerization reagent, in this case an antibody or antibody fragment, and the antigen can be disrupted competitively by adding the free antigen, i.e. the free peptide (epitope tag) or the free protein (such as MBP or CBP). The affinity tag might also be an oligonucleotide tag. Such an oligonucleotide tag may, for instance, be used to hybridize to an oligonucleotide with a complementary sequence, linked to or included in the multimerization reagent.

Further examples of a suitable binding pair include using an immunoglobulin domain such as antibody Fc domain as binding partner C in the receptor molecule binding reagent and protein A, protein G or protein L as multimerization reagent. Protein A, protein G and protein L are all able to reversibly bind an antibody Fc domain. The binding can be disrupted by a change in the buffer conditions, for example, by increasing the salt strength of the buffer or by reducing the pH from, for example a neutral pH of about 7.0 to a pH of about 3.0 to about 2.5.

In some embodiments the binding between the binding partner C that is included in the receptor binding reagent and one or more binding sites Z of the multimerization reagent occurs in the presence of a divalent, a trivalent or a tetravalent cation. In this regard in some embodiments the affinity/multimerization reagent includes a divalent, a trivalent or a tetravalent cation, typically held, e.g. complexed, by means of a suitable chelator. The binding partner that is included in the receptor binding reagent may in such an embodiment include a moiety that includes, e.g. complexes, a divalent, a trivalent or a tetravalent cation. Examples of a respective metal chelator, include, but are not limited to, ethylenediamine, ethylenediaminetetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis(o-aminophen-oxy) ethane-N,N,N',N'-tetraacetic acid (BAPTA), 2,3-dimercapto-1-propanol (dimercaprol), porphine and heme. As an example, EDTA forms a complex with most divalent, trivalent and tetravalent metal ions, such as e.g. calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments the binding partner C that is included in the receptor molecule binding reagent includes a calmodulin binding peptide and the multimerization reagent includes multimeric calmodulin as described in U.S. Pat. No. 5,985,658, for example. In some embodiments the binding partner C that is included in the receptor molecule binding reagent includes a FLAG peptide and the multimerization reagent includes an antibody that binds to the FLAG peptide, e.g. the FLAG peptide, which binds to the monoclonal antibody 4E11 as described in U.S. Pat. No. 4,851,341. In some embodiments the antibody that binds to the FLAG peptide may be the commercially available monoclonal antibody M1. In one embodiment the binding partner C that is included in the receptor molecule binding reagent includes an oligohistidine tag and the multimerization reagent includes chelating groups K that bind a transition metal ion and thereby are also able of binding an oligohistidine tag. The disruption of all these binding complexes may be accomplished by metal ion chelation, e.g. calcium chelation, for instance by adding EDTA or EGTA (supra). Calmodulin, antibodies such as 4E11 or chelated metal ions or free chelators may be multimerized by conventional methods, e.g. by biotinylation and complexation with streptavidin or avidin or multimers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In such embodiments the binding between the binding partner C that is included in the receptor binding reagent and the one or more binding sites Z of the multimerization reagent can be disrupted by metal ion chelation. The metal chelation may, for example, be accomplished by addition of EGTA or EDTA.

In some embodiments the soluble multimerization reagent is an oligomer or a polymer of streptavidin or avidin or of any analog of streptavidin or avidin. The binding site Z is the natural biotin binding of avidin or streptavidin. A respective oligomer or polymer may be obtained from a corresponding monomeric streptavidin or avidin, or analog thereof. Such a multimerization reagent is for example commercially available from IBA GmbH, Göttingen, Germany as "Strep-Tactin® PE for Fab Streptamers" (catalogue number 6-5001-010 or 6-5011-010, coupled to a fluorescent label—this label does not interfere in the method of the invention and thus do not need to be removed). In addition, a variety of techniques for forming an oligomer or polymer are known in the art. The respective oligomer or polymer may for instance be crosslinked by a polysaccharide. In one embodiment oligomers or polymers of streptavidin or of avidin or of analogs of streptavidin or of avidin are prepared by the introduction of carboxyl residues into a polysaccharide, e.g. dextran, essentially as described in Noguchi, A, et al., Bioconjugate Chemistry (1992) 3, 132-137 in a first step. Then streptavidin or avidin or analogs thereof may be linked via primary amino groups of internal lysine residue and/or the free N-terminus to the carboxyl groups in the dextran backbone using conventional carbodiimide chemistry in a second step. Cross-linked oligomers or polymers of streptavidin or avidin or of any analog of streptavidin or avidin may also be obtained by crosslinking via bifunctional molecules, serving as a linker, such as glutardialdehyde or by other methods described in the art. The use of iminothiolan/SMCC, NHS activated carboxydextran or dendrimers are further examples of crosslinking techniques established in the art.

As an illustrative example, an oligomer or a polymer of streptavidin or of avidin or of an analog of streptavidin or of avidin may be prepared by the introduction of carboxyl residue into a polysaccharide such as dextran, essentially as described by Noguchi et al. (Bioconjugate Chemistry [1992] 3, 132-137) in a first step. Then streptavidin or avidin or an analog thereof can be coupled via primary amino groups of internal lysine residues and/or the free N-terminus to the carboxyl groups in the dextran backbone using conventional carbodiimide chemistry in a second step. In one embodiment the coupling reaction is performed at a molar ratio of about 60 moles streptavidin or streptavidin mutein per mole of dextran.

In some embodiments, streptavidin muteins that are used for isolation of a target cell as described here are those streptavidin muteins which are described in U.S. Pat. No. 6,103,493 and also in DE 196 41 876.3. These streptavidin muteins have at least one mutation within the region of amino acid positions 44 to 53, based on the amino acid sequence of wild-type streptavidin. In some embodiments a mutein of a minimal streptavidin is used. A mutein of a minimal streptavidin starts N-terminally in the region of amino acids 10 to 16 of wild-type streptavidin and ends C-terminally in the region of amino acids 133 to 142 of wild-type streptavidin. Examples of such streptavidin muteins have a hydrophobic aliphatic amino acid instead of Glu at position 44, any amino acid at position 45, a hydrophobic aliphatic amino acid at position 46 or/and a basic amino acid instead of Val at position 47. The streptavidin mutein may be the mutein $Val^{44}$-$Thr^{45}$-$Ala^{46}$-$Arg^{47}$ or the streptavidin mutein (analog) $Ile^{44}$-$Gly^{45}$-$Ala^{46}$-$Arg^{47}$, both of which are described in U.S. Pat. No. 6,103,493, for example, and which are commercially available under the trademark Strep-Tactin®.

As wild-type streptavidin (wt-streptavidin), the amino acid sequence disclosed by Argarana et al., Nucleic Acids Res. 14 (1986) 1871-1882 is referred to. Streptavidin muteins are polypeptides which are distinguished from the sequence of wild-type streptavidin by one or more amino acid substitutions, deletions or additions and which retain the binding properties of wt-streptavidin. Streptavidin-like polypeptides and streptavidin muteins are polypeptides which essentially are immunologically equivalent to wild-type streptavidin and are in particular capable of binding biotin, biotin derivative or biotin analogues with the same or different affinity as wt-streptavidin. Streptavidin-like polypeptides or streptavidin muteins may contain amino acids which are not part of wild-type streptavidin or they may include only a part of wild-type streptavidin. Streptavidin-like polypeptides are also polypeptides which are not identical to wild-type streptavidin, since the host does not have the enzymes which are required in order to transform the host-produced polypeptide into the structure of wild-type streptavidin. The term "streptavidin" also includes streptavidin tetramers and streptavidin dimers, in particular streptavidin homotetramers, streptavidin homodimers, streptavidin heterotetramers and strepavidin heterodimers. Each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

As mentioned above, the solid phase used in the present invention comprises a ligand L that is able to (specifically) bind the ligand binding partner LB which is comprised in the multimerization reagent. The bond formed between the ligand L and the ligand binding partner LB provides for the (reversible) immobilization of the target cells (being part of the multivalent binding complex) on the solid phase. Thus, as such the bond formed between LB and L does not have to reversible but can also be irreversible. In this case, a covalent bond might be formed between L and LB. Alternatively, L might be biotin and LB might be the biotin binding site of avidin or streptavidin. This binding while being based on non-covalent interactions has a dissociation constant (Kd) of about $1 \times 10^{-15}$ M and is considered to be irreversible.

However, it is also possible that the binding between L and LB is reversible. In this case, the dissociation constant $K_d$ of the bond of the ligand L to the ligand binding partner LB can be smaller than the dissociation constant $K_d$ of the reversible bond of the binding partner C to the binding site Z. In other words, the binding between L and LB is then stronger than the binding of the binding partner C to the binding site Z. In this context, it is noted that the two binding pairs considered herein (first binding pair: binding partner C of the receptor molecule binding reagent and binding site Z of the multimerization reagent; second binding pair: ligand L of the solid phase and ligand binding partner LB comprised in the multimerization reagent) can be chosen such that the binding pairs can be disrupted (displaced) by either the same or also different competitions reagents.

As an example for two different competition reagents, the binding partner C of the receptor molecule binding reagent might be a streptavidin binding peptide and the binding site Z of the multimerization reagent might be the biotin binding site of a streptavidin mutein. This binding can be disrupted by the addition of biotin or an analogue thereof. The ligand L of the solid phase might be a chelating group able to bind a hexahistidine tag and the ligand binding partner LB comprised in the multimerization reagent might be a hexahistidine tag. This binding can be disrupted by addition of a chelating agent such as EDTA or a competitor such as imidazole.

It might however be advantageous that the same competition reagent is used for disrupting the reversible bond formed between the binding partner C and the binding site Z and for disrupting the bond formed between the ligand binding partner LB and the ligand L. As an example for this embodiment, the binding partner C of the receptor molecule binding reagent might be a streptavidin binding peptide and the binding site Z of the multimerization reagent might be the biotin binding site of a streptavidin mutein. The ligand L of the solid phase might be also be biotin and the ligand binding partner LB comprised in the multimerization reagent is again the biotin binding site of the streptavidin mutein. The binding can be in both cases disrupted by the addition of biotin or an analogue thereof. Thus, in such an embodiment, the binding site Z and the ligand binding partner LB of the multimerization agent might be identical. It is noted that in such an embodiment, a multimerization reagent is used that after multimerizing the receptor molecule binding reagent (by forming the multivalent complexes in which two or more receptor molecule binding reagents are bound to the multimerization reagent) still has free binding sites Z (which is then the same as the ligand binding partner LB) for the subsequent binding of the ligand L. The respective conditions can be determined empirically by the person skilled in the art, for example, by varying the molar ratio of multimerization reagent to receptor molecule binding reagent and determining the rate of the subsequent binding of these multivalent binding complexes to the solid phase that carries the ligand L.

In accordance with the above, the same binding pairs that can be used as the binding partner C and the binding site Z can also be used as ligand L and ligand binding partner LB. In illustrative examples, the ligand L and the ligand binding partner LB form a binding pair selected from the group of streptavidin or a streptavidin analog as ligand binding partner LB and a ligand L (molecule) binding to streptavidin, a binding pair that binds in the presence of a divalent cation, an oligohistidine peptide as ligand L and a binding moiety A comprising at least two chelating groups K as ligand binding partner LB, wherein each chelating group is capable of binding to a transition metal ion, thereby rendering moiety A capable of binding to the oligohistidine peptide, an antigen and an antibody against said antigen, wherein said ligand L comprises the antigen and said ligand binding partner LB comprises the antibody against said antigen, a protein selected from the group of glutathione-S-transferase, maltose binding protein (MBP), a chitin binding domain, and a cellulose binding domain as ligand binding partner LB and a glutathione, maltose, chitin, or cellulose, respectively as ligand L, an antibody Fc domain as ligand binding partner LB and an immunoglobulin binding protein such as protein A, protein G or protein L as ligand L.

A method as disclosed herein may be carried out at any temperature at which the viability of the target cell is at least essentially uncompromised. When reference is made herein to conditions that are at least essentially not harmful, not detrimental or at least essentially not compromising viability, conditions are referred to, under which the percentage of target cells that can be recovered with full viability, is at least 70%, including at least 75%, at least 80%, at least 85%, at least 90%, at least 92%, at least 95%, at least 97%, at least 98%, at least 99% or at least 99.5%. In some embodiments a method according to the invention is carried out at a temperature of about 20° C. or below, such as about 14° C. or below, about 9° C. or below or about 6° C. or below. Depending on the target cell to be isolated a suitable temperature range may for instance be from about 2° C. to about 45° C., including from about 2° C. to about 40° C., from about 3° C. to about 35° C., or from about 4° C. to about 30° C. if an aqueous medium is used to encompass the target cell. In some embodiments a method according to the invention is carried out at a constant temperature value, or at a selected temperature value ±about 5° C., ±about 4° C., ±about 3° C., ±about 2° C., ±about 1° C. or ±about 0.5° C.

The temperature may, for example, be selected to have a value of about 5° C., about 10° C., about 15° C., about 20° C. or about 25° C. In some embodiments the temperature is altered, i.e. increased, decreased or varied by combinations thereof, during a method according to the present invention. The temperature may for example be altered within a range as defined above, e.g. in the range from about 2° C. to about 40° C. or within the range from about 3° C. to about 35° C. The person skilled in the art is able to empirically determine a suitable temperature, taking into account the nature of the cells and the isolation conditions. For example, temperature insensitive cells such as cancer cells might isolated at room temperature or even elevated temperature such as 37° C.

In the method of the invention the one or more binding sites B of the receptor molecule binding reagent, which specifically binds to the receptor molecule, may for instance be an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). In some embodiments one or more binding sites of the receptor molecule binding reagent may be a bivalent proteinaceous artificial binding molecule such as a dimeric lipocalin mutein that is also known as "duocalin". In some embodiments the receptor binding reagent may have a single second binding site, i.e., it may be monovalent. Examples of monovalent receptor binding reagents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

As mentioned above, an example of a proteinaceous binding molecule with antibody-like functions is a mutein based on a polypeptide of the lipocalin family (see for example, WO 03/029462, Beste et al., *Proc. Natl. Acad. Sci. U.S.A.* (1999) 96, 1898-1903). Lipocalins, such as the bilin binding protein, the human neutrophil gelatinase-associated lipocalin, human Apolipoprotein D or human tear lipocalin possess natural ligand-binding sites that can be modified so that they bind a given target. Further examples of a proteinaceous binding molecule with antibody-like binding properties that can be used as a receptor binding reagent that specifically binds to the receptor molecule include, but are not limited to, the so-called glubodies (see e.g. international patent application WO 96/23879), proteins based on the ankyrin scaffold (Mosavi, L. K., et al., *Protein Science* (2004) 13, 6, 1435-1448) or crystalline scaffold (e.g. international patent application WO 01/04144) the proteins described in Skerra, *J. Mol. Recognit.* (2000) 13, 167-187, AdNectins, tetranectins and avimers. Avimers, including multivalent avimer proteins evolved by exon shuffling of a family of human receptor domains, contain so called A-domains that occur as strings of multiple domains in several cell surface receptors (Silverman, J., et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.).

Yet further examples of suitable proteinaceous binding molecules are an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994) 13, 5303-5309), a diabody (cf. Holliger et al., PNAS USA (1993)90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

A method as disclosed herein may also be carried out using a kit of parts, for instance, designed for performing a method as detailed above. The kit may include a receptor molecule binding reagent as defined above. The kit may for example include a container filled with the receptor binding reagent, e.g. in solution. The kit may further include a multimerization reagent as defined above. The kit may for example include a container filled with the multimerization reagent, e.g. in solution. The kit may also include a chromatography matrix as defined above, which may be (pre) packed into a column, such as a cartridge. Associated with such chromatography matrix and/or container(s) there is in some embodiments provided a notice in the form of instructions on how to use the kit to carry out a method according to the present invention.

A method as described herein may also include the use of a plurality of stationary phases, e.g. several chromatography columns that are used independent from each other. A method described may also include the use of a plurality of receptor molecule binding reagents and multimerization reagents, used independent from each other. In some embodiments a first set of matching receptor molecule binding reagents, multimerization reagents and stationary phases, and a second and any further set(s) of matching receptor binding reagents, multimerization reagents and stationary phases are used. Such a combination may be used to carry out a method according to the invention a plurality of times. In one embodiment the target cell has a plurality of different receptor molecules on its surface. For each of the receptors the method according to the invention may be carried out separately. When the target cell is immobilized to the stationary phase in a second run of a method of the invention, any left over reagents from the first run, i.e. a different receptor binding reagent and multimerization reagent, do typically not bind to the stationary phase and are thereby removed from the target cell. Any repetition of a method as described herein may, nevertheless, also include the use of a stationary phase that serves as a "removal cartridge"—in addition to providing a suitable ligand for the respective multivalent binding complex formed to immobilize the target cell—in removing any reagents left over from the previous run. Hence, a first run designed for a first receptor molecule on the target cell may involve using a first receptor molecule binding reagent and a first multimerization reagent. A second run designed for a second receptor molecule may involve using a second receptor molecule binding reagent and a second multimerization reagent.

The invention further provides an arrangement for isolating a target cell from a sample. This arrangement comprises
a solid phase comprising a ligand L, wherein the ligand L is capable of specifically binding a ligand binding partner LB, the ligand binding partner LB being present in a receptor molecule binding reagent or a multimerization reagent used for isolating the target cell, the ligand L thereby allowing reversible immobilization of the target cell on the solid phase,
at least one of
a) a first stationary phase, wherein the first stationary phase is suitable for cell separation, the first stationary phase being a gel filtration matrix and/or affinity chromatography matrix, wherein the matrix comprises an affinity reagent having a binding site Z specifically binding to a binding partner C comprised in the receptor molecule binding reagent, thereby allowing immobilization of the receptor molecule binding reagent on the first stationary phase and removal of the receptor molecule binding reagent from an eluate comprising the target cell,
or
b) a second stationary phase, wherein the second stationary phase comprises the ligand L, wherein the ligand L is capable of specifically binding to the ligand binding partner LB being present in the receptor molecule binding reagent or the multimerization reagent used for isolating the target cell, the ligand L thereby allowing immobilization of the receptor molecule binding reagent or the multimerization reagent on the second stationary phase and removal of the receptor molecule binding reagent or the multimerization reagent from an eluate comprising the target cell.

In this arrangement the solid phase and the at least one of the first or second stationary phase may be fluidly connected. In one embodiment, of the arrangement the first stationary phase and/or the second stationary phase is comprised in a chromatography column or is a planar stationary phase.

In a further embodiment, the solid phase is comprised in a batch reactor for isolating the target cell. The batch reactor may be a vessel comprising a solid phase on which the ligand L is immobilized thereon. Alternatively, the batch reactor comprises beads having the ligand L immobilized thereon. In a different embodiment, the solid phase is a stationary phase that is suitable for chromatography.

In case the batch reactor comprises beads, the arrangement of the invention may further comprise retaining means for retaining the beads in the batch reactor. If the beads are magnetic beads, the retaining means may be magnets.

In one embodiment of the arrangement the solid phase is fluidly connected to the first stationary phase and the first stationary phase is fluidly connected to the second stationary phase. Alternatively, the order of the stationary phase in the arrangement may be reversed such that the solid phase is fluidly connected to the second stationary phase and the second stationary phase is fluidly connected to the first stationary phase.

In one embodiment of the arrangement of the ligand L comprised in the solid phase and/or the second stationary phase is biotin or a derivative of biotin. Examples of such derivatives of biotin include, but are not limited to, desthiobiotin, iminobiotin, 2-(4'-hydroxyazobenzene) benzoic acid (HABA) or a streptavidin binding peptide.

In further embodiments of the arrangement of the invention the affinity reagent comprised in the first stationary phase may be streptavidin, a mutein of streptavidin, avidin or a mutein of avidin.

The invention is also directed to a device for isolating a target cell from a sample, wherein the device comprises an arrangement for isolating a target cell as disclosed here.

In accordance with the above, the invention is also directed to the use of a solid phase comprising a ligand L, wherein the ligand L is capable of specifically binding a ligand binding partner LB, for reversible immobilization or isolation of a target cell. In exemplary uses the ligand may be biotin or a derivative of biotin such as desthiobiotin, iminobiotin, 2-(4'-hydroxyazobenzene) benzoic acid (HABA) or a streptavidin binding peptide. The use of a solid phase comprising a ligand L, wherein the ligand L is capable of specifically binding a ligand binding partner LB, in a method of isolating a target cell or for immobilizing a target cell as defined here is in particular considered here As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXPERIMENTAL EXAMPLES

Example 1

Construction of a "Cell Purification Column"

The lower outlet of a Bio-Spin® Column (BioRad; Cat. No. 732-6008) is cut off about 45 mm from the upper end of the column (FIG. 8A). The remaining upper column body is clipped into the filter tube cap of a "Centrifuge and Test Tube" (Becton-Dickinson; Product Number 352235; see FIG. 8B). The cap contains a 35 µm nylon mesh which is capable of retaining Superflow™ resin. The cap with the column is placed back onto the 12×75 mm, 5 ml polystyrene round bottom test tube (FIG. 8A). The column is ready to be filled with Superflow resin.

Example 2

Preparation of Biotin-Superflow (0.38 mg/ml Biocytin)

Biocytin (Sigma-Aldrich, Cat. No. B4261) was coupled to Superflow® 6 (Sterogene, Cat. No. 806) according to standard procedures known in the art. Briefly the Superflow resin was washed and resuspended in 1 M $NaCO_3$. Activation was performed using Acetonitril (10 ml/ml); Bromcyan (0.2 g/ml). The resin was washed with 1 M $NaCO_3$, pH9.5 and 1 M HCl. Biocytin was coupled to the Superflow resin (0.38 mg/ml) in 0.1 M boric acid; 0.5 M $NaSO_4$ to yield Biotin-Superflow. The resulting Biotin-Superflow resin was washed with 50 mM Tris, pH8.0.

The Superflow® resin serves as solid phase in the isolation method of the present invention with biotin serving as ligand L to allow reversible immobilization of the target cell/multivalent binding complex on the stationary phase via the binding between the biotin as ligand L and the streptavidin mutein "Strep-Tactin® as ligand binding partner LB, Example 3

Isolation of Lymphocytes from Blood Using Ficoll Gradient Centrifugation

In this example Amersham-Biosciences Ficoll-Paque® Plus was used (6×500 ml #17-1440-03) in accordance with the protocol of the manufacturer. Briefly the required volume of Ficoll (3 ml for 4 ml diluted anticoagulated blood sample) was aseptically withdrawn using a syringe. Ficoll-Paque Plus (3 ml) was added to a centrifuge tube. Carefully a diluted blood sample (4 ml) was layered onto Ficoll-Paque® Plus. Centrifugation was carried out at 400×g for 20 minutes at room temperature (20° C.). The upper layer was drawn off using a clean Pasteur pipette, leaving the lymphocyte layer undisturbed at the interface. Using a clean Pasteur pipette the lymphocyte layer was transferred to a clean centrifuge tube. 3 volumes or more of balanced salt solution was added to the lymphocytes in the test tube. The lymphocytes were suspended by gently drawing them in and out of the Pasteur pipette. Centrifugation was carried out at 10-100×g and 18-20° C. for 10 minutes, and subsequently the supernatant was removed.

Example 4

Preparation of a Multivalent Binding Complex Containing Soluble Multimerized Strep-Tactin, Anti CD4 Fab Fragments Carrying a Streptavidin Binding Tag, and T Cells Cells of human buffy coat were prepared according to standard protocols used in the art. 100 µl of multimerised soluble Strep-Tactin (concentration 1.7 mg/ml, available as "Strep-Tactin® PE for Fab streptamer", catalogue number 6-5001-010, IBA GmbH Göttingen, Germany—it is noted here that the phycoerythrine (PE) fluorescent label of the streptavidin mutein was not used in these experiments while it was kept in the reagent since it does not interfere in the method of the invention) were mixed with 900 µl of Buffer IS (0.5% BSA (w/v) in phosphate buffered saline (PBS) pH 7.4 with PBS=8.06 mM $Na_2HPO_4$ 1.47 mM $KH_2PO_4$, 137 mM NaCl) to obtain a 1:10 dilution of 170 µg/ml. 6 µg of diluted multimerised Strep-Tactin (35.3 µl) were mixed with 4 µg of an CD4 binding Fab-fragment (16 µl of 250 µg/ml, available, for example, as part of the CD4 Fab Streptamer isolation kit catalogue number 6-8000-206, IBA GmbH, Göttingen, Germany) that carries at its heavy chain the streptavidin binding peptide (SAWSHPQFEK(GGGS)$_2$GG-SAWSHPQFEK, SEQ ID NO: 13, also known as Twin-Strep-Tag®) and 74 µl of Buffer IS to a final volume of 125 µl and incubated in a 15 ml tube for 45 min at 4° C. During this incubation, the Fab fragments will bind via their streptavidin binding peptide to the multimerized Strep-tactin (that serves as multimerization reagent).

An amount of $1 \times 10^7$ cells was added in a volume of 100 µl and incubated with the anti CD4 Fab-fragment/Strep-Tactin complexes for 20 min on ice. Cells were resuspended (for washing) in 10 ml Buffer IS, centrifuged at 400×g, the supernatant was removed and cells were resuspended in 3 ml Buffer IS. By so doing, multivalent binding complexes to which the target T cells were bound are formed.

Example 5

Chromatographic Isolation of CD4+ T Cells

A "cell purification column" was assembled according to the description in Example 1. The column was packed with a bed volume of 1 ml of Biotin-Superflow (0.38 mg/ml Biocytin) (see Example 2). Peripheral blood monocytes (PBMCs) were isolated from buffy coat as described in Example 3.

100 µl of multimerised Strep-Tactin (1.7 mg/ml) were mixed with 900 µl of Buffer IS to get a 1:10 dilution of 170 µg/ml. 6 µg of diluted multimerised Strep-Tactin (35.3 µl) were mixed with 4 µg of the anti CD4 Fab fragment (16 µl of 250 µg/ml) used in Example 4 and 74 µl of Buffer IS to a final volume of 125 µl and incubated in a 15 ml tube for 45 min at 4° C. In accordance with Example 4, $1 \times 10^7$ cells were added in a volume of 100 µl and incubated with the anti CD4 Fab fragment/Strep-Tactin for 20 min at 4° C. Cells were resuspended in 10 ml Buffer IS, centrifuged at 400×g, the supernatant was removed and cells were resuspended in 3 ml Buffer IS. The column was equilibrated with 2 times 1 ml chilled Buffer IS.

The cell suspension ($1 \times 10^7$ cells) obtained as in Example 4 was applied onto the column in 3 portions of 1 ml each in order to immobilize the target cells on the column via binding of the free binding sites of Strep-Tactin to the biotin of the solid phase. The total volume of 3 ml ran through the column within about 15 minutes. The flow through was collected. The column was washed with 5 times 1 ml Buffer IS. The total of 5 ml ran through the column within about 25 minutes. The flow through as well as the washing volumes were collected and pooled (Fraction D+W). The cells were eluted by the addition of 5 times 1 ml Buffer IS with 1 mM biotin and collected (Fraction E). The total of 5 ml ran through the column within about 20 minutes. To remove those cells which could not be eluted due to either unspecific binding or some kind of stacking within the column resin, the column was capped at the lower outlet, the resin was resuspended with 1 ml Buffer IS and vigorously mixed by pipetting up and down with a 1 ml pipet tip. Then the cap was removed and the flow out was collected. This procedure was repeated once and pooled with the first fraction to get Fraction R. All collected cell suspensions were washed by centrifugation (400×g) in Buffer IS and stained with gating antibodies. Staining was carried out in 50 µl Buffer IS with 2 µl of Gating Antibodies in this case CD3-PE and CD4-APC. Cells were incubated for 20 min at 4° C. in the dark and washed by centrifugation (400×g) in 200 µl Buffer IS ready for the FACS analysis. FACS analysis was performed in an Accuri C6 Flow Cytometer. FIG. 6A to 6F depict Accuri C6 plots of fractions measured in FACS analysis.

Results

FIG. 7 provides an overview of the results.

FACS analysis of total cells revealed a concentration of 39.56% CD4$^+$ cells within the population of gated lymphocytes.

Cells in the flow through and washing fractions were depleted to a concentration of 4.01% CD4$^+$ cells.

Elution by biotin revealed a purity of 95.04% of CD4+ cells.

After pipette treatment of the column resin physically eluted cells still showed a purity of 88.26%.

Example 6

Isolation of T Cells Using a Multivalent Binding Complex Containing GST-Tagged Strep-Tactin and Fab-Fragments Cells of human buffy coat will be prepared according to established procedures. A fusion protein of Strep-Tactin and Glutathione-S-transferase (GST) will be generated according to standard procedures. The fusion protein will be affinity purified using a GST Spin Trap column (GE Healthcare Biosciences, Uppsala, Sweden) according to the manufacturer's instructions. The GST-tagged Strep-Tactin is multimerised using a "Controlled Protein-Protein Crosslinking Kit" (Thermo Fisher Scientific Inc, Waltham, Mass., U.S.A., product 23456) according to the manufacturer's instructions. 125 µl of multimerised GST-tagged Strep-Tactin (2.0 mg/ml) will be mixed with 875 µl of phosphate buffered saline pH 7.3 to get a 1:8 dilution of 250 µg/ml. 6 µg of diluted multimerised GST-Strep-Tactin (35.3 µl) will be incubated with 4 µg of a Fab fragment carrying a streptavidin binding peptide, and subsequently added to cells as described in Example 4, using phosphate buffered saline pH 7.3 for resuspending the cells.

A "cell purification column" will be assembled according to Example 1. The column will be packed with a bed volume of 1 ml of Glutathione Sepharose (Glutathione Sepharose 4 Fast Flow, GE Healthcare Biosciences, Uppsala, Sweden). The column will be equilibrated twice with 1 ml chilled phosphate buffered saline pH 7.3. The cell suspension will be applied onto the column in small portions. The flow through will be collected and the column washed with 5 times 1 ml phosphate buffered saline pH 7.3. The wash fraction will be collected. The cells will be eluted by the addition of 1 ml 50 mM Tris/HCl, pH 8.0, with 10 mM glutathione and 1 mM biotin. The eluate will be collected. The column will further be washed with 5 times 1 ml 50 mM Tris/HCl, pH 8.0, containing 10 mM glutathione. Cells which do not elute can be removed as described in Example 5.

Example 7

Isolation of T Cells Using a Multivalent Binding Complex Containing Biotin-NTA, Fab-His Cells of human buffy coat will be prepared according to established procedures. A 6×His tagged CD4 binding Fab fragment will be generated according to standard procedures. The fusion protein will be affinity purified using a Ni-NTA spin column (Qiagen, Valencia, Calif., U.S.A.) according to the manufacturer's instructions. A conjugate of biotin and a plurality of nitrilotriacetic acid (NTA) moieties will be synthesized as described by Schmidt et al. (supra, 2011). The biotin/NTA conjugate will be dissolved in phosphate buffered saline pH 7.3, containing 1 mg/ml $NiCl_2$, at a concentration of about 0.1 µg/ml and contacted with streptavidin to form multimeric NTA moieties under keeping free biotin sites of streptavidin that can act as ligand binding partner LB. 88 µl of the multimerized biotin/Ni-NTA streptavidin conjugate will be mixed with 4 µg of 6×His tagged CD4-Fab (16 µl of 250 µg/ml) and 21 µl of Buffer IS to a final volume of 125 µl and incubated in a 15 ml tube for 1 hour at 4° C. $1\times10^7$ cells will be added in a volume of 100 µl and incubated with the multimerized CD4-Fab/biotin/Ni-NTA for 20 min on ice as described in Example 4, using phosphate buffered saline pH 7.3 for resuspending the cells.

A "cell purification column" will be assembled according to Example 1. The column will be packed with a bed volume of 1 ml Biotin-Superflow (0.38 mg/ml Biocytin) prepared in Example 2. The column will be equilibrated twice with 1 ml chilled phosphate buffered saline pH 7.3. The cell suspension will be applied onto the column in small portions. The flow through will be collected and the column washed with 5 times 1 ml phosphate buffered saline pH 7.3. The wash fraction will be collected. The cells will be eluted by the addition of 5 times 1 ml phosphate buffered saline pH 7.3, containing 1 mM EDTA. While the addition of EDTA releases the CD4 Fab fragments carrying the hexahistidine tag (the receptor molecule binding reagent) from the multimerization reagent and thereby also the cells from the solid phase, the multimerization reagent will remain (via the binding of streptavidin to the biotin that acts as ligand L of the solid phase) immobilized on the solid phase. The eluate will be collected. The column will further be washed with 5 times 1 ml phosphate buffered saline pH 7.3. Cells which do not elute can be removed as described in Example 5.

Example 8

Isolation of T Cells Using a Multivalent Binding Complex Containing FLAG-Strep-Tactin, Fab-Strep Cells of human buffy coat will be prepared according to established procedures. A CD4 binding Fab fragment carrying a streptavidin binding peptide will be employed as in Examples 4 and 5. A Strep-Tactin with a FLAG-tag (DYKDDDDK) will be generated according to standard procedures. The fusion protein will be affinity purified using ANTI-FLAG® M2 magnetic beads (Sigma-Aldrich) according to the manufacturer's instructions. The FLAG-tagged Strep-Tactin is multimerised using the "Controlled Protein-Protein Crosslinking Kit" (Thermo Fisher Scientific Inc, Waltham, Mass., U.S.A., product 23456) according to the manufacturer's instructions. Multimerised FLAG-tagged Strep-Tactin, Fab-Strep, and cells will be combined as described in Examples 4 and 6.

A "cell purification column" will be assembled according to Example 1. The column will be packed with a bed volume of 1 ml of ANTI-FLAG® M1 agarose affinity gel (Sigma-Aldrich). The column will be equilibrated twice with 1 ml chilled phosphate buffered saline pH 7.3. The cell suspension will be applied onto the column in small portions. The flow through will be collected and the column was washed with 5 times 1 ml phosphate buffered saline pH 7.3. The wash fraction will be collected. The cells will be eluted by the addition of 1 ml FLAG peptide solution (Sigma, product no. F3290) that also contains 1 mM biotin. The eluate will be collected. The column will further be washed with 2 times 1 ml FLAG peptide/biotin solution. Cells which do not elute can be removed as described in Example 5.

Example 9

Isolation of T Cells Using a Multivalent Binding Complex Containing Multimerized Calmodulin and a Fab-Fragment Carrying a Calmodulin Binding Peptide A fusion protein of a CD4 binding Fab fragment and a calmodulin binding peptide (CBP) will be generated according to standard procedures. This Fab fragment-CBP fusion protein will be affinity purified using Calmodulin Affinity Resin (Agilent Technologies, Santa Clara, Calif., U.S.A.) using the batch binding method according to the manufacturer's instructions. The multimerization reagent is oligomeric Strep-Tactin to which biotinylated calmodulin is added to yield multimerized calmodulin in a stoichiometry that keeps free biotin binding sites that can act as ligand binding partner LB. The anti CD4 Fab fragment-CBP fusion protein will be incubated with the oligomeric Strep-Tactin which has immobilized thereon the biotinylated calmodulin in Buffer IS for one hour at 4° C.

A "cell purification column" will be assembled according to Example 1. The column will be packed with a bed volume of 1 ml Biotin-Superflow (0.38 mg/ml Biocytin) prepared in Example 2. The column will be equilibrated twice with 1 ml chilled phosphate buffered saline pH 7.3. The cell suspension will be applied onto the column in small portions. The flow through will be collected and the column washed with 5 times 1 ml phosphate buffered saline pH 7.3. The wash fraction will be collected. The cells will be eluted by the addition of 5 times 1 ml phosphate buffered saline pH 7.3, containing 1 mM EDTA. Similar to Example 7, in this Example EDTA releases the CD4 Fab fragments carrying the calmodulin binding peptide (the receptor molecule binding reagent) from the multimerization reagent and thereby also the cells from the solid phase, while the multimerization reagent will remain (via the binding of streptavidin to the biotin that acts as ligand L of the solid phase) immobilized on the solid phase. The eluate will be collected. The column will further be washed with 5 times 1 ml phosphate buffered saline pH 7.3, containing 1 mM EDTA. Cells which do not elute can be removed as described in Example 5.

Example 10

Pipette Tip Based Single Step Purification of Human CD8+ Cells from PBMCs Using Unlabelled Cells and a Fab Fragment Functionalized Resin (State-of-the-Art) Versus Using Fab Fragment Pre-Incubated Cells and Biotin Resin of the Present Invention For this experiment buffy coat from whole-blood units were used to prepare peripheral blood mononuclear cells (PBMCs) using standard Ficoll-Hypaque density centrifugation at room temperature (cf. Example 3).

Example 10.1

Isolation of Unlabelled Cells Using a Fab Functionalized Resin According to a Prior Art Method (Comparative Example)

CD8+ cells were isolated from a PBMC preparation by chromatographic purification using a pipette tip as column, essentially as described in International Patent Application WO 2013/124474.

Briefly, a pipette tip filled with 100 µl of Strep-Tactin®-agarose (catalogue number: 6-0425-000, IBA GmbH, Göttingen) was loaded with 1.5 µg anti-CD8 Fab-fragment carrying a sequential arrangement of two Strep-tagII streptavidin binding modules (underlined), i.e. SAWSHPQFEK (GGGS)$_2$GGSAWSHPQFEK ((SEQ ID NO: 13), this sequence is also known under its trademark name "Twin-Strep-Tag®"), at the C-terminus of the heavy chain (subsequently named anti-CD8 Fab-TST and corresponding to a commercially available product having the catalogue number: 6-8003, IBA GmbH, Göttingen). To this end, 1.5 µg anti-CD8-Fab-TST in 300 µl Buffer IS were applied at a speed of 200 µl/min to the Strep-Tactin®-agarose containing pipette tip prior to cell isolation. For the isolation of the target cells 1×10$^7$ freshly prepared PBMCs resuspended in 1 ml Buffer IS were applied onto the Strep-Tactin®-agarose matrix present in the pipette tip by two up-and-down cycles of the sample using a speed of 300 µl/min. Unbound (CD8-negative) cells were subsequently removed from the tip by washing three times (pipetting buffer up and down) with 1 ml Buffer IS at a speed of 2 ml/min. Finally, CD8+ target cells were eluted from the tip by detaching bound cells from the affinity matrix by rinsing with 1 ml 100 µM D-biotin solution at a flow rate of 600 µl/min and subsequently by flushing with 2×1 ml Buffer IS at a flow rate of 2 ml/min. Eluted CD8-positive and previously removed CD8-negative fractions were pooled independently (in separate vessels) and analysed by flow cytometry to determine yield and purity. To this end, cells were resuspended in 100 µl Buffer IS and stained at 4° C. with anti-human CD8-PE (OKT8) (from BioLegend, Cat. No. 300908) and anti-human CD3-APC (OKT3) (from BioLegend, Cat. No. 317318) antibodies for 20 minutes in the dark. Afterwards, cells were washed and resuspended in Buffer IS. Propidium iodide (PI) was added to distinguish between dead and living cells. Data were acquired with a flow cytometer (Accuri C6, BD) and analyzed with C Flow Plus Analysis software (BD).

Example 10.2

Isolation of Cells Pre-Incubated with Fab Fragment Using a Biotinylated Resin According to the Method of the Invention 1 µg of multimerized soluble Strep-Tactin (catalogue number: 6-0911-000, IBA GmbH, Göttingen that was used as multimerization reagent) was incubated with 1.5 µg anti-CD8 Fab-TST (that serves a receptor molecule binding reagent that contains the binding partner C for the multimerization reagent) for 45 minutes at 4° C. in the dark. Freshly prepared PBMCs (1×10$^7$ cells in 30 µl Buffer IS) were transferred to the preparation of the Fab-fragment/multimerized Strep-Tactin. The reaction mixture containing the PMBC and the multimerized Strep-Tactin onto which the Fab fragments were loaded was incubated for 20 minutes at 4° C. in the dark and washed once with 1 ml Buffer IS.

A pipette tip was filled with 100 µl of Biotin-agarose (catalogue number: 6-0446-000, IBA GmbH, Göttingen) that served as the solid phase comprising the ligand L. The cells pre-incubated with anti-CD8 Fab-TST/multimerized Strep-Tactin were applied onto the Strep-Tactin®-agarose matrix present in the pipette tip by using 2 up-and-down cycles of the sample using a speed of 300 µl/min. Unbound (CD8-negative) cells were subsequently removed from the tip by washing three times (pipetting buffer up and down) with 1 ml Buffer IS at a speed of 2 ml/min. Finally, CD8+ target cells were eluted from the tip by detaching bound cells from the affinity matrix by rinsing with 1 ml 100 µM D-biotin solution at a flow rate of 600 µl/min and subsequently by flushing with 2×1 ml Buffer IS at a flow rate of 2 ml/min. Eluted CD8-positive and previously removed CD8-negative fractions were pooled independently (in separate vessels) and analyzed by flow cytometry to determine yield and purity. To this end, cells were resuspended in 100 µl Buffer IS and stained at 4° C. with anti-human CD8-PE (OKT8) (from BioLegend, Cat. No. 300908) and anti-human CD3-APC (OKT3) (from BioLegend, Cat. No. 317318) antibodies for 20 minutes in the dark. Afterwards, cells were washed and resuspended in Buffer IS. Propidium iodide (PI) was added to distinguish between dead and living cells. Data were acquired with a flow cytometer (Accuri C6, BD) and analyzed with C Flow Plus Analysis software (BD).

Comparison of the Results of Examples 10.1 and 10.2

As can be seen from the Accuri C6 plots of representative isolation experiments using the method of described in International Patent Application WO 2013/124474 (FIG. 9A) and the method of the invention (FIG. 9B), both methods are able to isolate the CD8+ target cells. The comparison of the results of both methods depicted in FIG. 9C (the number 0015 denotes the result of the method of International Patent Application WO 2013/124474, while the number 0016 denotes the result of the method of the invention in FIG. 9C; numbers in % are mean values of three independent experiments), show that the CD8+ cells were obtained with a yield of 89% and at a purity of 70% using the method of the invention while the method of International Patent Application WO 2013/124474 provided a yield of 72% of CD8+ cells at a purity of 63% when equal amounts of anti-CD8 Fab-TST were used as receptor molecule binding reagent. This shows that the method of the invention improves both yield and purity of the target cells that are to be isolated.

Example 11

Pipette Based Single Step Purification of Human CD3+ Cells from PBMCs Using Unlabeled Cells and a Fab Fragment Functionalized Resin Vs. Fab Fragment Pre-Incubated Cells and Biotin Resin Using Reduced Amounts of Fab-Fragment Also in this example, the performance of the method of isolating target cells of the present invention was compared with the chromatographic purification using a pipette tip as described in International Patent Application WO 2013/124474.

In this experiment CD3+ cells were isolated from a PBMC preparation by the use of a pipette tip as described in Example 10 using unlabeled cells and a Strep-tactin resin functionalized with Fab fragments as described in International Patent Application WO 2013/124474. As a comparison CD3+ cells were isolated using cell pre-incubated with Fab fragments and biotin resin according to the method of the present invention. The anti-CD3 Fab-fragment used (catalogue number: 6-8001, IBA GmbH, Göttingen) carried the Twin-Strep-Tag® (SAWSHPQFEK(GGGS)$_2$GG-SAWSHPQFEK; (SEQ ID NO: 13)), at the C-terminus of the heavy chain. In comparison to Example 10, the amount of Fab fragment was reduced from 1.5 µg to 0.75 µg while the resin volume, the amount of multimerized soluble Strep-Tactin and the number of cells, respectively, were left unchanged. Obtained CD3-positive and -negative fractions were analyzed by flow cytometry using anti-human CD3-APC (OKT3) (from BioLegend, Cat. No. 317318) and anti-human CD4-PE (OKT4) (from BioLegend, Cat. No. 317410) antibodies.

As can be seen from the Accuri C6 plots of representative isolation experiments using the method of described in International Patent Application WO 2013/124474 (FIG. 10A) and the method of the invention (FIG. 10B), under these conditions both methods are again able to isolate the CD8+ target cells. The comparison of the results of both methods depicted in FIG. 10C (the number 0015 denotes the results of the method of International Patent Application WO 2013/124474, while the number 0016 denotes the results of the method of the invention in FIG. 10C; numbers in % are mean values of three independent experiments), show that the CD8+ cells were obtained with a yield of 72% and at a purity of 90% using the method of the invention while the method of International Patent Application WO 2013/124474 provided a yield of only 9% of CD8+ cells at a purity of 77% when equal amounts of 0.75 anti-CD8 Fab-TST were used as receptor molecule binding reagent. Thus, while using the method of the invention both yield and purity of the target cells remained constant when reducing the amount of receptor molecule binding reagent by 50% (compared to the amount used in Example 10), the yield of the method of International Patent Application WO 2013/124474 dropped significantly.

Summarizing the results of Examples 5, 10 and 11, the method of the invention is able to isolate CD4+, CD8+ and CD3+ cells from PBMC preparations. The comparison of Examples 10 and 11 show that in contrast to the method described in International Patent Application WO 2013/124474) the amount of receptor molecule binding reagent (such as an Fab fragment carrying a streptavidin binding peptide as binding partner C) can be reduced without significant loss of yield and purity, thereby saving cost and resources. This comparison also shows that the method of the invention is more robust than the method described in International Patent Application WO 2013/124474.

Example 12

Isolation of B Cells Using a Biotinylated Resin of the Invention, Strep-Tactin and Fab-Fragments 1 µg of multimerized soluble Strep-Tactin (catalogue number: 6-0911-000, IBA GmbH, Göttingen that was used as multimerization reagent) are incubated with 1.5 µg anti-CD19 Fab fragment available from IBA GmbH under catalogue number 6-8013-100. This Fab fragment ("anti-CD19 Fab-TST") carries the Twin-Strep-Tag® at the C-terminus of the heavy chain and thus serves as the receptor molecule binding reagent that contains the binding partner C for the multimerization reagent) for 45 minutes at 4° C. in the dark. Freshly prepared PBMCs (1×10$^7$ cells in 30 µl Buffer IS) are transferred to the preparation of the Fab-fragment/multimerized Strep-Tactin. The reaction mixture containing the PMBC and the multimerized Strep-Tactin on which the Fab fragments are loaded will be incubated for 20 minutes at 4° C. in the dark and washed once with 1 ml Buffer IS.

A pipette tip is filled with 100 µl of Biotin-agarose (catalogue number: 6-0446-000, IBA GmbH, Göttingen) that serves as the solid phase comprising the ligand L. The cells pre-incubated with anti-CD19 Fab-TST/multimerized Strep-Tactin are then applied onto the Strep-Tactin®-agarose matrix present in the pipette tip by using 2 up-and-down cycles of the sample using a speed of 300 µl/min. Unbound (CD19-negative) cells are subsequently removed from the tip by washing three times (pipetting buffer up and down) with 1 ml Buffer IS at a speed of 2 ml/min. Finally, CD19+ target cells are eluted from the tip by detaching bound cells from the affinity matrix by rinsing with 1 ml 100 µM D-biotin solution at a flow rate of 600 µl/min and subsequently by flushing with 2×1 ml Buffer IS at a flow rate of 2 ml/min. Eluted CD19-positive and previously removed CD19-negative fractions are pooled independently (in separate vessels) and analyzed by flow cytometry to determine yield and purity. To this end, cells are resuspended in 100 µl Buffer IS and stained at 4° C. with human anti-CD19-APC antibodies (obtained from eBioscience, don: SJ25C1, Cat.-No.: 17-0198-42) for 20 minutes in the dark. Afterwards, cells are washed and resuspended in Buffer IS. Propidium iodide (PI) is added to distinguish between dead and living cells. Data are acquired with a flow cytometer (Accuri C6, BD) and analyzed with C Flow Plus Analysis software (BD).

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of isolating a target cell, wherein the target cell is a mammalian cell comprising a receptor molecule on the target cell surface, the method comprising:
   contacting
   i) a receptor molecule binding reagent, the receptor molecule binding reagent comprising a binding site B and a binding partner C, wherein the binding site B comprised in the receptor molecule binding reagent is capable of specifically binding to the receptor molecule on the target cell surface and is selected from the group consisting of an antibody, a divalent antibody fragment, and a monovalent antibody fragment, and
   wherein the binding partner C comprised in the receptor molecule binding reagent is capable of reversibly binding to a binding site Z on a multimerization reagent,
   ii) a multimerization reagent,
   wherein the multimerization reagent is soluble and present in solution, and comprises two or more binding sites Z capable of reversibly binding to the binding partner C comprised in the receptor molecule binding reagent,
   wherein the multimerization reagent further comprises a ligand binding partner LB, the ligand binding partner LB being capable of specifically binding a ligand L, and
   iii) a sample, the sample comprising the target cell, thereby allowing the receptor molecule binding reagent, the multimerization reagent and the target cell to form a multivalent binding complex comprising the target cell bound to two or more receptor molecule binding reagents that are bound to the multimerization reagent,
   contacting the multivalent binding complex of target cell, receptor molecule binding reagent and multimerization reagent with a solid phase chromatography matrix, the solid phase chromatography matrix comprising the ligand L, wherein the solid phase chromatography matrix is a non-magnetic material or non-magnetisable material,
   thereby allowing reversible immobilization of the target cell on the solid phase chromatography matrix via the binding between the ligand L and the ligand binding partner LB, wherein immobilization of the target cell on the solid phase chromatography matrix is reversible upon disruption of at least the binding between the binding partner C comprised in the receptor molecule binding reagent and the binding site Z of the multimerization reagent.

2. The method of claim 1, wherein the receptor molecule binding reagent and the multimerization reagent are contacted with each other to form a complex comprising two or more receptor molecule binding reagents bound to the multimerization reagent prior to contacting (incubating) this complex with the target cell.

3. The method of claim 1, wherein the dissociation constant ($K_d$) for the binding between the receptor molecule binding reagent and the receptor molecule is of low affinity.

4. The method of claim 3, wherein the dissociation constant ($K_d$) for the binding between said receptor molecule binding reagent and said receptor molecule is in the range of about $10^{-3}$ M to about $10^{-10}$ M, or about $10^{-3}$ M to about $10^{-9}$ M, or about $10^{-3}$ M to about $10^{-8}$ M, or about $10^{-3}$ M to about $10^{-7}$ M.

5. The method of claim 4, further comprising collecting the target cell released from the solid phase chromatography matrix.

6. The method of claim 1, wherein the dissociation constant ($K_d$) for the binding between said receptor molecule binding reagent and said receptor molecule is in the range of about $10^{-2}$ to about $10^{-10}$ M.

7. The method of claim 1, wherein the reversible bond formed between the partner C comprised in the receptor molecule binding reagent and the binding site Z of the multimerization reagent is displaceable (disruptable) under competitive conditions.

8. The method of claim 7, comprising contacting the solid phase chromatography matrix with a competition reagent, the competition reagent being capable of disrupting the reversible bond formed between the binding partner C and the binding site Z, thereby disrupting the target cell/multivalent binding complex and allowing releasing the target cell (by elution) from the solid phase chromatography matrix.

9. The method of claim 1, wherein the bond formed between the ligand binding partner LB comprised in the multimerization reagent and the ligand L comprised on the solid phase chromatography matrix is displaceable (disruptable).

10. The method of claim 9, wherein the bond formed between the ligand binding partner LB and the ligand L is displaceable (disruptable) under competitive conditions.

11. The method of claim 10, comprising contacting the solid phase chromatography matrix with a competition reagent, the competition reagent being capable of displacing (disrupting) the bond formed between the ligand binding partner LB and the ligand L, thereby releasing the target cell from the solid phase chromatography matrix.

12. The method of claim 1, wherein the reversible bond formed between the partner C comprised in the receptor molecule binding reagent and the binding site Z of the multimerization reagent and the reversible bond formed between the ligand binding partner LB comprised in the multimerization reagent and the ligand L comprised on the solid phase chromatography matrix is displaceable (disruptable) under competitive conditions, and wherein the same competition reagent is used for disrupting the reversible bond formed between the binding partner C and the binding site Z and for disrupting the bond formed between the ligand binding partner LB and the ligand L.

13. The method of claim 1, wherein the reversible bond between the binding partner C comprised in the receptor molecule binding reagent and the binding site Z of the multimerization reagent has a $K_d$ between about $10^{-5}$ and about $10^{-13}$ M.

14. The method of claim 1, wherein the binding partner C and the binding site Z form a binding pair selected from the group of streptavidin or a streptavidin analog and a ligand binding to streptavidin, a binding pair that binds in the presence of a divalent cation, an oligohistidine peptide and a binding moiety A comprising at least two chelating groups K, wherein each chelating group K is capable of binding to a transition metal ion, thereby rendering binding moiety A capable of binding to the oligohistidine peptide, an antigen and an antibody against said antigen, wherein said binding partner C comprises the antigen and said multimerization reagent comprises the antibody against said antigen.

15. The method of claim 14, wherein (a) said binding partner C comprises biotin and said multimerization reagent comprises a streptavidin analog or an avidin analog that reversibly binds to biotin, (b) said binding partner C comprises a biotin analog that reversibly binds to streptavidin or avidin and said multimerisation reagent comprises streptavidin, or avidin, or a streptavidin analog, or an avidin analog that reversibly binds to said biotin analog, or (c) said binding partner C comprises a streptavidin or avidin binding peptide and said multimerization reagent comprises streptavidin, or avidin, or a streptavidin analog, or an avidin analog that reversibly binds to said streptavidin or avidin binding peptide.

16. The method of claim 15, wherein said multimerization reagent comprises a streptavidin mutein comprising the amino acid sequence Val$^{44}$-Thr$^{45}$-Ala$^{46}$-Arg$^{47}$ (SEQ ID NO: 19) at sequence positions 44 to 47 of wild-type streptavidin or a streptavidin mutein comprising the amino acid sequence Ile$^{44}$-Gly$^{45}$-Ala$^{46}$-Arg$^{47}$ (SEQ ID NO: 20) at sequence positions 44 to 47 of wild-type streptavidin and wherein said binding partner C comprises the streptavidin-binding peptide that comprises or consists of one of the following sequences:

a) -Trp-Xaa-His-Pro-Gln-Phe-Yaa-Zaa- (SEQ ID NO: 1), wherein Xaa is any amino acid and Yaa and Zaa are both Gly or Yaa is Glu and Zaa is Lys or Arg, b) -Trp-Arg-His-Pro-Gln-Phe-Gly-Gly- (SEQ ID NO: 2), c) -Trp-Ser-His-Pro-Gln-Phe-Glu-Lys- (SEQ ID NO: 3), d) a sequential arrangement of at least two streptavidin binding peptides, wherein each peptide binds streptavidin, wherein the distance between two peptides is at least 0 and not greater than 50 amino acids and wherein each of the at least two peptides comprises the amino acid sequence -His-Pro-Baa- in which Baa is selected from the group consisting of glutamine, asparagine and methionine, e) a sequential arrangement as recited in d), wherein one of the at least two peptides comprises the sequence -His-Pro-Gln-, f) a sequential arrangement as recited in d), wherein one of the peptides comprises an amino acid sequence -His-Pro-Gln-Phe- (SEQ ID NO: 4), g) a sequential arrangement as recited in d) wherein at least one peptide includes at least the amino sequence -Oaa-Xaa-His-Pro-Gln-Phe-Yaa-Zaa- (SEQ ID NO: 5), where Oaa is Trp, Lys or Arg, Xaa is any amino acid and where either Yaa and Zaa are both Gly or Yaa is Glu and Zaa is Lys or Arg, h) a sequential arrangement as recited in d) wherein at least one peptide includes at least the amino acid sequence -Trp-Xaa-His-Pro-Gln-Phe-Yaa-Zaa- (SEQ ID NO: 6) where Xaa is any amino acid and where either Yaa and Zaa are both Gly or Yaa is Glu and Zaa is Lys or Arg, i) a sequential arrangement as recited in d) wherein at least one peptide includes at least the amino acid sequence -Trp-Ser-His-Pro-Gln-Phe-Glu-Lys- (SEQ ID NO: 7),
j) the amino acid sequence -Trp-Ser-His-Pro-Gln-Phe-Glu-Lys- (Xaa)n-Trp-Ser-His-Pro-Gln-Phe-Glu-Lys- (SEQ ID NO: 8) wherein Xaa is any amino acid and n is an integer from 0 to 12,
k) an amino acid sequence selected from the group consisting of Trp-Arg-His-Pro-Gln-Phe-Gly-Gly (SEQ ID NO: 9), Trp-Ser-His-Pro-Gln-Phe-Glu-Lys (SEQ ID NO: 10), Trp-Ser-His-Pro-Gln-Phe-Glu-Lys-(GlyGlyGlySer)$_3$-Trp-Ser-His-Pro-Gln-Phe-Glu-Lys (SEQ ID NO: 11), Trp-Ser-His-Pro-Gln-Phe-Glu-Lys-(GlyGlyGlySer)$_2$-Trp-Ser-His-Pro-Gln-Phe-Glu-Lys (SEQ ID NO: 12) or Trp-Ser-His-Pro-Gln-Phe-Glu-Lys-(GlyGlyGlySer)$_2$-Gly-Gly-Ser-Ala-Trp-Ser-His-Pro-Gln-Phe-Glu-Lys (SEQ ID NO: 13).

17. The method of claim 1, wherein the target cell is selected from the group consisting of a stem cell, a lymphocyte and a cancer cell.

18. A method of isolating a target cell, wherein the target cell is a mammalian cell comprising a receptor molecule on the target cell surface, the method comprising:
contacting
i) a receptor molecule binding reagent,
the receptor molecule binding reagent comprising a binding site B and a binding partner C, wherein the binding site B comprised in the receptor molecule binding reagent is capable of specifically binding to the receptor molecule on the target cell surface and is selected from the group consisting of an antibody, a divalent antibody fragment, and a monovalent antibody fragment,
wherein the binding partner C comprised in the receptor molecule binding reagent is capable of reversibly binding to a binding site Z on a multimerization reagent, and
wherein the receptor molecule binding reagent further comprises a ligand binding partner LB, the ligand binding partner LB being capable of specifically binding a ligand L,
and
ii) a multimerization reagent,
wherein the multimerization reagent is soluble and present in solution, and comprises two or more binding sites Z capable of reversibly binding to the binding partner C comprised in the receptor molecule binding reagent,
iii) a sample, the sample comprising the target cell,
thereby allowing the receptor molecule binding reagent, the multimerization reagent and the target cell to form a multivalent binding complex comprising the target cell bound to two or more receptor molecule binding reagents that are bound to the multimerization reagent,
contacting the multivalent binding complex of target cell, receptor molecule binding reagent and multimerization reagent with a solid phase chromatography matrix, the solid phase chromatography matrix comprising the ligand L, wherein the solid phase chromatography matrix is a non-magnetic material or non-magnetisable material,
thereby allowing reversible immobilization of the target cell on the solid phase chromatography matrix via the binding between the ligand L and the ligand binding partner LB, wherein immobilization of the target cell on the solid phase chromatography matrix is reversible upon disruption of a) the binding between the binding partner C comprised in the receptor molecule binding reagent and the binding site Z of the multimerization reagent and/or
b) the binding between the ligand L of the solid phase chromatography matrix and the ligand binding partner LB comprised in the receptor molecule binding reagent.

19. A method of immobilizing a target cell on a solid phase chromatography matrix, wherein the target cell is a mammalian cell comprising a receptor molecule on the target cell surface, the method comprising:
contacting
i) a receptor molecule binding reagent,
the receptor molecule binding reagent comprising a binding site B and a binding partner C, wherein the binding site B comprised in the receptor molecule binding reagent is capable of specifically binding to the receptor molecule on the target cell surface and is selected from the group consisting of an antibody, a divalent antibody fragment, and a monovalent antibody fragment, and
wherein the binding partner C comprised in the receptor molecule binding reagent is capable of reversibly binding to a binding site Z on a multimerization reagent,
ii) a multimerization reagent,
wherein the multimerization reagent is soluble and present in solution, and comprises two or more binding sites Z capable of reversibly binding to the binding partner C comprised in the receptor molecule binding reagent,
wherein the multimerization reagent further comprises a ligand binding partner LB, the ligand binding partner LB being capable of specifically binding a ligand L,
and
ii) a sample, the sample comprising the target cell,
thereby allowing the receptor molecule binding reagent, the multimerization reagent and the target cell to form a multivalent binding complex comprising the target cell bound to two or more receptor molecule binding reagents that are bound to the multimerization reagent,
contacting the multivalent binding complex of target cell, receptor molecule binding reagent and multimerization reagent with a solid phase chromatography matrix, the solid phase chromatography matrix comprising the ligand L, wherein the solid phase chromatography matrix is a non-magnetic material or non-magnetisable material,
thereby allowing reversible immobilization of the target cell on the solid phase chromatography matrix via the binding between the ligand L and the ligand binding partner LB, wherein immobilization of the target cell on the solid phase chromatography matrix is reversible upon disruption of at least the binding between the binding partner C comprised in the receptor molecule binding reagent and the binding site Z of the multimerization reagent.

20. A method of immobilising a target cell on a solid phase chromatography matrix, wherein the target cell has a receptor molecule on the target cell surface, the method comprising:
contacting
i) a receptor molecule binding reagent,
the receptor molecule binding reagent comprising a binding site B and a binding partner C, wherein the binding site B comprised in the receptor molecule binding reagent is capable of specifically binding to the receptor molecule on the target cell surface and is selected from the group consisting of an antibody, a divalent antibody fragment, and a monovalent antibody fragment, wherein the binding partner C comprised in the receptor molecule binding reagent is capable of reversibly binding to a binding site Z on a multimerization reagent, and wherein the receptor molecule binding reagent further comprises a ligand binding partner LB, the ligand binding partner LB being capable of specifically binding a ligand L, and ii) a multimerization reagent, wherein the multimerization reagent is soluble and present in solution, and comprises two or more binding sites Z capable of reversibly binding to the binding partner C comprised in the receptor molecule binding reagent, iii) a sample, the sample comprising the target cell, thereby allowing the receptor molecule binding reagent, the multimerization reagent and the target cell to form a multivalent binding complex comprising the target cell bound to two or more receptor molecule binding reagents that are bound to the multimerization reagent, contacting the multivalent binding complex of target cell, receptor molecule binding reagent and multimerization reagent with a solid phase chromatography matrix, the solid phase chromatography matrix comprising the ligand L, wherein the solid phase chromatography matrix is a non-magnetic material or non-magnetisable material, thereby allowing reversible immobilization of the target cell on the solid phase chromatography matrix via the binding between the ligand L and the ligand binding partner LB, wherein immobilization of the target cell on the solid phase chromatography matrix is reversible upon disruption of a) the binding between the binding partner C comprised in the receptor molecule binding reagent and the binding site Z of the multimerization reagent and/or b) the binding between the ligand L of the solid phase chromatography matrix and the ligand binding partner LB comprised in the receptor molecule binding reagent.

* * * * *

SEQUENCE LISTING

```
<160> NUMBER OF SEQ ID NOS: 21

<210> SEQ ID NO 1
<211> LENGTH: 8
<212> TYPE: PRT
<213> ORGANISM: artificial
<220> FEATURE:
<223> OTHER INFORMATION: straptavidin-binding peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Gly or Glu
<220> FEATURE:
<221> NAME/KEY: MISC_FEATURE
<222> LOCATION: (8)..(8)
<223> OTHER INFORMATION: Xaa is Gly, Lys, or Arg

<400> SEQUENCE: 1

Trp Xaa His Pro Gln Phe Xaa Xaa
1               5

<210> SEQ ID NO 2
<211> LENGTH: 8
<212> TYPE: PRT
<213> ORGANISM: artificial
<220> FEATURE:
<223> OTHER INFORMATION: straptavidin-binding peptide

<400> SEQUENCE: 2

Trp Arg His Pro Gln Phe Gly Gly
1               5

<210> SEQ ID NO 3
<211> LENGTH: 8
<212> TYPE: PRT
<213> ORGANISM: artificial
<220> FEATURE:
<223> OTHER INFORMATION: straptavidin-binding peptide

<400> SEQUENCE: 3
```

```
Trp Ser His Pro Gln Phe Glu Lys
1               5

<210> SEQ ID NO 4
<211> LENGTH: 4
<212> TYPE: PRT
<213> ORGANISM: artificial
<220> FEATURE:
<223> OTHER INFORMATION: synthetic peptide

<400> SEQUENCE: 4

His Pro Gln Phe
1

<210> SEQ ID NO 5
<211> LENGTH: 8
<212> TYPE: PRT
<213> ORGANISM: artificial
<220> FEATURE:
<223> OTHER INFORMATION: straptavidin-binding peptide
<220> FEATURE:
<221> NAME/KEY: MISC_FEATURE
<222> LOCATION: (1)..(1)
<223> OTHER INFORMATION: Xaa is Trp, Lys or Arg
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Gly or Glu
<220> FEATURE:
<221> NAME/KEY: MISC_FEATURE
<222> LOCATION: (8)..(8)
<223> OTHER INFORMATION: Xaa is Gly, Lys, or Arg

<400> SEQUENCE: 5

Xaa Xaa His Pro Gln Phe Xaa Xaa
1               5

<210> SEQ ID NO 6
<211> LENGTH: 8
<212> TYPE: PRT
<213> ORGANISM: artificial
<220> FEATURE:
<223> OTHER INFORMATION: straptavidin-binding peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Gly or Glu
<220> FEATURE:
<221> NAME/KEY: MISC_FEATURE
<222> LOCATION: (8)..(8)
<223> OTHER INFORMATION: Xaa is Gly, Lys, or Arg

<400> SEQUENCE: 6

Trp Xaa His Pro Gln Phe Xaa Xaa
1               5

<210> SEQ ID NO 7
<211> LENGTH: 8
<212> TYPE: PRT
<213> ORGANISM: artificial
<220> FEATURE:
<223> OTHER INFORMATION: straptavidin-binding peptide
```

```
<400> SEQUENCE: 7

Trp Ser His Pro Gln Phe Glu Lys
1               5

<210> SEQ ID NO 8
<211> LENGTH: 28
<212> TYPE: PRT
<213> ORGANISM: artificial
<220> FEATURE:
<223> OTHER INFORMATION: streptavidin binding peptide
<220> FEATURE:
<221> NAME/KEY: MISC_FEATURE
<222> LOCATION: (9)..(20)
<223> OTHER INFORMATION: Xaa is any amino acid and up to twelve of them
      may be absent

<400> SEQUENCE: 8

Trp Ser His Pro Gln Phe Glu Lys Xaa Xaa Xaa Xaa Xaa Xaa Xaa Xaa
1               5                   10                  15

Xaa Xaa Xaa Xaa Trp Ser His Pro Gln Phe Glu Lys
            20                  25

<210> SEQ ID NO 9
<211> LENGTH: 8
<212> TYPE: PRT
<213> ORGANISM: artificial
<220> FEATURE:
<223> OTHER INFORMATION: straptavidin-binding peptide

<400> SEQUENCE: 9

Trp Arg His Pro Gln Phe Gly Gly
1               5

<210> SEQ ID NO 10
<211> LENGTH: 8
<212> TYPE: PRT
<213> ORGANISM: artificial
<220> FEATURE:
<223> OTHER INFORMATION: straptavidin-binding peptide

<400> SEQUENCE: 10

Trp Ser His Pro Gln Phe Glu Lys
1               5

<210> SEQ ID NO 11
<211> LENGTH: 28
<212> TYPE: PRT
<213> ORGANISM: artificial
<220> FEATURE:
<223> OTHER INFORMATION: straptavidin-binding peptide

<400> SEQUENCE: 11

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 12
<211> LENGTH: 24
<212> TYPE: PRT
<213> ORGANISM: artificial
<220> FEATURE:
<223> OTHER INFORMATION: straptavidin-binding peptide

<400> SEQUENCE: 12

Trp Ser His Pro Gln Phe Glu Lys Gly Gly Gly Ser Gly Gly Gly Ser
```

```
1               5                   10                  15

Trp Ser His Pro Gln Phe Glu Lys
            20

<210> SEQ ID NO 13
<211> LENGTH: 28
<212> TYPE: PRT
<213> ORGANISM: artificial
<220> FEATURE:
<223> OTHER INFORMATION: straptavidin-binding peptide

<400> SEQUENCE: 13

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 14
<211> LENGTH: 10
<212> TYPE: PRT
<213> ORGANISM: artificial
<220> FEATURE:
<223> OTHER INFORMATION: Myc-tag

<400> SEQUENCE: 14

Glu Gln Lys Leu Ile Ser Glu Glu Asp Leu
1               5                   10

<210> SEQ ID NO 15
<211> LENGTH: 9
<212> TYPE: PRT
<213> ORGANISM: artificial
<220> FEATURE:
<223> OTHER INFORMATION: HA-tag

<400> SEQUENCE: 15

Tyr Pro Tyr Asp Val Pro Asp Tyr Ala
1               5

<210> SEQ ID NO 16
<211> LENGTH: 11
<212> TYPE: PRT
<213> ORGANISM: artificial
<220> FEATURE:
<223> OTHER INFORMATION: VSV-G-tag

<400> SEQUENCE: 16

Tyr Thr Asp Ile Glu Met Asn Arg Leu Gly Lys
1               5                   10

<210> SEQ ID NO 17
<211> LENGTH: 11
<212> TYPE: PRT
<213> ORGANISM: artificial
<220> FEATURE:
<223> OTHER INFORMATION: HSV-tag

<400> SEQUENCE: 17

Gln Pro Glu Leu Ala Pro Glu Asp Pro Glu Asp
1               5                   10

<210> SEQ ID NO 18
<211> LENGTH: 14
<212> TYPE: PRT
<213> ORGANISM: artificial
<220> FEATURE:
```

```
<223> OTHER INFORMATION: V5-tag

<400> SEQUENCE: 18

Gly Lys Pro Ile Pro Asn Pro Leu Leu Gly Leu Asp Ser Thr
1               5                   10

<210> SEQ ID NO 19
<211> LENGTH: 4
<212> TYPE: PRT
<213> ORGANISM: artificial
<220> FEATURE:
<223> OTHER INFORMATION: straptavidin analog sequence positions 44 to 47

<400> SEQUENCE: 19

Val Thr Ala Arg
1

<210> SEQ ID NO 20
<211> LENGTH: 4
<212> TYPE: PRT
<213> ORGANISM: artificial
<220> FEATURE:
<223> OTHER INFORMATION: straptavidin analog sequence positions 44 to 47

<400> SEQUENCE: 20

Ile Gly Ala Arg
1

<210> SEQ ID NO 21
<211> LENGTH: 10
<212> TYPE: PRT
<213> ORGANISM: artificial
<220> FEATURE:
<223> OTHER INFORMATION: T7 epitope

<400> SEQUENCE: 21

Ala Ser Met Thr Gly Gly Gln Gln Met Gly
1               5                   10
```